US012215384B2

(12) United States Patent
Gutierrez et al.

(10) Patent No.: US 12,215,384 B2
(45) Date of Patent: Feb. 4, 2025

(54) METHODS OF CHARACTERISING TARGET POLYNUCLEOTIDES

(71) Applicant: Oxford Nanopore Technologies PLC

(72) Inventors: Richard Alexander Gutierrez, Oxford (GB); Andrew John Heron, Oxford (GB); James White, Oxford (GB)

(73) Assignee: Oxford Nanopore Technologies PLC, Oxford (GB)

( * ) Notice: Subject to any disclaimer, the term of this patent is extended or adjusted under 35 U.S.C. 154(b) by 359 days.

(21) Appl. No.: 16/304,077

(22) PCT Filed: May 25, 2017

(86) PCT No.: PCT/GB2017/051491
§ 371 (c)(1),
(2) Date: Nov. 21, 2018

(87) PCT Pub. No.: WO2017/203268
PCT Pub. Date: Nov. 30, 2017

(65) Prior Publication Data
US 2019/0203288 A1 Jul. 4, 2019

(30) Foreign Application Priority Data
May 25, 2016 (GB) .................................... 1609241
May 27, 2016 (GB) .................................... 1609436

(51) Int. Cl.
C12Q 1/6869 (2018.01)

(52) U.S. Cl.
CPC ..... *C12Q 1/6869* (2013.01); *C12Q 2565/631* (2013.01)

(58) Field of Classification Search
CPC ............ C12Q 1/6869; C12Q 2565/631; C12Q 2521/513; C12Q 2525/301; C12Q 2537/163
See application file for complete search history.

(56) References Cited

U.S. PATENT DOCUMENTS

| | | | |
|---|---|---|---|
| 7,338,807 B2 | 3/2008 | Harris et al. | |
| 7,625,706 B2 | 12/2009 | Akeson et al. | |
| 7,745,116 B2 | 6/2010 | Williams | |
| 7,851,203 B2 | 12/2010 | Letant et al. | |
| 7,947,454 B2 | 5/2011 | Akeson et al. | |
| 8,105,846 B2 | 1/2012 | Bayley et al. | |
| 8,785,211 B2 | 7/2014 | Bayley et al. | |
| 8,828,208 B2 | 9/2014 | Canas et al. | |
| 9,617,591 B2 | 4/2017 | Moysey et al. | |
| 9,758,823 B2 | 9/2017 | Moysey et al. | |
| 9,797,009 B2 | 10/2017 | Heron et al. | |
| 10,221,450 B2 | 3/2019 | Heron et al. | |
| 10,322,150 B2 | 6/2019 | Honda et al. | |
| 10,385,382 B2 | 8/2019 | Moysey et al. | |
| 10,392,658 B2 | 8/2019 | Bowen et al. | |
| 10,443,097 B2 | 10/2019 | Jayasinghe et al. | |
| 10,480,026 B2 * | 11/2019 | Garalde | C12N 9/14 |
| 10,724,018 B2 | 7/2020 | Bruce et al. | |
| 10,724,087 B2 | 7/2020 | Moysey et al. | |
| 10,808,231 B2 | 10/2020 | Heron et al. | |
| 10,844,432 B2 | 11/2020 | Jayasinghe et al. | |
| 11,180,741 B2 | 11/2021 | Heron et al. | |
| 11,965,183 B2 | 4/2024 | Heron et al. | |
| 2003/0010638 A1 | 1/2003 | Hansford et al. | |
| 2004/0058378 A1 | 3/2004 | Kong et al. | |
| 2004/0248114 A1 | 12/2004 | Taira et al. | |
| 2006/0063171 A1 | 3/2006 | Akeson et al. | |
| 2008/0293045 A1 | 11/2008 | Piepenburg et al. | |
| 2008/0311582 A1 * | 12/2008 | Bayley | G01N 33/48721 435/6.14 |
| 2009/0256116 A1 | 10/2009 | Shumaker-Parry et al. | |
| 2009/0269744 A1 * | 10/2009 | Krause | C12Q 1/6886 435/6.14 |
| 2010/0035260 A1 | 2/2010 | Olasagasti et al. | |
| 2010/0092960 A1 | 4/2010 | Fehr | |
| 2010/0120098 A1 | 5/2010 | Grunenwald et al. | |
| 2010/0221212 A1 | 9/2010 | Stagliano et al. | |
| 2010/0331194 A1 * | 12/2010 | Turner | G01N 27/44791 506/2 |
| 2011/0177498 A1 | 7/2011 | Clarke et al. | |
| 2011/0229877 A1 | 9/2011 | Jayasinghe et al. | |
| 2011/0311965 A1 | 12/2011 | Maglia et al. | |
| 2012/0058468 A1 | 3/2012 | Mckeown | |
| 2012/0107802 A1 | 5/2012 | Stoddart et al. | |
| 2013/0048499 A1 | 2/2013 | Mayer et al. | |

(Continued)

FOREIGN PATENT DOCUMENTS

| | | |
|---|---|---|
| CA | 2927728 A1 | 4/2015 |
| CA | 2937411 A1 | 7/2015 |

(Continued)

OTHER PUBLICATIONS

PCT/GB2017/051491, Aug. 28, 2017, International Search Report and Written Opinion.
PCT/GB2017/051491, Dec. 6, 2018, International Preliminary Report on Patentability.
International Preliminary Report on Patentability mailed Dec. 6, 2018, for Application No. PCT/GB2017/051491.
International Search Report and Written Opinion mailed on Aug. 28, 2019, for Application No. PCT/GB2017/051491.
[No Author Listed] Antibodies bind specific molecules through their hypervariable loops. 33.3 Antibody Binding. 6th edition. 2007;953-954.
[No Author Listed] Data sheet SEQ ID No. 10 search results from STIC, printed on Oct. 29, 2018, pp. 1-38 (Year: 2018).
[No Author Listed] Data sheet SEQ ID No. 2 search results from STIC, printed on Oct. 29, 18, pp. 1-24 (Year: 2018).

(Continued)

*Primary Examiner* — Narayan K Bhat
(74) *Attorney, Agent, or Firm* — Wolf, Greenfield & Sacks, P.C.

(57) ABSTRACT

The invention relates to a new method of characterising a target polynucleotide using a pore. The method involves controlling the formation of secondary structure by the target polynucleotide after the polynucleotide has moved through the pore.

19 Claims, 12 Drawing Sheets
Specification includes a Sequence Listing.

(56) References Cited

U.S. PATENT DOCUMENTS

| | | | |
|---|---|---|---|
| 2013/0118902 A1* | 5/2013 | Akeson | G01N 33/48721 204/456 |
| 2013/0149769 A1 | 6/2013 | Kizaki et al. | |
| 2013/0225421 A1 | 8/2013 | Li et al. | |
| 2013/0327644 A1* | 12/2013 | Turner | C12Q 1/68 204/543 |
| 2014/0051069 A1 | 2/2014 | Jayasinghe et al. | |
| 2014/0186823 A1 | 7/2014 | Clarke et al. | |
| 2014/0255921 A1 | 9/2014 | Moysey et al. | |
| 2014/0262784 A1 | 9/2014 | Clarke et al. | |
| 2014/0335512 A1 | 11/2014 | Moysey et al. | |
| 2015/0008126 A1 | 1/2015 | Maglia et al. | |
| 2015/0031020 A1 | 1/2015 | Jayasinghe et al. | |
| 2015/0065354 A1 | 3/2015 | Moysey et al. | |
| 2015/0152492 A1 | 6/2015 | Brown et al. | |
| 2015/0191709 A1 | 7/2015 | Heron et al. | |
| 2015/0197796 A1 | 7/2015 | White et al. | |
| 2015/0218629 A1 | 8/2015 | Heron et al. | |
| 2016/0257942 A1 | 9/2016 | Bruce et al. | |
| 2017/0002406 A1 | 1/2017 | Bowen et al. | |
| 2018/0030530 A1 | 2/2018 | Moysey et al. | |
| 2018/0037874 A9 | 2/2018 | Bruce et al. | |
| 2018/0179500 A1 | 6/2018 | Heron et al. | |
| 2018/0230526 A1 | 8/2018 | Heron et al. | |
| 2019/0345550 A1 | 11/2019 | Bowen et al. | |
| 2021/0009971 A1 | 1/2021 | Bruce et al. | |
| 2021/0123032 A1 | 4/2021 | Heron et al. | |
| 2021/0139972 A1 | 5/2021 | Jayasinghe et al. | |
| 2021/0172011 A1 | 6/2021 | Moysey et al. | |
| 2022/0135956 A1 | 5/2022 | Heron et al. | |
| 2023/0212535 A1 | 7/2023 | Bruce et al. | |
| 2023/0227799 A1 | 7/2023 | Heron et al. | |
| 2024/0060126 A1 | 2/2024 | Jayasinghe et al. | |

FOREIGN PATENT DOCUMENTS

| | | |
|---|---|---|
| CN | 104039979 A | 9/2014 |
| JP | 2006-500028 A | 1/2006 |
| WO | WO 2000/28312 A1 | 5/2000 |
| WO | WO 2002/092821 A1 | 11/2002 |
| WO | WO 2004/027025 A2 | 4/2004 |
| WO | WO 2005/124888 A1 | 12/2005 |
| WO | WO 2006/028508 A2 | 3/2006 |
| WO | WO 2006/100484 A2 | 9/2006 |
| WO | WO 2007/057668 A1 | 5/2007 |
| WO | WO 2008/102120 A1 | 8/2008 |
| WO | WO 2008/102121 A1 | 8/2008 |
| WO | WO 2008/124107 A1 | 10/2008 |
| WO | WO 2009/035647 A1 | 3/2009 |
| WO | WO 2009/044170 A1 | 4/2009 |
| WO | WO 2009/077734 A2 | 6/2009 |
| WO | WO 2010/004265 A1 | 1/2010 |
| WO | WO 2010/004273 A1 | 1/2010 |
| WO | WO 2010/034018 A2 | 3/2010 |
| WO | WO 2010/086602 A1 | 8/2010 |
| WO | WO 2010/086603 A1 | 8/2010 |
| WO | WO 2010/086622 A1 | 8/2010 |
| WO | WO 2010/109197 A1 | 9/2010 |
| WO | WO 2010/117470 A2 | 10/2010 |
| WO | WO 2010/122293 A1 | 10/2010 |
| WO | WO 2011/067559 A1 | 6/2011 |
| WO | WO 2012/033524 A2 | 3/2012 |
| WO | WO 2012/164270 A1 | 12/2012 |
| WO | WO 2013/014451 A1 | 1/2013 |
| WO | WO 2013/041878 A1 | 3/2013 |
| WO | WO 2013/057495 A2 | 4/2013 |
| WO | WO 2013/098561 A1 | 7/2013 |
| WO | WO 2013/098562 A2 | 7/2013 |
| WO | WO 2013/153359 A1 | 10/2013 |
| WO | WO 2013/185137 A1 | 12/2013 |
| WO | WO 2014/013259 A1 | 1/2014 |
| WO | WO 2014/013260 A1 | 1/2014 |
| WO | WO 2014/013262 A1 | 1/2014 |
| WO | WO 2014/064443 A2 | 5/2014 |
| WO | WO 2014/064444 A1 | 5/2014 |
| WO | WO 2014/135838 A1 | 9/2014 |
| WO | WO 2014/158665 A1 | 10/2014 |
| WO | WO 2015/022544 A1 | 2/2015 |
| WO | WO 2015/055981 A2 | 4/2015 |
| WO | WO 2015/110777 A1 | 7/2015 |
| WO | WO 2015/110813 A1 | 7/2015 |
| WO | WO 2015/124935 A1 | 8/2015 |
| WO | WO 2015/150786 A1 | 10/2015 |
| WO | WO 2016/034591 A2 | 3/2016 |
| WO | WO 2016/055777 A2 | 4/2016 |
| WO | WO 2016/059363 A1 | 4/2016 |
| WO | WO 2018/060740 A1 | 4/2018 |
| WO | WO 2018/100370 A1 | 6/2018 |

OTHER PUBLICATIONS

[No Author Listed] Press release: Oxford Nanopore introduces DNA 'strand sequencing' on the high-throughput GridION platform and presents MinION, a sequencer the size of a USB; memory stick, Feb. 2012.

[No Author Listed] UniProt Database accession No. 17J3V8 sequence. Oct. 3, 2012.

[No Author Listed] UniProt Database accession No. k7nri8 sequence. Feb. 6, 2013.

Allen et al., The genome sequence of the psychrophilic archaeon, Methanococcoides burtonii: the role of genome evolution in cold adaptation. ISME J. Sep. 2009;3(9):1012-35. doi: 10.1038/ismej. 2009.45.

Altschul et al., Basic local alignment search tool. J Mol Biol. Oct. 5, 1990;215(3):403-10.

Altschul, A protein alignment scoring system sensitive at all evolutionary distances. J Mol Evol. Mar. 1993;36(3):290-300.

Arslan et al., Protein structure. Engineering of a superhelicase through conformational control. Science. Apr. 17, 2015;348(6232):344-7. doi: 10.1126/science.aaa0445.

Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.

Balakrishnan et al., Dna2 exhibits a unique strand end-dependent helicase function. J Biol Chem Dec. 10, 2010;285(50):38861-8. doi: 10.1074/jbc.M110.165191. Epub Oct. 6, 2010.

Balci et al., Single-molecule nanopositioning: structural transitions of a helicase-DNA complex during ATP hydrolysis. Biophys J. Aug. 17, 2011;101(4):976-84. doi: 10.1016/j.bpj.2011.07.010.

Benner et al., Sequence-specific detection of individual DNA polymerase complexes in real time using a nanopore. Nat Nanotechnol. Nov. 2007;2(11):718-24. doi: 10.1038/nnano.2007.344. Epub Oct. 28, 2007.

Bennett et al., Association of yeast DNA topoisomerase III and Sgs1 DNA helicase: studies of fusion proteins. Proc Natl Acad Sci U S A. Sep. 25, 2001;98(20):11108-13. Epub Sep. 11, 2001.

Berger, SnapShot: nucleic acid helicases and translocases. Cell. Sep. 5, 2008;134(5):888-888.e1. doi: 10.1016/j.cell.2008.08.027.

Bessler et al., The amino terminus of the *Saccharomyces cerevisiae* DNA helicase Rrm3p modulates protein function ltering replication and checkpoint activity. Genetics. Nov. 2004;168(3):1205-18.

Blast ® NCBI. Sequence ID No. 10; ZSYBNHWV114. Sep. 18, 2015.

Blast ® NCBI. Sequence ID No. 52; ZT1133A811N. Sep. 18, 2015.

Braha et al., Designed protein pores as components for biosensors. Chem Biol. Jul. 1997;4(7):497-505.

Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.

Buttner et al., Structural basis for DNA duplex separation by a superfamily-2 helicase. Nat Struct Mol Biol. Jul. 2007; 14(7):647-52.

(56) References Cited

OTHER PUBLICATIONS

Byrd et al., A parallel quadruplex DNA is bound tightly but unfolded slowly by pif1 helicase. J Biol Chem. Mar. 6, 2015;290(10):6482-94. doi:10.1074/jbc.M114.630749. Epub Jan. 14, 2015.
Byrd et al., Superfamily 2 helicases. Front Biosci (Landmark Ed). Jun. 1, 2012;17:2070-88.
Chandler et al., A new microparticles size calibration standard for use in measuring smaller microparticles using a new flow cytometer. J Thromb Haemost. Jun. 2011;9(6):1216-24. doi: 10.1111/j.1538-7836.2011.04283.x.
Cheng et al., Functional characterization of the multidomain F plasmid TraI relaxase-helicase. J Biol Chem. Apr. 8, 2011;286(14):12670-82. doi: 10.1074/jbc.M110.207563. Epub Feb. 2, 2011.
Colas et al., Microscopical investigations of nisin-loaded nanoliposomes prepared by Mozafari method and their bacterial targeting. Micron. 2007;38(8):841-7.
Comer et al., Microscopic mechanics of hairpin DNA translocation through synthetic nanopores. Biophys J. Jan. 2009;96(2):593-608. doi: 10.1016/j.bpj.2008.09.023.
Deamer, Nanopore analysis of nucleic acids bound to exonucleases and polymerases. Annu Rev Biophys. 2010;39:79-90. doi: 10.1146/annurev.biophys.093008.131250.
Derrington et al., Nanopore DNA sequencing with MspA. Proc Natl Acad Sci U S A. Sep. 14, 2010;107(37):16060-5. doi: 10.1073/pnas.1001831107. Epub Aug. 26, 2010.
Devereux et al., A comprehensive set of sequence analysis programs for the VAX. Nucleic Acids Res. Jan. 11, 1984;12(1 Pt 1):387-95.
Dostál et al., Tracking F plasmid TraI relaxase processing reactions provides insight into F plasmid transfer. Nucleic Acids Res. Apr. 2011;39(7):2658-70. doi: 10.1093/nar/gkq1137. Epub Nov. 24, 2010.
Dou et al., The DNA binding properties of the *Escherichia coli* RecQ helicase. J Biol Chem. Feb. 20, 2004;279(8):6354-63. Epub Dec. 9, 2003.
Durrieu et al., Interactions between neuronal fusion proteins explored by molecular dynamics. Biophys J. May 1, 2008;94(9):3436-46. doi: 10.1529/biophysj.107.123117. Epub Jan. 22, 2008.
Eliseev et al., Molecular Recognition of Nucleotides, Nucleosides, and Sugars by Aminocyclodextrins. J. Am. Chem. Soc., vol. 116:6081-6088 (1994).
Eoff et al., The Kinetic Mechanism for DNA Unwinding by Multiple Molecules of Dda Helicase Aligned on DNA. Biochemistry. Jun. 1, 2010; 49(21): 4543-4553. doi: 10.1021/bi100061v. Author Manuscript.
Fairman-Williams et al., SF1 and SF2 helicases: family matters. Curr Opin Struct Biol. Jun. 2010;20(3):313-24. doi:10.1016/j.sbi.2010.03.011. Epub Apr. 22, 2010.
Farah et al., The RecBCD enzyme initiation complex for DNA unwinding:enzyme positioning and DNA opening. J Mol Biol. Oct. 10, 1997;272(5):699-715.
Garalde et al., Highly parallel direct RNA sequencing on an array of nanopores. bioRxiv. 2016. doi: http://dx.doi.org/10.1101/068809.
Garcillán-Barcia et al., The diversity of conjugative relaxases and its application in plasmid classification. FEMS Microbiol Rev. May 2009;33(3):657-87.
Genbank accession No. AEA72977 sequence. Apr. 6, 2011.
Genbank Submission. NCBI; Accession No. AM778123. Richards et al.; Sep. 18, 2008.
GenPept Accession No. XP 003728286. Jun. 7, 2012.
Gonzalez-Perez et al., Biomimetic triblock copolymer membrane arrays: a stable template for functional membrane proteins. Langmuir. Sep. 15, 2009;25(18):10447-50. doi: 10.1021/la902417m.
Graham et al., Sequence-specific assembly of FtsK hexamers establishes directional translocation on DNA. Proc Natl Acad Sci U S A. Nov. 23, 2010;107(47):20263-8. doi: 10.1073/pnas.1007518107. Epub Nov. 3, 2010.
Grant et al., A facile method for attaching nitroxide spin labels at the 5' terminus of nucleic acids. Nucleic Acids Res. 2007;35(10):e77. Epub May 21, 2007.

Green et al., Quantitative evaluation of the lengths of homobifunctional protein cross-linking reagents used as molecular rulers. Protein Sci. Jul. 2001;10(7):1293-304.
Guo et al., The linker region between the helicase and primase domains of the bacteriophage T7 gene 4 protein is critical for hexamer formation. J Biol Chem. Oct. 15, 1999;274(42):30303-9.
Hammerstein et al., Subunit dimers of alpha-hemolysin expand the engineering toolbox for protein nanopores. J Biol Chem. Apr. 22, 2011;286(16):14324-34. doi: 10.1074/jbc.M111.218164. Epub Feb. 15, 2011.
He et al., The T4 phage SF1B helicase Dda is structurally optimized to perform DNA strand separation. Structure. Jul. 3, 2012;20(7):1189-200. doi:10.1016/j.str.2012.04.013. Epub May 31, 2012.
Heron et al., Simultaneous measurement of ionic current and fluorescence from single protein pores. J Am Chem Soc. Feb. 11, 2009;131(5):1652-3. doi: 10.1021/ja808128s.
Holden et al., Direct introduction of single protein channels and pores into lipid bilayers. J Am Chem Soc. May 11, 2005;127(18):6502-3.
Holden et al., Functional bionetworks from nanoliter water droplets. J Am Chem Soc. Jul. 11, 2007;129(27):8650-5. Epub Jun. 16, 2007.
Hopfner et al., Mechanisms of nucleic acid translocases: lessons from structural biology and single-molecule biophysics. Curr Opin Struct Biol. Feb. 2007;17(1):87-95. Epub Dec. 6, 2006.
Hornblower et al., Single-molecule analysis of DNA-protein complexes using nanopores. Nat Methods. Apr. 2007;4(4):315-7. Epub Mar. 4, 2007.
Howorka et al., Nanopore analytics: sensing of single molecules. Chem Soc Rev. Aug. 2009;38(8):2360-84. doi: 10.1039/b813796j. Epub Jun. 15, 2009.
Ivanov et al., DNA tunneling detector embedded in a nanopore. Nano Lett. Jan. 12, 2011;11(1):279-85. doi: 10.1021/nl1103873a. Epub Dec. 6, 2010.
James, Aptamers. Encyclopedia of Analytical Chemistry. R.A. Meyers (Ed.). 4848-4871. John Wiley & Sons Ltd, Chichester, 2000.
Jankowsky, RNA helicases at work: binding and rearranging. Trends Biochem Sci. Jan. 2011;36(1):19-29. doi: 10.1016/j.tibs.2010.07.008.
Japrung et al., Urea facilitates the translocation of single-stranded DNA and RNA through the alpha-hemolysin nanopore. Biophys J. May 19, 2010;98(9):1856-63. doi: 10.1016/j.bpj.2009.12.4333.
Jezewska et al., Interactions of *Escherichia coli* replicative helicase PriA protein with single-stranded DNA. Biochemistry. Aug. 29, 2000;39(34):10454-67.
Kafri et al., Dynamics of molecular motors and polymer translocation with sequence heterogeneity. Biophys J. Jun. 2004;86(6):3373-91.
Kalli et al., Conformational changes in talin on binding to anionic phospholipid membranes facilitate signaling by integrin transmembrane helices. PLoS Comput Biol. Oct. 2013;9(10):e1003316. doi:10.1371/journal.pcbi.1003316. Epub Oct. 31, 2013.
Kankia et al., Folding of the thrombin aptamer into a G-quadruplex with Sr(2+): stability, heat, and hydration. J Am Chem Soc. Nov. 7, 2001;123(44):10799-804.
Kar et al., Defining the structure-function relationships of bluetongue virus helicase protein VP6. J Virol. Nov. 2003;77(21):11347-56.
Keyser, Controlling molecular transport through nanopores. J R Soc Interface. Oct. 7, 2011;8(63):1369-78. doi: 10.1098/rsif.2011.0222. Epub Jun. 29, 2011.
Khafizov, Single Molecule Force Spectroscopy of Single Stranded Dna Binding Protein and Rep Helicase. University of Illinois at Urbana-Champaign Dissertation. 2012.
Korolev et al., Major domain swiveling revealed by the crystal structures of complexes of *E. coli* Rep helicase bound to single-stranded DNA and ADP. Cell. Aug. 22, 1997;90(4):635-47.
Kumar et al., Nonradioactive labeling of synthetic oligonucleotide probes with terminal deoxynucleotidyl transferase. Anal Biochem. Mar. 1988; 169(2):376-82. Erratum in: Anal Biochem Sep. 1988; 173(2):469.
Kuper et al., Functional and structural studies of the nucleotide excision repair helicase XPD suggest a polarity for DNA translocation. EMBO J. Jan. 18, 2012;31(2):494-502. doi: 10.1038/emboj.2011.374.

(56) References Cited

OTHER PUBLICATIONS

Kutyavin et al., Oligonucleotides containing 2-aminoadenine and 2-thiothymine act as selectively binding complementary agents. Biochemistry. Aug. 27, 1996;35(34):11170-6.
Langecker et al., Synthetic lipid membrane channels formed by designed DNA nanostructures. Science. Nov. 16, 2012;338(6109):932-6. doi: 10.1126/science.1225624.
Lee et al., Cooperative translocation enhances the unwinding of duplex DNA by SARS coronavirus helicase nsP13. Nucleic Acids Res. Nov. 2010;38(21):7626-36. doi: 10.1093/nar/gkq647. Epub Jul. 29, 2010.
Lee et al., Direct imaging of single UvrD helicase dynamics on long single-stranded DNA. Nat Commun. 2013;4:1878. doi:10.1038/ncomms2882.
Levin et al., Helicase from hepatitis C virus, energetics of DNA binding. J Biol Chem. Aug. 16, 2002;277(33):29377-85. Epub May 28, 2002.
Lieberman et al., Processive replication of single DNA molecules in a nanopore catalyzed by phi29 DNA polymerase. J Am Chem Soc. Dec. 22, 2010;132(50):17961-72. doi: 10.1021/ja1087612. Epub Dec. 1, 2010.
Liu et al., Adding new chemistries to the genetic code. Annu Rev Biochem. 2010;79:413-44. doi: 10.1146/annurev.biochem.052308.105824.
Liu et al., Structure of the DNA repair helicase XPD. Cell. May 30, 2008;133(5):801-12. doi: 10.1016/j.cell.2008.04.029.
Lohman et al., Mechanisms of helicase-catalyzed DNA unwinding. Annu Rev Biochem. 1996;65:169-214.
Lohman et al., Non-hexameric DNA helicases and translocases:mechanisms and regulation. Nat Rev Mol Cell Biol. May 2008;9(5):391-401. doi:10.1038/nrm2394.
Ma et al., Bright functional rotaxanes. Chem Soc Rev. Jan. 2010;39(1):70-80. doi: 10.1039/b901710k. Epub Jul. 21, 2009.
Maddox et al., Elevated serum levels in human pregnancy of a molecule immunochemically similar to eosinophil granule major basic protein. J Exp Med. Oct. 1, 1983;158(4):1211-26.
Manrao et al., Reading DNA at single-nucleotide resolution with a mutant MspA nanopore and phi29 DNA polymerase. Nat Biotechnol. Mar. 25, 2012;30(4):349-53. doi: 10.1038/nbt.2171.
Marathias et al., Structures of the potassium-saturated, 2:1, and intermediate, 1:1, forms of a quadruplex DNA. Nucleic Acids Res. May 1, 2000;28(9):1969-77.
Marini et al., A human DNA helicase homologous to the DNA cross-link sensitivity protein Mus308. J Biol Chem. Mar. 8, 2002;277(10):8716-23. Epub Dec. 18, 2001.
Marsault et al., Macrocycles are great cycles: applications, opportunities, and challenges of synthetic macrocycles in drug discovery. J Med Chem. Apr. 14, 2011;54(7):1961-2004. doi: 10.1021/jm1012374. Epub Mar. 7, 2011.
Marušič et al., Solution-state structure of an intramolecular G-quadruplex with propeller, diagonal and edgewise loops. Nucleic Acids Res. Aug. 2012;40(14):6946-56. doi: 10.1093/nar/gks329. Epub Apr. 24, 2012.
Mechanic et al., *Escherichia coli* DNA helicase II is active as a monomer. J Biol Chem. Apr. 30, 1999;274(18):12488-98.
Miles et al., Properties of Bacillus cereus hemolysin II: a heptameric transmembrane pore. Protein Sci. Jul. 2002;11(7):1813-24.
Montal et al., Formation of bimolecular membranes from lipid monolayers and a study of their electrical properties. Proc Natl Acad Sci U S A. Dec. 1972;69(12):3561-6.
Morris et al., Evidence for a functional monomeric form of the bacteriophage T4 DdA helicase. Dda does not form stable oligomeric structures. J Biol Chem. Jun. 8, 2001;276(23):19691-8. Epub Feb. 27, 2001.
Ngo et al., Computational complexity, protein structure prediction, and the levinthal paradox. 14. The protein folding problem teritary structure prediction. Ed(s):Merz et al. Birkhauser, Boston, Ma. 1994. 433, 492-5.

Nikolov et al., Behavior of giant vesicles with anchored DNA molecules. Biophys J. Jun. 15, 2007;92(12):4356-68. Epub Mar. 23, 2007.
Nishikiori et al., Crystal structure of the superfamily 1 helicase from Tomato mosaic virus. J Virol. Jul. 2012;86(14):7565-76. doi: 10.1128/JVI.00118-12. Epub May 9, 2012.
O'Shea et al., X-ray structure of the GCN4 leucine zipper, a two-stranded, parallel coiled coil. Science. Oct. 25, 1991;254(5031):539-44.
Pfeiffer et al., Bivalent cholesterol-based coupling of oligonucletides to lipid membrane assemblies. J Am Chem Soc. Aug. 25, 2004;126(33):10224-5.
Pinero-Fernandez et al., Indole transport across *Escherichia coli* membranes. J Bacteriol. Apr. 2011;193(8):1793-8. doi:10.1128/JB.01477-10. Epub Feb. 4, 2011.
Portakal et al., Construction of recB-recD genetic fusion and functional analysis of RecBDC fusion enzyme in *Escherichia coli*. BMC Biochem. Oct. 10, 2008;9:27. doi: 10.1186/1471-2091-9-27.
Raney et al., Structure and Mechanisms of SF1 DNA Helicases. Adv Exp Med Biol. 2013;767:17-46. doi: 10.1007/978-1-4614-5037-5_2.
Remaut et al., Protein-protein interaction through beta-strand addition. Trends Biochem Sci. Aug. 2006;31(8):436-44. Epub Jul. 7, 2006.
Richards et al., Structure of the DNA repair helicase hel308 reveals DNA binding and autoinhibitory domains. J Biol Chem. Feb. 22, 2008;283(8):5118-26. Epub Dec. 4, 2007.
Rudolf et al., The DNA repair helicases XPD and FancJ have essential iron-sulfur domains. Mol Cell. Sep. 15, 2006;23(6):801-8.
Rudolf et al., The helicase XPD unwinds bubble structures and is not stalled by DNA lesions removed by the nucleotide excision repair pathway. Nucleic Acids Res. Jan. 2010;38(3):931-41. doi:10.1093/nar/gkp1058.
Saariaho et al., Characteristics of MuA transposase-catalyzed processing of model transposon end DNA hairpin substrates. Nucleic Acids Res. Jun. 6, 2006;34(10):3139-49. Print 2006.
Satapathy et al., ATPase activity of RecD is essential for growth of the Antarctic Pseudomonas syringae Lz4W at low temperature. FEBS J. Apr. 2008;275(8):1835-51. doi:10.1111/j.1742-4658.2008.06342.x. Epub Mar. 9, 2008.
Sathiyamoorthy et al., The crystal structure of *Escherichia coli* group 4 capsule protein GfcC reveals a domain organization resembling that of Wza. Biochemistry. Jun. 21, 2011;50(24):5465-76. doi: 10.1021/bi101869h.
Schneider et al., DNA sequencing with nanopores. Nat Biotechnol. Apr. 10, 2012;30(4):326-8. doi: 10.1038/nbt.2181.
Sequence ID No. 2 Search Results. US-14-351-038-2. Sep. 16, 2015. 69 pages.
Singleton et al., Structure and mechanism of helicases and nucleic acid translocases. Annu Rev Biochem. 2007;76:23-50.
Soni et al., Synchronous optical and electrical detection of biomolecules traversing through solid-state nanopores. Rev Sci Instrum. Jan. 2010;81(1):014301. doi: 10.1063/1.3277116.
Stelter et al., Structural and mechanistic insight into DNA unwinding by Deinococcus radiodurans UvrD. PLoS One. Oct. 15, 2013;8(10):e77364. doi: 10.1371/journal.pone.0077364.
Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.
Troutt et al., Ligation-anchored PCR: a simple amplification technique with single-sided specificity. Proc Natl Acad Sci U S A. Oct. 15, 1992;89(20):9823-5. Erratum in: Proc Natl Acad Sci U S A Apr. 15, 1993;90(8):3775.
Tuteja et al., Unraveling DNA helicases. Motif, structure, mechanism and function. Eur J Biochem. May 2004;271(10):1849-63. Review. Erratum in: Eur J Biochem. Aug. 2004;271(15):3283.
UniProt Database accession No. a4sle1 sequence. May 15, 2007.
UniProt Database accession No. b4kac8 sequence. Sep. 23, 2008.
UniProt Database accession No. D0KN27. Dec. 15, 2009.
UniProt Database accession No. D7RM26 sequence. Aug. 10, 2010.
UniProt Database accession No. elqus6 sequence. Nov. 30, 2010.
UniProt Database accession No. i3d0e7 sequence. Jul. 11, 2012.

(56) References Cited

OTHER PUBLICATIONS

UniProt Database accession No. 16ZR75 sequence. Oct. 3, 2012.
UniProt Database accession No. k0im99 sequence. Nov. 28, 2012.
UniProt Database accession No. Q12WZ6 sequence. Apr. 12, 2017.
UniProt Database accession No. Q7Y5C3 sequence. Oct. 1, 2003.
Van Heel et al., Single-particle electron cryo-microscopy:towards atomic resolution. Q Rev Biophys. Nov. 2000;33(4):307-69.
Van Lengerich et al., Covalent attachment of lipid vesicles to a fluid-supported bilayer allows observation of DNA-mediated vesicle interactions. Langmuir. Jun. 1, 2010;26(11):8666-72. doi: 10.1021/la904822f.
Venkatesan et al., Nanopore sensors for nucleic acid analysis. Nat Nanotechnol. Sep. 18, 2011;6(10):615-24. doi: 10.1038/nnano.2011.129.
Vinson, Proteins in motion. Introduction. Science. Apr. 10, 2009;324(5924):197. doi:10.1126/science.324.5924.197.
Wang et al., DNA helicase activity of the RecD protein from Deinococcus radiodurans. J Biol Chem. Dec. 10, 2004;279(50):52024-32.
White, Structure, function and evolution of the XPD family of iron-sulfur-containing 5'-→3' DNA helicases. Biochem Soc Trans. 2009;37:547-551.
Woodman et al., Archaeal Hel308 domain V couples DNA binding to ATP hydrolysis and positions DNA for unwinding over the helicase ratchet. J Mol Biol. Dec. 14, 2007;374(5):1139-44. Epub Oct. 10, 2007.
Woodman et al., Molecular biology of Hel308 helicase in archaea. Biochem Soc Trans. Feb. 2009;37(Pt 1):74-8. doi: 10.1042/BST0370074.
Woodman et al., Winged helix domains with unknown function in Hel308 and related helicases. Biochem Soc Trans. Jan. 2011;39(1):140-4. doi:10.1042/BST0390140.
Yoshina-Ishii et al., Arrays of mobile tethered vesicles on supported lipid bilayers. J Am Chem Soc. Apr. 2, 2003;125(13):3696-7.
Yusko et al., Controlling the translocation of proteins through nanopores with bioinspired fluid walls. Nat Nanotechnol. Nat Nanotechnol. Apr. 2011; 6(4): 253-260. EPub Feb. 20, 2011. doi: 10.1038/nnano.2011.12 Author manuscript; available in PMC Oct. 1, 2011.
Zhang et al., Structural evidence for consecutive Hel308-like modules in the spliceosomal ATPase Brr2. Nat Struct Mol Biol. Jul. 2009;16(7):731-9. doi: 10.1038/nsmb.1625.
Ali et al., Kinetic measurement of the step size of DNA unwinding by *Escherichia coli* UvrD helicase. Science. Jan. 17, 1997;275(5298):377-80. doi: 10.1126/science.275.5298.377. Erratum in: Science Apr. 4, 1997;276(5309):21.
Guo et al., Protein tolerance to random amino acid change. Proc Natl Acad Sci U S A. Jun. 22, 2004;101(25):9205-10. doi: 10.1073/pnas.0403255101. Epub Jun. 14, 2004.
Jia et al., Rotations of the 2B Sub-domain of E. coli UvrD Helicase/Translocase Coupled to Nucleotide and DNA Binding. J Mol Biol. Aug. 19, 2011; 411(3): 633-648. EPub Jun. 17, 2011. doi: 10.1016/j.jmb.2011.06.019.
Jones et al., Protein secondary structure prediction based on position-specific scoring matrices. J Mol Biol. Sep. 17, 1999;292(2):195-202. doi: 10.1006/jmbi.1999.3091.
Kabsch et al., Dictionary of protein secondary structure: pattern recognition of hydrogen-bonded and geometrical features. Biopolymers. Dec. 1983;22(12):2577-637. doi: 10.1002/bip.360221211.
Theissen et al., Cooperative binding of ATP and RNA induces a closed conformation in a DEAD box RNA helicase. Proc Natl Acad Sci U S A. Jan. 15, 2008;105(2):548-53. doi: 10.1073/pnas.0705488105. Epub Jan. 9, 2008.
Zhang et al., DNA Binding and Unwinding Functional Analyses of Recombinant *E. coli* Helicase II (UvrD). Chinese J. of Biochem. Mol. Biol. 2007;23(9):764-9.
U.S. Appl. No. 16/902,301, filed Jun. 16, 2020, Moysey et al.
U.S. Appl. No. 17/064,329, filed Oct. 6, 2020, Heron et al.
Dong et al., Wza the translocon for *E. coli* capsular polysaccharides defines a new class of membrane protein. Nature. Nov. 9, 2006;444(7116):226-9. doi: 10.1038/nature05267. Epub Nov. 1, 2006.
Utama et al., Role of the DExH motif of the Japanese encephalitis virus and hepatitis C virus NS3 proteins in the ATPase and RNA helicase activities. Virology. Aug. 1, 2000;273(2):316-24. doi: 10.1006/viro.2000.0417.

\* cited by examiner

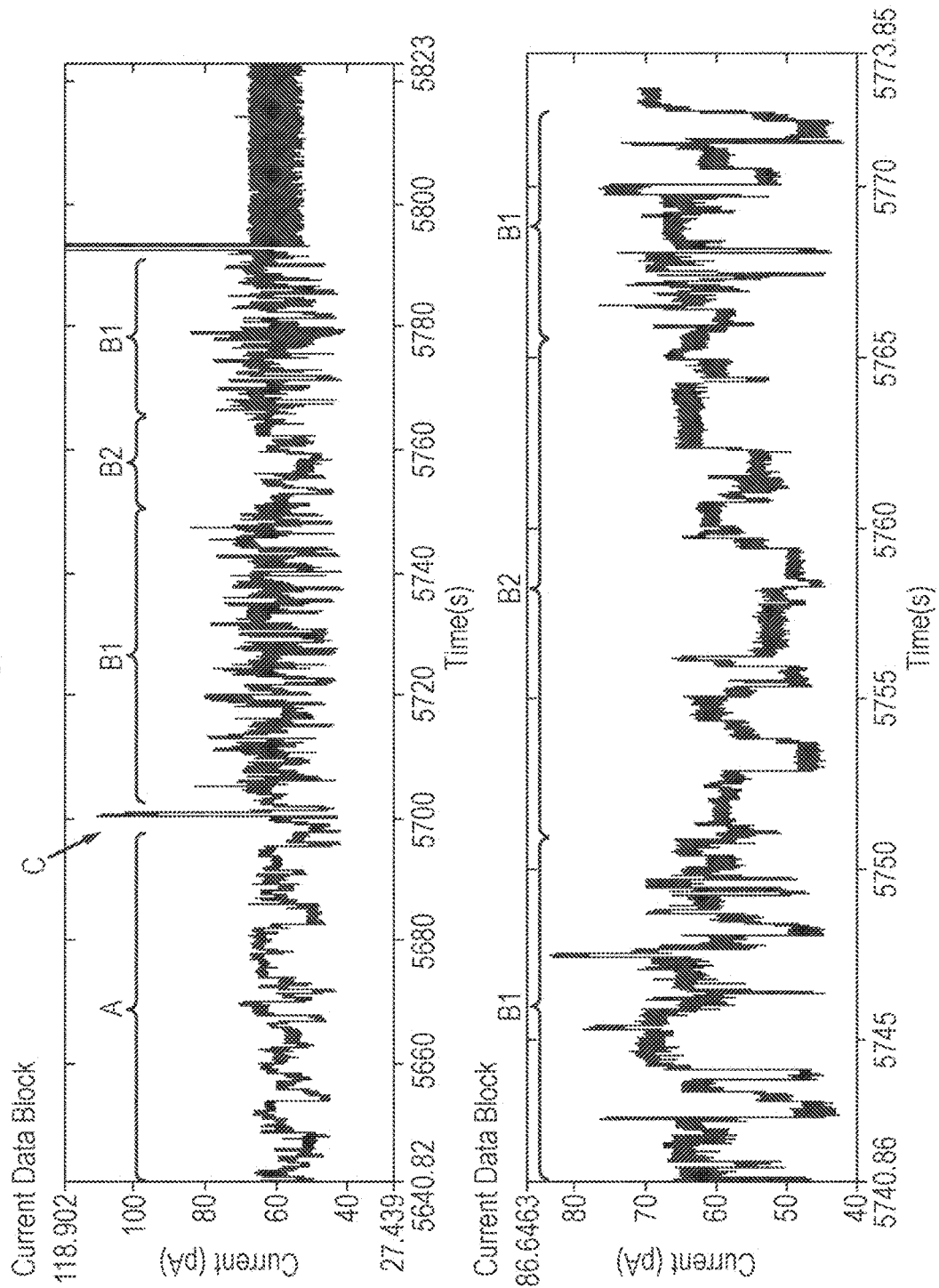

Fig. 6

| # | trans dna | # uplift | # no uplift | # delayed uplift | number of traces | # uplift% | # no uplift% | # delayed uplift% |
|---|---|---|---|---|---|---|---|---|
| 1 | | | | | | | | |
| 2 | 10nM AE202 + 10nM of hyped product (AE186 + TE60) | 3 | 27 | 13 | 43 | 6.98 | 62.79 | 30.23 |
| 3 | 10nM AE203 + 10nM of hyped product (AE186 + TE60) | 3 | 15 | 4 | 22 | 13.35 | 68.18 | 18.18 |
| 4 | 10nM AE210 + 10nM of hyped product (AE186 + TE60) | 6 | 20 | 5 | 31 | 19.35 | 64.52 | 16.13 |
| 5 | 500nM AE191 + 10nM of hyped product (AE186 + TE60) | 11 | 43 | 22 | 76 | 14.47 | 56.58 | 28.95 |
| 6 | 500nM AE191 + 10nM of hyped product (AE186 + TE60) + 1uM streptavidin | 10 | 28 | 15 | 53 | 18.87 | 52.83 | 28.30 |
| 7 | 500nM AE192 + 10nM of hyped product (AE186 + TE60) | 7 | 26 | 10 | 43 | 16.28 | 60.47 | 23.26 |
| 8 | 500nM AE192 + 10nM of hyped product (AE186 + TE60) + 1uM streptavidin | 4 | 14 | | 18 | 22.22 | 77.78 | 0.00 |
| 9 | 500nM AE193 + 10nM of hyped product (AE186 + TE60) | 2 | 12 | 8 | 22 | 9.09 | 54.76 | 36.36 |
| 10 | 500nM AE193 + 10nM of hyped product (AE186 + TE60) + 1uM streptavidin | 7 | 10 | 4 | 21 | 33.33 | 47.62 | 19.05 |
| 11 | 200nM each of AE263-AE272 | | 16 | 9 | 25 | 0.00 | 64.00 | 36.00 |
| 12 | 500nM each of AE273-AE292 | | 14 | 13 | 27 | 0.00 | 51.85 | 48.15 |
| 13 | no dna ctrl | 8 | 2 | 1 | 11 | 72.73 | 18.18 | 9.09 |
| 14 | 500nM each of AE272, AE271 + 400nM each of AE270 and AE269 + 300nM each of AE268 and AE267 + 200nM each of AE266, AE265 + 100nM each of AE264 and AE263 | | 43 | 10 | 53 | 0.00 | 81.13 | 18.87 |
| 15 | 500nM each of AE263, AE266, AE267, AE268, AE269, AE287, AE288, AE289, AE290, AE291, AE292 | | 14 | 9 | 23 | 0.00 | 60.87 | 39.13 |
| 16 | 500nM each of AE263-AE272 + 10nM AE210 | | 17 | 13 | 30 | 0.00 | 56.67 | 43.33 |
| 17 | | | | | | | | |

METHODS OF CHARACTERISING TARGET POLYNUCLEOTIDES

RELATED APPLICATIONS

This application is a national stage filing under 35 U.S.C. § 371 of international application number PCT/GB2017/051491, filed May 25, 2017, and claims the benefit under 35 U.S.C. § 119 (e) of GB application numbers 1609241.3, filed May 25, 2016, and 1609436.9, filed May 27, 2016, each of which is herein incorporated by reference in its entirety

FIELD OF THE INVENTION

The invention relates methods of characterising a target polynucleotide using a pore.

BACKGROUND TO THE INVENTION

There is currently a need for rapid and cheap polynucleotide (e.g. DNA or RNA) sequencing and identification technologies across a wide range of applications. Existing technologies are slow and expensive mainly because they rely on amplification techniques to produce large volumes of polynucleotide and require a high quantity of specialist fluorescent chemicals for signal detection.

Transmembrane pores (nanopores) have great potential as direct, electrical biosensors for polymers and a variety of small molecules. In particular, recent focus has been given to nanopores as a potential DNA sequencing technology.

When a potential is applied across a nanopore, there is a change in the current flow when an analyte, such as a nucleotide, resides transiently in the barrel for a certain period of time. Nanopore detection of the nucleotide gives a current change of known signature and duration. In the strand sequencing method, a single polynucleotide strand is passed through the pore and the identities of the nucleotides are derived. Strand sequencing can involve the use of a molecular brake to control the movement of the polynucleotide through the pore.

SUMMARY OF THE INVENTION

The inventors have surprisingly demonstrated that it is possible to improve the characterisation of a target polynucleotide by controlling the formation of secondary structure by the polynucleotide after it has moved through a transmembrane pore.

Accordingly, a method of characterising a target polynucleotide is provided, which comprises:
(a) contacting the target polynucleotide with one side of a transmembrane pore in a membrane and a molecular brake which controls the movement of the target polynucleotide through the pore; and
(b) taking one or more measurements which are indicative of one or more characteristics of the target polynucleotide as the polynucleotide moves with respect to the pore;
wherein the conditions on the other side of the pore are selected to control the formation of secondary structure by the target polynucleotide on the other side of the pore.

Also provided is a method of characterising a double stranded target polynucleotide, comprising:
(a) providing a construct comprising the target polynucleotide in which the two strands of the target polynucleotide are linked at one end of the target polynucleotide by a hairpin loop;
(b) contacting the construct with one side of a transmembrane pore in a membrane and a molecular brake which separates the two strands of the construct and controls the movement of the construct through the pore one strand at a time; and
(c) taking one or more measurements which are indicative of one or more characteristics of the target polynucleotide as the construct moves with respect to the pore;
wherein the hairpin loop is designed to control the ability of the two strands of the target polynucleotide to rehybridise on the other side of the pore.

Controlling the ability of the two strands of the target polynucleotide to rehybridise may may control the extent and/or consistency of formation of rehybridised polynucleotide (e.g. the proportion of polynucleotides that pass through the pore that rehybridise and the reproducibility of hybridisation, for example, in terms of how quickly it happens, how strong the binding is).

Further provided are:
a kit for characterising a double stranded target polynucleotide comprising (a) a hairpin loop capable of linking the two strands of the target polynucleotide at one end and (b) one or more species which control or decrease the formation of secondary structure by the target polynucleotide; and
an apparatus for sequencing a target polynucleotide, comprising: (a) a plurality of membranes; (b) a plurality of transmembrane pores in the membranes; and (c) conditions on the other side of the pores from which the pores are contacted with the polynucleotide which are capable of controlling the formation of secondary structure by the target polynucleotide.

DESCRIPTION OF THE FIGURES

FIG. 5 shows an example current trace (y-axis label=Current (pA), x-axis label=Time(s)) of when a helicase (T4 Dda 1993-(E94C/A360C)) controlled the cis to trans translocation of the DNA construct 1 through an MspA nanopore with a single stranded DNA (AE182) present on the trans side of the membrane. The lower picture is a zoomed in version of the upper one. The region labelled A corresponds to the template (DNA sequence 1). The regions labelled B1 and B2 correspond to the complement (DNA sequence 2). The region labelled C corresponds to the hairpin (DNA sequence 4). In this figure, the complement initially has a higher current range and speed to the template (B1) and then changes to a behaviour where the current range and speed are similar to the template (B2), then goes back to the initial behaviour (B1). The AE182 strand was designed to hybridise to a region in the middle of the template region of construct 1. This data shows that the AE182 controls the formation of secondary structure in the region of construct 1 to which it hybridises.

FIG. 6 shows data acquired by observing helicase (T4 Dda 1993-(E94C/A360C)) controlled translocation of the DNA construct 1 through an MspA nanopore, and categorising the helicase controlled DNA movements into one of the three categories: uplift, no uplift or delayed uplift. The trans DNA (Col 1) and conc. columns (Col 2) show what was present in the trans chamber (the side of the nanopore opposite to which the target polynucleotide was added) in addition to buffer 1.

Figure 1:
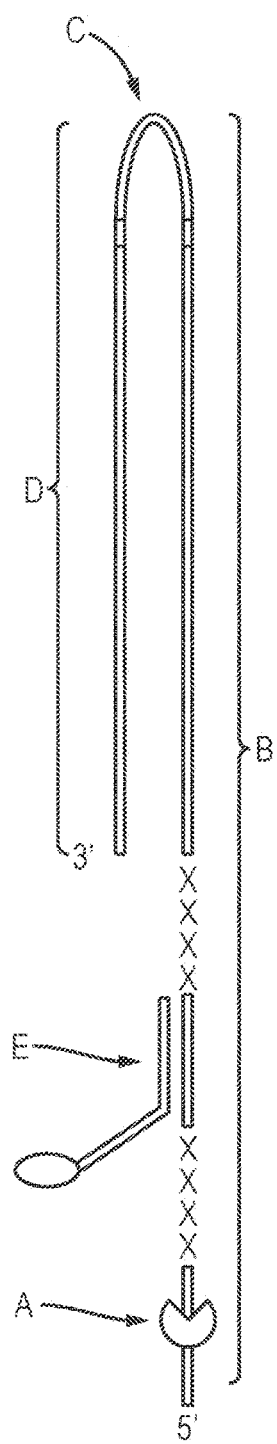
FIG. 1 shows a schematic of construct 1 where A is a helicase (T4 Dda 1993-(E94C/A360C) (SEQ ID NO: 24 with mutations E94C/A360C and then (AMI) G1G2 (where (AMI) G1G2=deletion of MI and then addition G1 and G2)) bound on the indicated region of DNA sequence 1 (B) which is hybridised to DNA sequence 2 (D) and DNA sequence 3 (E). DNA sequence 1 is also attached to DNA sequence 2 with a ligated hairpin. DNA sequence 4 (C).

It is to be understood that Figures are for the purpose of illustrating particular embodiments of the invention only, and are not intended to be limiting.

DESCRIPTION OF THE SEQUENCE LISTING

SEQ ID NO: 1 shows the codon optimised polynucleotide sequence encoding the MS-B1 mutant MspA monomer. This mutant lacks the signal sequence and includes the following mutations: D90N, D91N, D93N, D118R, D134R and E139K.

SEQ ID NO: 2 shows the amino acid sequence of the mature form of the MS-B1 mutant of the MspA monomer. This mutant lacks the signal sequence and includes the following mutations: D90N, D91N, D93N, D118R. D134R and E139K.

SEQ ID NO: 3 shows the polynucleotide sequence encoding one monomer of α-hemolysin-E11IN/K147N (α-HL-NN; Stoddart et al., PNAS, 2009; 106 (19): 7702-7707).

SEQ ID NO: 4 shows the amino acid sequence of one monomer of α-HL-NN.

SEQ ID NOs: 5 to 7 show the amino acid sequences of MspB, C and D.

SEQ ID NO: 8 shows the polynucleotide sequence encoding the Phi29 DNA polymerase.

SEQ ID NO: 9 shows the amino acid sequence of the Phi29 DNA polymerase.

SEQ ID NO: 10 shows the codon optimised polynucleotide sequence derived from the sbcB gene from *E. coli*. It encodes the exonuclease I enzyme (EcoExo I) from *E. coli*.

SEQ ID NO: 11 shows the amino acid sequence of exonuclease I enzyme (EcoExo I) from *E. coli*.

SEQ ID NO: 12 shows the codon optimised polynucleotide sequence derived from the xthA gene from *E. coli*. It encodes the exonuclease III enzyme from *E. coli*.

SEQ ID NO: 13 shows the amino acid sequence of the exonuclease III enzyme from *E. coli*. This enzyme performs distributive digestion of 5' monophosphate nucleosides from one strand of double stranded DNA (dsDNA) in a 3'-5' direction. Enzyme initiation on a strand requires a 5' overhang of approximately 4 nucleotides.

SEQ ID NO: 14 shows the codon optimised polynucleotide sequence derived from the rec gene from *T. thermophilus*. It encodes the RecJ enzyme from *T. thermophilus* (TthRecJ-cd).

SEQ ID NO: 15 shows the amino acid sequence of the RecJ enzyme from *T. thermophilus* (TihRecJ-cd). This enzyme performs processive digestion of 5' monophosphate nucleosides from ssDNA in a 5'-3' direction. Enzyme initiation on a strand requires at least 4 nucleotides.

SEQ ID NO: 16 shows the codon optimised polynucleotide sequence derived from the bacteriophage lambda exo (redX) gene. It encodes the bacteriophage lambda exonuclease.

SEQ ID NO: 17 shows the amino acid sequence of the bacteriophage lambda exonuclease. The sequence is one of three identical subunits that assemble into a trimer. The enzyme performs highly processive digestion of nucleotides from one strand of dsDNA, in a 5'-3'direction (www.neb.com/nebecomm/products/productM0262.asp). Enzyme initiation on a strand preferentially requires a 5' overhang of approximately 4 nucleotides with a 5' phosphate.

SEQ ID NO: 18 shows the amino acid sequence of Hel308 Mbu.

SEQ ID NO: 19 shows the amino acid sequence of Hel308 Csy.

SEQ ID NO: 20 shows the amino acid sequence of Hel308 Tga.

SEQ ID NO: 21 shows the amino acid sequence of Hel308 Mhu.

SEQ ID NO: 22 shows the amino acid sequence of Tral Eco.

SEQ ID NO: 23 shows the amino acid sequence of XPD Mbu.

SEQ ID NO: 24 shows the amino acid sequence of Dda 1993.

SEQ ID NO: 25 shows the amino acid sequence of Trwc Cba.

SEQ ID NO: 26 shows the codon optimised polynucleotide sequence encoding the wild-type CsgG monomer from *Escherichia coli* Str. K-12 substr. MC4100. This monomer lacks the signal sequence.

SEQ ID NO: 27 shows the amino acid sequence of the mature form of the wild-type CsgG monomer from *Escherichia coli* Str. K-12 substr. MC4100. This monomer lacks the signal sequence. The abbreviation used for this CsgG=CsgG-Eco.

SEQ ID NO: 28 is DNA sequence 1 used in Example 1.
SEQ ID NO: 29 is DNA sequence 2 used in Example 1.
SEQ ID NO: 30 is an alternative DNA sequence 1 that could be used in Example 1.
SEQ ID NO: 31 is an alternative DNA sequence 2 that could be used in Example 1.
SEQ ID NO: 32 is DNA sequence 3 used in Example 1.
SEQ ID NO: 33 is DNA sequence 4 used in Example 1.
SEQ ID NO: 34 is the DNA sequence of AE202 used in Example 1.
SEQ ID NO: 35 is the DNA sequence of AE186 used in Example 1.
SEQ ID NO: 36 is the DNA sequence of TE60 used in Example 1.
SEQ ID NO: 37 is an alternative DNA sequence of TE60.
SEQ ID NO: 38 is the DNA sequence of AE203 used in Example 1.
SEQ ID NO: 39 is the DNA sequence of AE210 used in Example 1.
SEQ ID NO: 40 is the DNA sequence of AE191 used in Example 1.
SEQ ID NO: 41 is the DNA sequence of AE192 used in Example 1.
SEQ ID NO: 42 is the DNA sequence of AE193 used in Example 1.
SEQ ID NO: 43 is the DNA sequence of AE263 used in Example 1.
SEQ ID NO: 44 is the DNA sequence of AE264 used in Example 1.
SEQ ID NO: 45 is the DNA sequence of AE265 used in Example 1.
SEQ ID NO: 46 is the DNA sequence of AE266 used in Example 1.
SEQ ID NO: 47 is the DNA sequence of AE267 used in Example 1.
SEQ ID NO: 48 is the DNA sequence of AE268 used in Example 1.
SEQ ID NO: 49 is the DNA sequence of AE269 used in Example 1.
SEQ ID NO: 50 is the DNA sequence of AE270 used in Example 1.
SEQ ID NO: 51 is the DNA sequence of AE271 used in Example 1.
SEQ ID NO: 52 is the DNA sequence of AE272 used in Example 1.
SEQ ID NO: 53 is the DNA sequence of AE273 used in Example 1.
SEQ ID NO: 54 is the DNA sequence of AE274 used in Example 1.
SEQ ID NO: 55 is the DNA sequence of AE275 used in Example 1.
SEQ ID NO: 56 is the DNA sequence of AE276 used in Example 1.
SEQ ID NO: 57 is the DNA sequence of AE277 used in Example 1.
SEQ ID NO: 58 is the DNA sequence of AE278 used in Example 1.
SEQ ID NO: 59 is the DNA sequence of AE279 used in Example 1.
SEQ ID NO: 60 is the DNA sequence of AE280 used in Example 1.

SEQ ID NO: 61 is the DNA sequence of AE281 used in Example 1.
SEQ ID NO: 62 is the DNA sequence of AE282 used in Example 1.
SEQ ID NO: 63 is the DNA sequence of AE283 used in Example 1.
SEQ ID NO: 64 is the DNA sequence of AE284 used in Example 1.
SEQ ID NO: 65 is the DNA sequence of AE285 used in Example 1.
SEQ ID NO: 66 is the DNA sequence of AE286 used in Example 1.
SEQ ID NO: 67 is the DNA sequence of AE287 used in Example 1.
SEQ ID NO: 68 is the DNA sequence of AE288 used in Example 1.
SEQ ID NO: 69 is the DNA sequence of AE289 used in Example 1.
SEQ ID NO: 70 is the DNA sequence of AE290 used in Example 1.
SEQ ID NO: 71 is the DNA sequence of AE291 used in Example 1.
SEQ ID NO: 72 is the DNA sequence of AE292 used in Example 1.
SEQ ID NO: 73 is the DNA sequence of AE258 used in Example 1.
SEQ ID NO: 74 is the DNA sequence of AE259 used in Example 1.
SEQ ID NO: 75 is the DNA sequence of AE182 used in Example 1.
SEQ ID NO: 76 is the DNA sequence of TH14 used in Example 3.
SEQ ID NO: 77 is the DNA sequence of TH15 used in Example 3.
SEQ ID NO: 78 is the DNA sequence of TH16 used in Example 3.
SEQ ID NO: 79 is the DNA sequence of TH17 used in Example 3.
SEQ ID NO: 80 is the DNA sequence of a control hairpin used in Example 3.
SEQ ID NO. 81 is the DNA sequence of Y adaptor sequence 1 used in Example 3.
SEQ ID NO: 82 is the DNA sequence of Y adaptor sequence 2 used in Example 3.
SEQ ID NO: 83 is the DNA sequence of Y adaptor sequence 3 used in Example 3.

It is to be understood that sequences are not intended to be limiting.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a polynucleotide" includes two or more polynucleotides, reference to "an anchor" refers to two or more anchors, reference to "a helicase" includes two or more helicases, and reference to "a transmembrane pore" includes two or more pores and the like.

In this specification, where different amino acids at a specific position are separated by the symbol "/", the/symbol "/" means "or". For instance. P108R/K means P108R or P108K. In this specification where different positions or different substitutions are separated by the symbol "/", the "/" symbol means "and". For example, E94/P108 means E94 and P108 or E94D/P108K means E94D and P108K.

All publications, patents and patent applications cited herein, whether supra or infra, are hereby incorporated by reference in their entirety.

Methods of the Invention

The invention provides an improved method of characterising a target polynucleotide. The target polynucleotide is contacted with one side of a transmembrane pore in a membrane. The target polynucleotide is also contacted with a molecular brake which controls the movement of the target polynucleotide through the pore. Suitable pores, membranes and molecular brakes are discussed in more detail below. One or more measurements which are indicative of one or more characteristics of the target polynucleotide are taken as the polynucleotide moves with respect to the pore. An important part of the invention is that conditions on the other side of the pore (i.e. the other side of the pore from the one side of the pore with which the target polynucleotide is contacted) control the formation of secondary structure by the target polynucleotide on this other side of the pore. In other words. the conditions on the other side of the pore are selected to control the formation of secondary structure by the target polynucleotide after it has moved through the pore. Control of the formation of secondary structure may comprise controlling the extent and/or increasing the consistency to which the secondary structure is formed. Formation of secondary structure can be a random and variable process and control of the extent of formation and/or increasing the consistency of formation of secondary structure lowers the variability or randomness of formation. This can give rise to an improved measurement accuracy as further described below.

It may, for example, be desirable to increase formation of secondary structure such that strong (GC) vs weak (AT) interactions may be distinguished. Since formation of secondary structure can be detected as part of the current trace, sequence specific information could be extracted by doing this. For example, the signal can be used to empirically measure secondary structures that may be hard to measure by conventional means. As a particular example, the signal could be used to empirically measure the presence of such structures G-quadraplex formation.

Another situation in which it is desirable to increase formation of secondary structure is where there is Inconsistent behavior within a strand, giving rise to inconsistent signal. An inconsistent signal is hard to model and therefore can produce lower accuracy base calling. It may therefore be preferable to have a consistent uplifted signal from consistent formation of the secondary structure where the alternative is an inconsistent signal.

The conditions include, for example, voltage, salt type, salt concentration, temperature, presence of DNA and/or pH. Changing any one or more of these conditions will affect polynucleotide hybridization/secondary structures.

Secondary structure formation may be detected and measured by any suitable means. For example, by subjecting a polynucleotide to the condition to be tested and running a melt curve assay using standard procedures known in the art. Secondary structure formation may alternatively be detected and measured by measuring the frequency and magnitude of the uplifted/non-uplifted signal changes as a polynucleotide passing through a nanopore as described in the Examples. The conditions may be selected to control the formation of secondary structure by or in the target polynucleotide in any way and to any extent. The conditions may decrease, reduce or prevent the formation of secondary structure. The conditions may decrease, reduce or prevent the formation of secondary structure by any amount, such by at least 10%, at least 20%, at least 30%, at least 40%, at least 50%, at least 60%, at least 70%, at least 80% or at least 90%. The decrease, reduction or prevention of secondary structure formation is typically compared to a reference condition. The method more preferably abolishes the formation of secondary structure (i.e. decreases, reduces or prevents it by 100%).

Alternatively, the conditions may increase the formation of secondary structure. The conditions may increase the formation of secondary structure by any amount, such by at least 10%, at least 20%, at least 30%, at least 40%, at least 50%, at least 60%, at least 70%, at least 80% or at least 90%. The increase of secondary structure formation is typically compared to a reference condition. The method may increase the formation of secondary structure by at least twofold, at least threefold, at least fourfold, at least fivefold, at least tenfold, at least twentyfold, at least thirty fold, at least fortyfold, at least fiftyfold, at least one hundredfold, at least five hundredfold or one thousandfold.

The skilled person would readily be able to determine a suitable reference condition depending on the condition being altered to control secondary structure formation. For example, where the condition is the presence of DNA, the reference condition is the absence of the DNA. A typical reference condition is 150 mM potassium ferricyanide. 150 mM potassium ferrocyanide. 25 mM potassium phosphate. pH8 at 34° C.

For any one strand there is a probability that sequence dependent secondary structure will form (0-100% probability, more precisely close to zero to 100% probability, i.e. <1% to 100% probability). The probability depends on the physical characteristics of a given sequence, including length, sequence, and possibly other factors such as methylation and/or damage. Moreover, for any given sequence a variety of structural elements may form, each with a probability dependent on conditions (total probability of all forms adding up to 100%). For example a given sequence may form: 1) approximately linearized unstructured ssDNA/ssRNA at 20% probability: 2) secondary structure A at 40% probability: 3) secondary structure B at 30% probability; and 4) secondary structure C at 10% probability. Secondary structures A. B and C are different secondary structure conformations. Various secondary structure conformations are known in the art and include, for example, stem loops, hairpins, triplex DNA, pseudoknots, quadruplex structures etc. The formation of secondary structure may be measured in any known way.

"Uplift" is a term used to describe an increase in the current range of a polynucleotide hairpin strand passing through a nanopore from the cis side of a membrane to the trans side of the membrane. It occurs when the second (complement) strand of a double stranded polynucleotide is passing through the nanopore and the first (template) strand of a double stranded polynucleotide is in the trans. Uplift may be observed as an increase in complement signal relative to template signal.

"No uplift" is identified when the current range when the first (template) strand of a double stranded polynucleotide is translocating through a pore is similar, or substantially similar (e.g., the same) as the current range when the second (complement) strand of a double stranded polynucleotide is translocating through the pore. "Non uplift" may be observed when the complement signal is approximately the same as the template signal.

Current range is the difference in current between the lowest levels and highest levels in the signal. This can be defined many ways. e.g. current range=Max current-min current, or range=95th percentile-5th percentile.

Increased current range is said to occur when it can be observed above any normal signal noise/variation. e.g. in the order of >5% or >10%.

Delayed uplift shows that secondary structure is a time-bound variable and inconsistent process, that can occur either immediately as the complement starts exiting the pore, or some time later. In other words "delayed uplift" is when "no uplift" behavior becomes an "uplift" behavior. Mechanistically, delayed uplift occurs when the trans secondary structures that cause the shift in signal did not for some reason immediately form as the second strand of a double stranded polynucleotide starts exiting the trans exit of pore, however, some period later part way through the transit of the second strand, the trans hybridization/secondary structure does occur and the signal shifts to "uplifted". This is an example of the intra-strand inconsistent behavior.

Accuracy at both the single-molecule level and consensus pile-up level can be improved by increasing the extent and/or consistency of the formation of both the known structural elements (e.g. rehybridisation of the complementary strand of dsDNA/dsRNA) or random structural elements (sequence dependent regions that may form one or more than one type of structural element). Secondary structure affects nanopore discrimination and enzyme movement. Basecalling accuracy is fundamentally dependent on learning the underlying discrimination and movement behaviours, so if there are more varieties of behaviour to learn, the algorithm has to be more complex. As complexity and choices increase there is more chance of making an error. Alternatively, an algorithm may learn average behaviour, which does not perfectly describe the variety of true underlying behaviours, and is therefore inherently less accurate. Accuracy can be increased by reducing the absolute number of variable processes (random formation of expected or unexpected structural elements) or reducing the probability that alternative processes can form (e.g. ideally making one process dominant, most preferably above 50%, above 60%, above 70%, above 80%, above 90% or 100%). Increasing consistency may therefore result in the reduction of the number of different secondary structure types that can form, or increase the probability of occurrence of one type of process, or decrease the probability of occurrence of an alternative process.

The method of characterising a target polynucleotide may comprise: (a) providing a transmembrane pore in a membrane, wherein the membrane defines a first side and a second side, wherein the second side provides a condition that controls formation of a secondary structure from a portion of the target polynucleotide that moves through the transmembrane pore to the second side: (b) adding the target polynucleotide and a molecular brake to the first side, wherein the molecular brake binds to the target polynucleotide and controls the movement of the target polynucleotide through the pore; and (c) measuring one or more physical parameters that are indicative of one or more characteristics of the target polynucleotide as the target polynucleotide moves through the transmembrane pore.

Random Secondary Structure

The selected conditions preferably control the extent and/or consistency of formation of random secondary structure by the target polynucleotide on the other side of the pore. The conditions may decrease, reduce or prevent the formation of random secondary structure. The conditions may increase the formation of random secondary structure. The formation of random secondary structure may be decreased, reduced, prevented or increased by any of the amounts discussed above.

Random secondary structures are secondary/tertiary structures in a polynucleotide that are in thermal equilibrium under the running conditions of the method. Random secondary structures can either be totally unformed, partially formed, or fully formed at any one time, and therefore at the moment of measurement as the polynucleotide passes through a transmembrane pore. Adjusting the conditions of the system as described herein will alter the balance between unformed and fully formed secondary/tertiary structures.

The random secondary structure preferably comprises (a) one or more helices, (b) one or more loops, (c) one or more pseudoknots, (d) one or more quadruplexes or (e) a combination thereof. In (e), the random secondary structure preferably comprises {a}; {b}; {c}; {d}; {a,b}; {a,c}; {a,d}; {b,c}; {b,d}; {c,d}; {a,b,c}; {a,b,d}; {a,c,d}; {b,c,d}; or {a,b,c,d} In any of (a) to (d), the random secondary structure may comprise any number of helices, loops, pseudoknots or quadruplexes, such as 2 or more, 3 or more, 4 or more, 5 or more, 10 or more, 20 or more, 50 or more, 100 or more, 500 or more, 1000 or more or 5000 or more.

The one or more helices in (a) may be any length. For example, the helices may comprise 2 or more, 3 or more, 4 or more, 5 or more, 10 or more, 20 or more, 50 or more, 100 or more or 500 or more nucleotides, and/or up to about 1000 or less, 500 or less. 100 or less, 50 or less, 10 or less or 5 or less nucleotides.

The one or more loops in (b) preferably comprise (i) one or more stem loops, (ii) one or more tetraloops. (iii) one or more hairpin loops or (iv) any combination thereof. In (iv), the one or more loops may comprise {i}; {i}; {iii}; {i,ii}; {i,iii}, {ii, iii}; or {i,ii,iii,iv}. There may be any number of loops as discussed above. Stem loops are known in the art and may be any length. For example, the loops may comprise 2 or more, 3 or more, 4 or more, 5 or more, 10 or more, 20 or more, 50 or more, 100 or more or 500 or more nucleotides, and/or up to about 1000 or less, 500 or less, 100 or less, 50 or less. 10 or less or 5 or less nucleotides.

Hairpin loops are discussed in more detail below. Tetraloops are four-base hairpin loop motifs in RNA secondary structure that cap many double helices. There are many variants of the tetraloop, the published examples of which include ANYA, CUYG, GNRA, UMAC and UNCG.

The one or more pseudoknots in (c) may be any of those known in the art. A pseudoknot is a polynucleotide structure containing at least two stem loop structures in which half of one stem is intercalated between the two halves of another stem.

The one or more quadruplexes in (d) may be any of those known in the art. The one or more quadruplexes may be any type of quadruplex. The one or more quadruplexes may be one or more intermolecular quadrupleves, such as bimolecular quadruplexes or tetramolecular quadruplexes. The one or more quadruplexes are preferably intramolecular quadruplexes.

The one or more quadruplexes are preferably G-quadruplexes (also known as G-tetrads or G4-DNA). These are polynucleotide sequences that are rich in guanine and are capable of forming a four-stranded structure. Four guanine bases can associate through Hoogsteen hydrogen bonding to form a square planar structure called a guanine tetrad, and two or more guanine tetrads can stack on top of each other to form a G-quadruplex. The quadruplex structure is further stabilized by the presence of a cation, especially potassium, which sits in a central channel between each pair of tetrads. Forming G-quadruplexes is well known in the art (Marathias and Bolton, Nucleic Acids Research, 2000: 28 (9): 1969-1977: Kankia and Marky. J. Am. Chem. Soc. 2001, 123, 10799-10804; and Marusic et al., Nucleic Acids Research, 2012, 1-11). The one or more quadruplexes more preferably comprises the sequence Ga followed by Nb followed by Gc followed by Nd followed by Ge followed by Nf followed by Gg, wherein G is a nucleotide comprising guanine, wherein a, c, e and g are independently selected from 1, 2, 3, 4 and 5, wherein N is any nucleotide and wherein b, d and f are from 2 to 50. The values of a, c, e and g may be identical. G is preferably guanosine monophosphate (GMP), cyclic guanosine monophosphate (cGMP), deoxyguanosine monophosphate (dGMP), dideoxyguanosine monophosphate. N2-methyl-GMP. N2-methyl-cGMP, N2-methyl-dGMP. N2-methyl-dideoxyguanosine monophosphate. N2-methyl-06-methyl-GMP, N2-methyl-06-methyl-cGMP, N2-methyl-06-methyl-dGMP, N2-methyl-06-methyl-dideoxyguanosine monophosphate, 2'-O-methyl-GMP, 2-O-methyl-cGMP, 2'-O-methyl-dGMP, 2-O-methyl-dideoxyguanosine monophosphate, 6-thio-GMP. 6-thio-cGMP, 6-thio-dGMP. 6-thio-dideoxyguanosine monophosphate, 7-methyl-GMP, 7-methyl-cGMP, 7-methyl-dGMP, 7-methyl-dideoxyguanosine monophosphate, 7-deaza-GMP, 7-deaza-cGMP, 7-deaza-dGMP, 7-deaza-dideoxyguanosine monophosphate. 8-oxo-GMP, 8-oxo-CGMP, 8-oxo-dGMP or 8-oxo-dideoxyguanosine monophosphate.

The formation of random secondary structure on the other side of the pore can cause the polynucleotide to pull on the molecular brake and interfere with its function. The conditions may decrease, reduce or prevent the formation of random secondary structure on the other side of the pore and maintain the function of the molecular brake. The method preferably allows the molecular brake to display reduced forward slipping. This is a phenomenon where the polynucleotide moves forwards relative to the pore by at least 4 consecutive nucleotides and typically by more than 10 consecutive nucleotides. Slipping forward may involve movement forward of 100 consecutive nucleotides or more and this may happen more than once for each polynucleotide Slipping forward can be problematic for polynucleotide sequencing.

The method preferably reduces the frequency of forward slipping displayed by the helicase by at least 10%, at least 20%, at least 30%, at least 40%, at least 50%, at least 60%, at least 70%, at least 80% or at least 90%. The reduction in frequency of slipping is typically compared to a reference condition. A typical reference condition is 150 mM potassium ferricyanide. 150 mM potassium ferrocyanide. 25 mM potassium phosphate, pH8 at 34° C. The method more preferably abolishes forward slipping. i.e. reduces the frequency of forward slipping displayed by the molecular brake by 100%. The method preferably reduces the length of forward slipping displayed by the molecular brake to 10 nucleotides or fewer, such as 9 nucleotides or fewer. 8 nucleotides or fewer, 7 nucleotides or fewer, 6 nucleotides or fewer. S nucleotides or fewer. 4 nucleotides or fewer, 3 nucleotides or fewer, 2 nucleotides or fewer, or 1 nucleotide. The method preferably reduces the frequency and length of forward slipping displayed by the molecular brake.

Forward slipping can be measured using any method known in the art. The ability of a molecular brake to control the movement of a polynucleotide and the incidence of forward slipping is typically as saved in a nanopore system, such as the ones described below.

Figure 3:
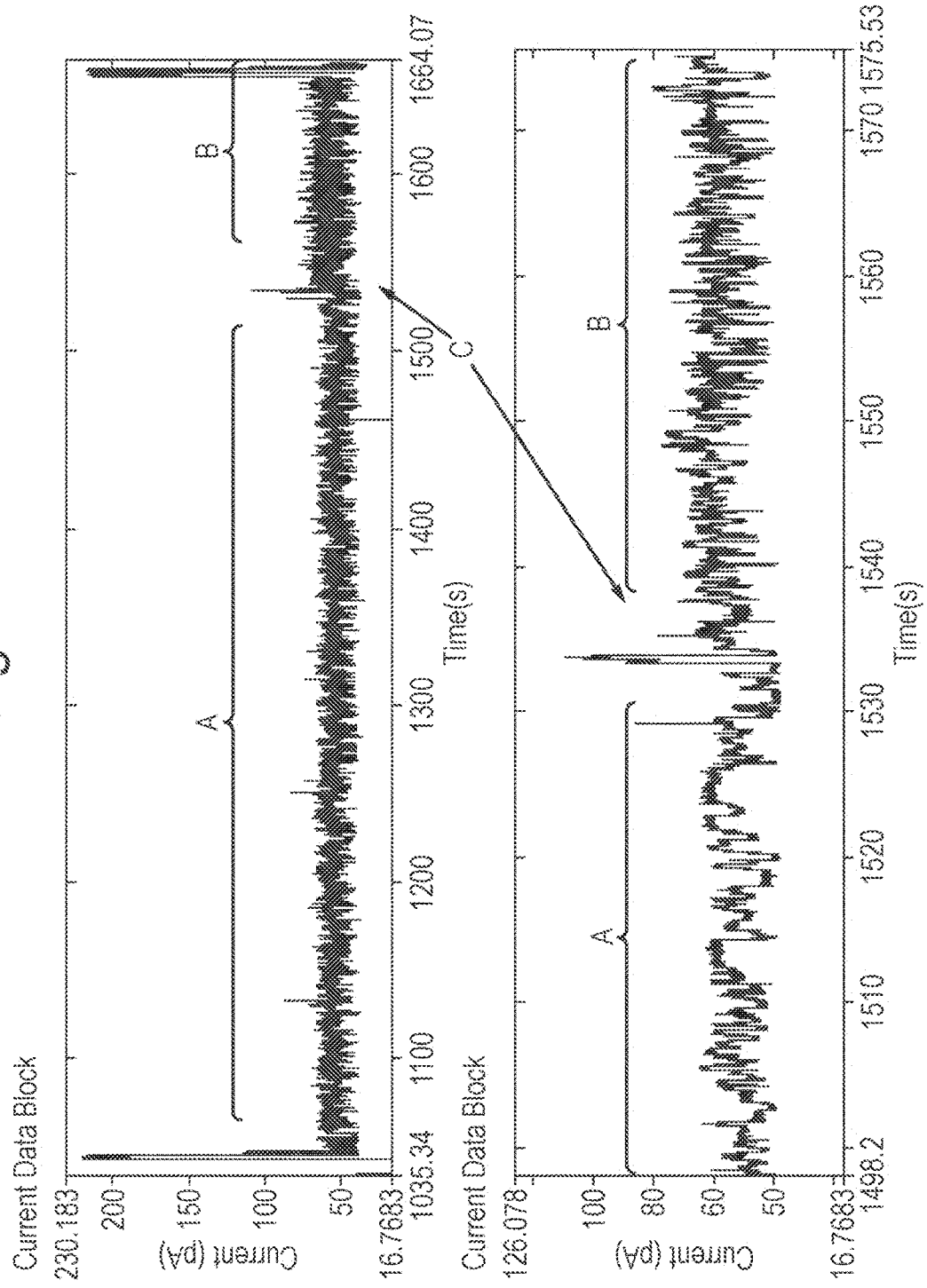
FIG. 3 shows an example current trace (y-axis label=Current (pA), x-axis label=Time(s)) of when a helicase (T4 Dda 1993-(E94C/A360C)) controlled the translocation of the DNA construct 1 through an MspA nanopore. The lower picture is a zoomed in version of the upper one. The region labelled A corresponds to the template (DNA sequence 1). The region labelled B corresponds to the complement (DNA sequence 2). The region labelled C corresponds to the hairpin (DNA sequence 4). In this figure, the complement has a higher current range than the template, the duration is shorter and the speed is faster. This is an example of helicase controlled DNA movement exhibiting Uplift.

The method typically concerns reducing the formation of random secondary structure on the other side of the pore. This may reduce the phenomenon of uplift. Secondary structure formation on the other side of the pore, such as the formation of random secondary structure or the rehybrisation of the two strands of a double stranded target polynucleotide, applies a force to the polynucleotide, which is transmitted through to the sections of polynucleotide in the pore and through to the molecular brake. This may be observed by a change in the charaterisation measurements taken as the polynucleotide in the pore. With rehybrisation, the phenomenon typically manifests itself as an increase in current (typically average current) flowing through the pore when the complement sequence (the second strand) moves through the pore relative to the template sequence (first strand) and an increase in the characterisation current range. This can easily be seen by eye (see B versus A in FIG. 3). Hence, the phenomenon has been termed "uplift". Uplift not only involves an increase in current range, but also typically involves an increased speed of movement of the complement sequence through the pore compared with the template sequence such that the duration of its characterisation is reduced. In addition to rehybridisation, the formation of random secondary structure on the other side of the pore can also lead to uplift, albeit typically to a smaller degree and in a random manner. Uplift (or more specifically a shift in discrimination relative to ssDNA with no secondary structure passing through pore) is not limited to the complement. Uplift can occur in a target polynucleotide (e.g. DNA/RNA) if random structural elements form, for example: loops, hairpins, quadruplexes. Conversely, if uplift forms in a complement strand that is fully hybridising on the other side of the pore, there can still be "non-uplifted" regions due to structural elements (e.g. quadruplexes) that disrupt the perfect hybridisation on the other side of the pore.

Single stranded polynucleotides (e.g. DNA) with no ability to form secondary or tertiary structure is generally the baseline signal. The ability to form secondary or tertiary structure is not limited to two template-complement hybridized polynucleotides, it can form in single stranded DNA or single stranded RNA, e.g. Hairpin loops or quadruplexes. Therefore, as a template polynucleotide strand passes through a pore, secondary/tertiary structural elements can form that shift the signal. The formation of the structures can be inconsistent as they are stochastic, creating a random element to the signal that is difficult to model and can reduce basecalling accuracy. This occurs when sequencing two strands of a double stranded polynucleotide joined by a hairpin and can also occur when sequencing a single strand of a double stranded nucleotide.

In a case where uplift occurs when a complement strand exiting the pore is hybridizing to a template strand on the other side of the pore in an "ideal" manner (i.e. Where there are no mismatches in the annealing), the signal can change back to "non-uplifted" if the "ideal" template-complement hybridization is disrupted, for example by other structural elements (e.g. a quadruplex structure) or by DNA damage.

Reduction of the formation of random secondary structure on the other side of the pore may therefore reduce random uplift. If the target polynucleotide is double stranded as discussed in more detail below, reducing the formation of random secondary structure on the other side of the pore may not necessarily reduce the uplift caused by rehybridisation. It may, however, make the rehybridisation of the two strands of the target polynucleotide on the other side of the pore more consistent and hence the uplift more consistent. Consistency facilitates the characterisation of the target polynucleotide because the uplift can be better predicted and accounted for.

The method may involve increasing the formation of random secondary structure on the other side of the pore. Although this may affect the random uplift caused by the formation of the random secondary structure itself, it may also to prevent the two strands of a double stranded target polynucleotide from rehybridising on the other side of the pore and thereby prevent the large uplift caused by such rehybridisation. This is discussed in more detail below. The changes in signal can be used to determine various characteristics of the polynucleotide, including but not limited to GC content, damage, modified bases and/or quadruplexes. If the behavior is random with <100% probability of formation, then combined information from a consensus pile-up of many separate strands/molecules can be used to determine the underlying properties Increasing the chance of the signal change makes the features easier to measure and requires less coverage in a consensus pile-up.

Rehybridisation

In preferred embodiments, the target polynucleotide is double stranded. In such embodiments, the method preferably comprises providing a construct comprising the target polynucleotide in which the two strands of the target polynucleotide are linked at one end of the target polynucleotide by a hairpin loop. The method more preferably comprises the step of linking the two strands of the target polynucleotide at one end of the target polynucleotide by a hairpin loop to provide a construct comprising the target polynucleotide. These steps are discussed in more detail below. The construct is contacted with one side of a transmembrane pore in a membrane and a molecular brake which separates the two strands of the construct and controls the movement of the construct through the pore one strand at a time. One or more measurements are taken which are indicative of one or more characteristics of the target polynucleotide as the construct moves with respect to the pore.

Suitable hairpin loops can be designed using methods known in the art. Hairpin loops typically comprise a stem region formed from the hybridisation of two parts of the hairpin loop and a loop region. The loop region typically does not comprise any hybridisation.

The hairpin loop may be any length. The hairpin loop is typically 110 or fewer nucleotides, such as 100 or fewer nucleotides, 90 or fewer nucleotides, 80 or fewer nucleotides. 70 or fewer nucleotides, 60 or fewer nucleotides, 50 or fewer nucleotides, 40 or fewer nucleotides, 30 or fewer nucleotides, 20 or fewer nucleotides or 10 or fewer nucleotides, in length. The hairpin loop is preferably from about 1 to 110, from 2 to 100, from 5 to 80 or from 6 to 50 nucleotides in length. Longer lengths of the hairpin loop, such as from 50 to 110 nucleotides, are preferred if the loop is involved in the differential selectability of the adaptor. Similarly, shorter lengths of the hairpin loop, such as from 1 to 5 nucleotides, are preferred if the loop is not involved in the selectable binding as discussed below. The stem region may be any length. Typically, the stem region has a length of from about 4 to about 10 bases up to about 100, 1000, 10000, 100000 or 1000000 bases.

The hairpin loop may be provided at either end of the polynucleotide, i.e. the 5' or the 3' end. The hairpin loop may be ligated to the polynucleotide using any method known in the art. The hairpin loop may be ligated using a ligase, such as T4 DNA ligase, *E. coli* DNA ligase. Taq DNA ligase. Tma DNA ligase and 9°N DNA ligase.

The two strands of the polynucleotide may be separated using any method known in the art. For instance, they may be separated by a molecular brake, such as a polynucleotide binding protein, or using conditions which favour dehybridsation (examples of conditions which favour dehybridisation include, but are not limited to, high temperature, high pH and the addition of agents that can disrupt hydrogen bonding or base pairing, such as formamide and urea).

The hairpin loop preferably comprises a selectable binding moiety. This allows the polynucleotide to be purified or isolated. A selectable binding moiety is a moiety that can be selected on the basis of its binding properties. Hence, a selectable binding moiety is preferably a moiety that specifically binds to a surface. A selectable binding moiety specifically binds to a surface if it binds to the surface to a much greater degree than any other moiety used in the invention. In preferred embodiments, the moiety binds to a surface to which no other moiety used in the invention binds.

Suitable selective binding moieties are known in the art. Preferred selective binding moieties include, but are not limited to, biotin, a polynucleotide sequence, antibodies, antibody fragments, such as Fab and ScSv, antigens, polynucleotide binding proteins, poly histidine tails and GST tags. The most preferred selective binding moieties are biotin and a selectable polynucleotide sequence. Biotin specifically binds to a surface coated with avidins. Selectable polynucleotide sequences specifically bind (i.e. hybridise) to a surface coated with homologus sequences. Alternatively, selectable polynucleotide sequences specifically bind to a surface coated with poly nucleotide binding proteins.

The hairpin loop and/or the selectable binding moiety may comprise a region that can be cut, nicked, cleaved or hydrolysed. This allows the hairpin loop to be selectively cleaved on the other side of the pore as discussed in more detail below. Such a region can be designed to allow the polynucleotide to be removed from the surface to which it is bound following purification or isolation. Suitable regions are known in the art. Suitable regions include, but are not limited to, an RNA region, a region comprising desthiobiotin and streptavidin, a disulphide bond and a photocleavable region.

The conditions on the other side of the pore control the formation of secondary structure by the target polynucleotide on the other side of the pore. The conditions preferably control the ability of the two strands of the target polynucleotide to rehybridise on the other side of the pore. The conditions preferably control the formation of random secondary structure by the target polynucleotide on the other side of the pore. The conditions preferably control the ability of the two strands of the target polynucleotide to rehybridise on the other side of the pore and control the formation of random secondary structure by the target polynucleotide on the other side of the pore. The conditions more preferably reduce the ability of the two strands of the target polynucleotide to rehybridise on the other side of the pore by increasing the formation of random secondary structure by the target polynucleotide on the other side of the pore. The control of the formation of random secondary structure is discussed above.

The conditions may decrease, reduce or prevent the ability of the two strands of the target polynucleotide to rehybridise on the other side of the pore. The conditions may prevent the two strands of the target polynucleotide from rehybridising on the other side of the pore. The method may involve increasing the formation of random secondary structure on the other side of the pore to prevent or stop the strands of a double stranded target polynucleotide from rehybridising on the other side of the pore. This is advantageous because it reduces or abolishes the phenomenon of uplift as discussed above.

The conditions may increase the ability of the two strands of the target polynucleotide to rehybridise on the other side of the pore. The rehybridisation may be decreased, reduced, prevented or increased by any of the amounts discussed above. Increasing the rehybridisation may make uplift more consistent or predictable.

Methods of Controlling Secondary Structure and or Rehybridisation

The conditions preferably comprise one or more species on the other side of the pore which control or decrease the formation of secondary structure by the target polynucleotide. The one or more species may control or decrease the formation of random secondary structure as described above. The one or more species may control or decrease the ability of the two strands of the target polynucleotide to rehybridise.

The one or more species preferably comprise (i) one or more control polynucleotides which hybridise with the target polynucleotide and/or the hairpin loop. The conditions preferably comprise (i) a plurality of control polynucleotides which hybridise with the target polynucleotide and/or the hairpin loop. The conditions may comprise any number of control polynucleotides, such as 2, 5, 10, 20, 50, 100, 500, 1000, 5000 or 10,000 or more. The one or more controlled polynucleotides may be formed from any of the polynucleotides discussed below.

The one or more control polynucleotides preferably comprise universal nucleotides. A universal nucleotide is one which will hybridise to some degree to all of the nucleotides in the target polynucleotide. A universal nucleotide is preferably one which will hybridise to some degree to nucleotides comprising the nucleosides adenosine (A), thymine (T), uracil (U), guanine (G) and cytosine (C). The universal nucleotide may hybridise more strongly to some nucleotides than to others. For instance, a universal nucleotide inosine (I) comprising the nucleoside, 2'-deoxyinosine, will show a preferential order of pairing of I-C>I-A>I-G approximately=I-T. For the purposes of the invention, it is only necessary that the universal nucleotide used in the one or more control polynucleotides hybridises to all of the nucleotides in the target polynucleotide.

The universal nucleotide preferably comprises one of the following nucleobases: hypoxanthine, 4-nitroindole, 5-nitroindole, 6-nitroindole, 3-nitropyrrole, nitroimidazole, 4-nitropyrazole. 4-nitrobenzimidazole, 5-nitroindazole. 4-aminobenzimidazole or phenyl (C6-aromatic ring. The universal nucleotide more preferably comprises one of the following nucleosides: 2'-deoxyinosine, inosine, 7-deaza-2-deoxyinosine, 7-deaza-inosine, 2-aza-deoxyinosine, 2-aza-inosine, 4-nitroindole 2'-deoxyribonucleoside, 4-nitroindole ribonucleoside, 5-nitroindole 2'-deoxyribonucleoside, 5-nitroindole ribonucleoside, 6-nitroindole 2'-deoxyribonucleoside, 6-nitroindole ribonucleoside, 3-nitropyrrole 2'-deoxyribonucleoside, 3-nitropyrrole ribonucleoside, an acyclic sugar analogue of hypoxanthine, nitroimidazole 2'-deoxyribonucleoside, nitroimidazole ribonucleoside, 4-nitropyrazole 2'-deoxyribonucleoside, 4-nitropyrazole ribonucleoside, 4-nitrobenzimidazole 2'-deoxyribonucleoside, 4-nitrobenzimidazole ribonucleoside, 5-nitroindazole 2'-deoxyribonucleoside, 5-nitroindazole ribonucleoside, 4-aminobenzimidazole 2'-deoxyribonucleoside. 4-aminobenzimidazole ribonucleoside, phenyl C-ribonucleoside or phenyl C-2'-deoxyribosyl nucleoside. The universal nucleotide most preferably comprises 2'-deoxyinosine.

The one or more control polynucleotides preferably comprise pseudo-complementary nucleotides. Pseudo-complementary (PC) nucleotides contain base analogs that form weak base pairs with one another, but form strong base pairs with standard bases. The strengthof base pairing can be determining by standard means in the art, such as by measureing the melting temperature. Consequently. PC-based polynucleotides have diminished intramolecular and intermolecular secondary structures and can readily hybridize to unmodified polynucleotides. One example of a pseudo-complementary base pair is the one between 2-aminoadenine (nA) and 2-thiothymine (sT). Compared with the Watson-Crick base pair between adenine (A) and thymine (T), the pair between nA and sT is unstable because of the steric clash between the exocyclic amine of nA and the large size of the sulphur atom of sT. While the nA:sT base pair is unstable, the base pairing strength of the A:sT pair is similar to that of an A: T base pair. The nA:T pair is more stable than A:T, presumably because three hydrogen bonds can now be formed between nA and T. The use of PC nucleotides in the one or more control polynucleotides means that the control nucleotides will hybridize with the target polynucleotide on the other side of the pore but will not hybridise with each other.

The one or more control polynucleotides may be complementary to the target polynucleotide and/or the hairpin loop. The hairpin loop is added to the target polynucleotide and so its sequence is known. It is therefore possible to design one or more control polynucleotides which are complementary to the hairpin loop, hybridise to the hairpin loop on the other side of the pore and prevent rehybridisation. The sequence of the target polynucleotide is typically unknown. However, it is straightforward to design a population of control polynucleotides which contain every combination of nucleotides which can be used to hybridise to the target polynucleotide. For instance, if the control polynucleotides are 4 nucleotides in length and A. G. T and C nucleotides (see below) are used to create them, a population containing $4^4$ (256) control polynucleotides can be designed which contain every possible combination of A, G, T and C. Any members of this population whose complementary sequences appear in the unknown sequence of the target sequence will hybridise to the unknown target sequence on the other side of the pore. The control polynucleotide is preferably sufficiently complementary to the target polynucleotide that it binds to the target polynucleotide under assay conditions for 0.5 ms or more, such as for from 1 ms to Is or 1 ms to 10 ms.

The one or more control polynucleotides may be any length. For instance, they may be at least 4, at least 5, at least 10, at least 15 or at least 20 nucleotides in length. Such lengths are suitable when the one or more control polynucleotides comprise universal nucleotides. The one or more control polynucleotides are preferably at least 30, at least 60 or at least 90 nucleotides in length. The one or more control polynucleotides may be up to 100, 200, 500, 1000, 10000 or 100000 nucleotides in length. The control strand may be longer than, the same length as or shorter than the target polynucleotide.

The one or more control polynucleotides preferably comprise one or more anchors which are capable of coupling the one or more control polynucleotides to the membrane. Suitable anchors are discussed below with reference to the target polynucleotide.

The one or more species preferably comprise (ii) one or more proteins or one or more chemicals which bind to the target polynucleotide and/or the hairpin loop. The conditions preferably comprise (ii) a plurality of proteins or chemicals which bind to the target polynucleotide and/or the hairpin loop. The conditions may comprise any number of proteins or chemicals, such as 2, 5, 10, 20, 50, 100, 500, 1000, 5000 or 10.000 or more. The one or more proteins may be any proteins which bind to single stranded polynucleotides. The proteins may be any of the polynucleotide binding proteins discussed below. The one or more proteins are preferably one or more single-stranded binding proteins (SSBs) or are one or more helicases. If the target polynucleotide is RNA, the one or more proteins may be one or more ribozymes.

The one or more chemicals may be any of the chemicals discussed below with reference to molecular brakes, such as one or more cyclodextrins.

The one or more species preferably comprise (iii) a nuclease. The nuclease is preferably an endonuclease, an exonuclease or a uracil-specific excision reagent (USERs). The nuclease digests the polynucleotide on the other side of the pore and prevents the formation of secondary structure and/or prevents rehybridisation.

The one or more species may comprise a combination of (i), (ii) and (iii), such as (i), (ii), (iii), (i) and (ii), (ii) and (iii), (i) and (iii) or (i), (ii) and (iii).

The species may be any molecule that can bind to the polynucleotide after it has passed through the transmembrane pore to inhibit secondary structure formation. There are many known types of proteins that bind to DNA/RNA. Such proteins include motor proteins but are preferably passive binders, for example, SSB, T4 gp32 or recA proteins. The species may be a molecular brake but does not not need to bind so strongly that it can slow a polynucleotide moving through a nanopore under force. The species only has to block or slow the formation of secondary/tertiary structure. Chemical species include, for example, intercalators, of which many are known in the art.

The conditions preferably comprise (a) a higher salt concentration on the other side of the pore than on the one side of the pore and/or (b) a lower pH on the other side of the pore than on the one side of the pore. The salt is preferably potassium glutamate (K-glutamate) or potassium chloride (KCl). In one embodiment, a higher salt concentration is typically a salt concentration that is about 5% or more or 10% or more greater. In another embodiment, a higher salt concentration is typically a difference of 10 mM or more, such as 100 mM or more up to about 1 M, 2 M or 3 M. In one embodiment, a lower pH is a pH of 0.5 pH units or more less.

The conditions preferably chemically or physically cleave the target polynucleotide on the other side of the pore. The conditions preferably comprise contacting the target polynucleotide on the other side of the pore with one or more restriction enzymes. The conditions preferably comprise passing the target polynucleotide through a small hole on the other side of the pore under pressure. The pressure could, by way of example, be voltage difference, osmotic pressure or fluidic pressure. A pressure differential can be applied across membranes/nanopores. The pressure may be a physical pressure applied by physical means (e.g., using a pump or syringe), or an osmotic pressure arising as aresult of a difference in chemical composition on the different sides of the membrane. The conditions preferably comprise nebulising the target polynucleotide on the other side of the pore. Other suitable conditions include, but are not limited to, the following:

Restriction digestion.

Acoustic shearing by the transmission of high-frequency acoustic energy waves.

Nebulization by forcing the polynucleotide through a small hole in a nebulizer unit.

Sonication.

Point-sink shearing, a type of hydrodynamic shearing, uses a syringe pump to create hydrodynamic shear forces by polynucleotides through a small abrupt contraction.

Needle shearing by passing the polynucleotides through small gauge needle.

French pressure cells pass polynucleotides through a narrow valve under high pressure to create high shearing forces.

Transposome mediated fragmentation (tagmentation).

The conditions preferably comprise chemically cleaving the target polynucleotide on the other side of the pore. The target polynucleotide is preferably chemically cleaved using one or more of Fe (II)-ethylenediaminetetraacetic acid (Fe (II)-EDTA), piperidine, benzenediazonium tetrafluoroborate, a metallo-intercalator and a metallo-inserter.

The conditions preferably comprise selectively cleaving the hairpin loop on the other side of the pore. The hairpin loop is preferably selectively cleaved by an enzyme. The loop may be designed so that it is selectively targeted by a restriction enzyme or a different type of nuclease, such as Cas9. The loop may be designed such that it self cleaves. For instance, certain ribozyme structures self cleave.

The conditions preferably comprise one or more species on the other side of the pore which increase the formation of secondary structure by the target polynucleotide. The one or more species are preferably interchelators or metal cofactors. Suitable metal cofactors include, but are not limited to, magnesium, such as $Mg^{2+}$, magnesium (II) chloride or magnesium (II) acetate: cobalt, such as $Co^{2+}$, cobalt (II) chloride or cobalt (II) acetate: manganese, such as $Mn^{2+}$, manganese (II) chloride or manganese (II) acetate; zinc, such as $Zn^{2+}$, zinc (II) sulphate monohydrate: calcium, such as $Ca^{2+}$, calcium (II) chloride or calcium (II) acetate monohydrate: aluminium, such as $Al^{3+}$ or aluminium (III) chloride: beryllium, such as $Be^{2+}$ or beryllium (II) sulphate; and nickel, such as $Ni^{2+}$ or nickel (II) sulphate hexhydrate. The metal cofactor is preferably potassium, such as $K^{+}$ or potassium chloride.

Hairpin Design

The invention provides an improved method of characterising a double stranded target polynucleotide. The target polynucleotide is provided as part of a construct in which the two strands of the target polynucleotide are linked at one end of the target polynucleotide by a hairpin loop. The method more preferably comprises the step of linking the two strands of the target polynucleotide at one end of the target polynucleotide by a hairpin loop to provide a construct comprising the target polynucleotide. The construct is contacted with one side of a transmembrane pore in a membrane. The construct is also contacted with a molecular brake which separates the two strands of the construct and controls the movement of the construct through the pore one strand at a time. Suitable pores, membranes and molecular brakes are discussed in more detail below. One or more measurements which are indicative of one or more characteristics of the target polynucleotide are taken as the construct moves with respect to the pore. An important part of the invention is that the hairpin loop is designed to control the ability of the two strands of the target polynucleotide to rehybridise on the other side of the pore. In other words, the hairpin is designed to control the rehybridisation of the two strands of the target polynucleotide/construct after it has moved through the pore.

The ability of the two strands of the target polynucleotide to rehybridise on the other side of the pore may be controlled in any way and to any extent. The hairpin loop may be designed to decrease, reduce or prevent the rehybridisation. The hairpin loop may decrease, reduce or prevent the rehybridisation by any amount, such by at least 10%, at least 20%, at least 30%, at least 40%, at least 50%, at least 60%, at least 70%, at least 80% or at least 90%. The hairpin more preferably abolishes the rehybridisation (i.e. decreases, reduces or prevents it by 100%).

Alternatively, the hairpin may be designed to increase the rehybridisation. The hairpin may increase the rehybridisation by any amount, such by at least 10%, at least 20%, at least 30%, at least 40%, at least 50%, at least 60%, at least 70%, at least 80% or at least 90%. The hairpin may increase the rehybridisation by at least twofold, at least threefold, at least fourfold, at least fivefold, at least tenfold, at least twentyfold, at least thirtyfold, at least fortyfold, at least fiftyfold, at least one hundredfold, at least five hundredfold or one thousandfold.

Rehybridisation may be measured in any known way. For example, rehybridisation may be measured by melting.

The hairpin loop is preferably designed to decrease the ability of the two strands of the target polynucleotide to rehybridise on the other side of the pore. The hairpin loop is more preferably designed to prevent the two strands of the target polynucleotide from rehybridising on the other side of the pore.

Preferably, the hairpin loop (a) can be selectively cleaved on the other side of the pore, (b) comprises a loop region having a length of 60 or more nucleotides, (c) comprises one or more sequences capable of forming random secondary structure, (d) has a reduced a melting temperature (Tm) or (e) any combination thereof. In (e), the hairpin preferably {a}; {b}; {c}; {d}; {a,b}: {a,c}; {a,d}; {b,c}; {b,d}; {c,d}; {a,b,c}; {a,b,d}; {a,c,d}; {b,c,d}; or {a,b,c,d}. The length of the hairoin loop may be from about 60 to about 1000 nucleotides such at about 100 to about 200 nucleotides.

The structure of hairpin loops is discussed above with reference to suitable "non-designed" hairpin loops for use in the invention.

In (a), selective cleavage of the hairpin loops means that the two strands of the target polynucleotide may move apart and reduce the likelihood of rehybridisation. Selective cleavage of hairpin loops is discussed above.

In (b), the loop region may be any length. The loop region may have a length of 70 or more, 80 or more, 90 or more, 100 or more, 125 or more or 150 or more nucleotides. The loop may comprise any of the nucleotides discussed below. The loop may comprise a long stretch of polyT (a long stretch of only nucleotides containing thymine (T)). Such stretehes may be 25 or more, 50 or more or 75 or more nucleotides in length. The loop may comprise one or more abasic nucleotides. A longer loop reduces the likelihood that the two strands of the target polynucleotide will rehybridise on the other side of the pore.

In (c), the hairpin loop may comprise one or more sequences capable of forming random secondary structure. The hairpin loop may comprise any number of sequences capable of forming random secondary structure, such as two or more, three or more, five or more or ten or more. The random secondary structure may be any of those discussed above. The hairpin loop preferably comprises one or more sequences which are capable of forming (a) one or more helices. (b) one or more loops, (c) one or more pseudoknots. (d) one or more quadruplexes or (e) a combination thereof, such as {a}; {b}; {c}; {d}; {a,b}; {a,c}; {a,d}; {b,c}; {b,d}; {c,d}; {a,b,c}; {a,b,d}; {a,c,d}; {b,c,d}; or {a,b,c,d}. The hairpin loop preferably comprises one or more sequences which are capable of forming one or more quadruplexes. The hairpin loop preferably comprises one or more quadruplexes with additional duplex structures, such as HD22 (a psudeo G4 with additional duplex structure). The sequence of HD22 is shown in the Examples. Such sequences are discussed above. The formation of random secondary structure by the hairpin loop on the other side of the pore reduces the likelihood that the two strands of the target polynucleotide will rehybridise on the other side of the pore.

In (d), the hairpin may have any reduction in melting temperature (Tm) Melting temperature and how it may be measured is discussed below. The stem region of the hairpin loop may comprise one or more mismatches, such as 1, 2, 3, 4, 5, 6, 7, 8 or more mismatches. Melting temperature may also be reduced by including one or more, such as 1, 2, 3, 4, 5, 6, 7, 8 or more universal nucleotides. Universal nucleotides are discussed in more detail below.

The hairpin loop is preferably designed to decrease the ability of the two strands of the target polynucleotide to rehybridise on the other side of the pore. However, the hairpin loop must be able to form a loop before it is ligated to and used to link the two strands of the target polynucleotide. This can be achieved by forming the loop in the absence of free metal cofactors, such as in the absence of free potassium ions. The metal cofactors may be any of those discussed above. Such cofactors may be sequestered (such that they are not free) using a chelator, such as EDTA (Ethylenediaminetetraacetic acid). The presence of the cofactors on the other side of the pore allows the designed hairpin to function in accordance with the invention.

The hairpin loop is preferably designed to increase the ability of the two strands of the target polynucleotide to rehybridise on the other side of the pore. This allows the uplift to be more consistent and predictable.

Preferably, the hairpin loop (a) comprises a loop region having a length of 20 or fewer nucleotides, such as 10 or fewer or 5 or fewer nucleotides and/or (b) has an increased melting temperature (Tm). Melting temperature may be increased by forming the stem region from nucleotides which hybridise to each other more strongly than natural DNA or RNA nucleotides, such as BNA nucleotides.
Polynucleotide The target polynucleotide may be any polynucleotide. The control polynucleotide may also be any type of polynucleotide.

A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the polynucleotide can be oxidized or methylated. One or more nucleotides in the polynucleotide may be damaged. For instance, the polynucleotide may comprise a pyrimidine dimer. Such dimers are typically associated with damage by ultraviolet light and are the primary cause of skin melanomas. One or more nucleotides in the polynucleotide may be modified, for instance with a label or a tag. Suitable labels are described below. The polynucleotide may comprise one or more spacers.

A nucleotide typically contains a nucleobase, a sugar and at least one phosphate group. The nucleobase and sugar form a nucleoside.

The nucleobase is typically heterocyclic. Nucleobases include, but are not limited to, purines and pyrimidines and more specifically adenine (A), guanine (G)m thymine (T), uracil (U) and cytosine (C).

The sugar is typically a pentose sugar. Nucleotide sugars include, but are not limited tom ribose and deoxyribose. The sugar is preferably a deoxyribose.

The polynucleotide preferably comprises the following nucleosides: deoxyadenosine (dA), deoxyuridine (dU) and/or thymidine (dT), deoxyguanosine (dG) and deoxycytidine (dC).

The nucleotide is typically a ribonucleotide or deoxyribonucleotide. The nucleotide typically contains a monophosphate, diphosphate or triphosphate. The nucleotide may comprise more than three phosphates, such as 4 or 5 phosphates. Phosphates may be attached on the 5' or 3' side of a nucleotide. Nucleotides include, but are not limited to, adenosine monophosphate (AMP), guanosine monophosphate (GMP), thymidine monophosphate (TMP), uridine monophosphate (UMP), 5-methylcytidine monophosphate, 5-hydroxymethylcytidine monophosphate, cytidine monophosphate (CMP), cyclic adenosine monophosphate (cAMP), cyclic guanosine monophosphate (cGMP), deoxyadenosine monophosphate (dAMP), deoxyguanosine monophosphate (dGMP), deoxythymidine monophosphate (dTMP), deoxyuridine monophosphate (dUMP), deoxycytidine monophosphate (dCMP) and deoxymethylcytidine monophosphate. The nucleotides are preferably selected from AMP. TMP. GMP, CMP, UMP, dAMP, dTMP, dGMP, dCMP and dUMP.

A nucleotide may be abasic (i.e. lack a nucleobase). A nucleotide may also lack a nucleobase and a sugar (i.e. is a C3 spacer).

The nucleotides in the polynucleotide may be attached to each other in any manner. The nucleotides are typically attached by their sugar and phosphate groups as in nucleic acids. The nucleotides may be connected via their nucleobases as in pyrimidine dimers.

The polynucleotide may be single stranded or double stranded. At least a portion of the polynucleotide is preferably double stranded.

The polynucleotide can be a nucleic acid, such as deoxyribonucleic acid (DNA) or ribonucleic acid (RNA) The polynucleotide can comprise one strand of RNA hybridised to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA), bridged nucleic acid (BNA) or other synthetic polymers with nucleotide side chains. The PNA backbone is composed of repeating N-(2-aminoethyl)-glycine units linked by peptide bonds. The GNA backbone is composed of repeating glycol units linked by phosphodiester bonds. The TNA backbone is composed of repeating threose sugars linked together by phosphodiester bonds. LNA is formed from ribonucleotides as discussed above having an extra bridge connecting the 2' oxygen and 4' carbon in the ribose moiety. Bridged nucleic acids (BNAs) are modified RNA nucleotides. They are sometimes also referred to as constrained or inaccessible RNA molecules. BNA monomers can contain a five-membered, six-membered or even a seven-membered bridged structure with a "fixed" C3'-endo sugar puckering. The bridge is synthetically incorporated at the 2', 4'-position of the ribose to afford a 2', 4'-BNA monomer. The monomers can be incorporated into oligonucleotide polymeric structures using standard phosphoamidite chemistry. BNAs are structurally rigid oligo-nucleotides with increased binding affinities and stability.

The polynucleotide is most preferably ribonucleic nucleic acid (RNA) or deoxyribonucleic acid (DNA).

The target polynucleotide can be any length. For example, the target polynucleotide can be at least 10, at least 50, at least 100, at least 150, at least 200, at least 250, at least 300, at least 400 or at least 500 nucleotides or nucleotide pairs in length. The polynucleotide can be 1000 or more nucleotides or nucleotide pairs. 5000 or more nucleotides or nucleotide pairs in length or 100000 or more nucleotides or nucleotide pairs in length.

The control polynucleotide can be any length. For example, the control polynucleotide can be at least 10, at least 50, at least 100, at least 150, at least 200, at least 250, at least 300, at least 400 or at least 500 nucleotides or nucleotide pairs in length. The polynucleotide can be 1000 or more nucleotides or nucleotide pairs, 5000 or more nucleotides or nucleotide pairs in length or 100000 or more nucleotides or nucleotide pairs in length. In one embodiment, the control polynucleotide is shorter than the target polynucleotide, by from about 2 to 500000 nucleotides, such as about 10 to 500, 50 to 300, or 100 to 200 nucleotides shorter.

Sample

The target polynucleotide may be present in any suitable sample. The sample may be a biological sample. The invention may be carried out in vitro using at least one sample obtained from or extracted from any organism or microorganism. The organism or microorganism is typically archaeal, prokaryotic or eukaryotic and typically belongs to one of the five kingdoms: plantae, animalia, fungi, monera and protista. The invention may be carried out in vitro on at least one sample obtained from or extracted from any virus. The sample is preferably a fluid sample. The sample typically comprises a body fluid of the patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep, fish, chickens or pigs or may alternatively be pets such as cats or dogs. Alternatively, the sample may be of plant origin, such as a sample obtained from a commercial crop, such as a cereal, legume, fruit or vegetable, for example wheat, barley, oats, canola, maize, soya, rice, rhubarb, bananas, apples, tomatoes, potatoes, grapes, tobacco, beans, lentils, sugar cane, cocoa, cotton.

The sample may be a non-biological sample. The non-biological sample is preferably a fluid sample. Examples of non-biological samples include surgical fluids, water such as drinking water, sea water or river water, and reagents for laboratory tests.

The sample is typically processed prior to being used in the invention, for example by centrifugation or by passage through a membrane that filters out unwanted molecules or cells, such as red blood cells. The sample may be measured immediately upon being taken. The sample may also be typically stored prior to assay, preferably below −70° C.

Membrane

The target polynucleotide is contacted with one side of a transmembrane pore in a membrane. Any membrane may be used in accordance with the invention. Suitable membranes are well-known in the art. The membrane is preferably an amphiphilic layer. An amphiphilic layer is a layer formed from amphiphilic molecules, such as phospholipids, which have both hydrophilic and lipophilic properties. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units are polymerised together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphiphiles. The copolymer may be a triblock, tetrablock or pentablock copolymer. The membrane is preferably a triblock copolymer membrane.

Archaebacterial bipolar tetraether lipids are naturally occurring lipids that are constructed such that the lipid forms a monolayer membrane. These lipids are generally found in extremophiles that survive in harsh biological environments, thermophiles, balophiles and acidophiles. Their stability is believed to derive from the fused nature of the final bilayer. It is straightforward to construct block copolymer materials that mimic these biological entities by creating a triblock polymer that has the general motif hydrophilic-hydrophobic-hydrophilic. This material may form monomeric membranes that behave similarly to lipid bilayers and encompass a range of phase behaviours from vesicles through to laminar membranes. Membranes formed from these triblock copolymers hold several advantages over biological lipid membranes. Because the triblock copolymer is synthesised, the exact construction can be carefully controlled to provide the correct chain lengths and properties required to form membranes and to interact with pores and other proteins.

Block copolymers may also be constructed from sub-units that are not classed as lipid sub-materials: for example a hydrophobic polymer may be made from siloxane or other non-hydrocarbon based monomers. The hydrophilic sub-section of block copolymer can also possess low protein binding properties, which allows the creation of a membrane that is highly resistant when exposed to raw biological samples. This head group unit may also be derived from non-classical lipid head-groups.

Triblock copolymer membranes also have increased mechanical and environmental stability compared with biological lipid membranes, for example a much higher operational temperature or pH range. The synthetic nature of the block copolymers provides a platform to customise polymer based membranes for a wide range of applications.

The membrane is most preferably one of the membranes disclosed in International Application No. PCT/GB2013/052766 (published as WO 2014/064443) or PCT/GB2013/052767 (published as WO 2014/064444).

The amphiphilic molecules may be chemically-modified or functionalised to facilitate coupling of the polynucleotide.

The amphiphilic layer may be a monolayer or a bilayer. The amphiphilic layer is typically planar. The amphiphilic layer may be curved. The amphiphilic layer may be supported. The amphiphilic layer may be concave. The amphiphilic layer may be suspended from raised such that the peripheral region of the amphiphilic layer (which is attached to the pillars) is higher than the amphiphilic layer region. This may allow the microparticle to travel, move, slide or roll along the membrane as described above.

Amphiphilic membranes are typically naturally mobile, essentially acting as two dimensional fluids with lipid diffusion rates of approximately $10^{-8}$ cm s-1. This means that the pore and coupled polynucleotide can typically move within an amphiphilic membrane.

The membrane may be a lipid bilayer. Lipid bilayers are models of cell membranes and serve as excellent platforms for a range of experimental studies. For example, lipid bilavers can be used for in vitro investigation of membrane proteins by single-channel recording. Alternatively, lipid bilayers can be used as biosensors to detect the presence of a range of substances. The lipid bilayer may be any lipid bilaver. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000563 (published as WO 2008/102121). International Application No. PCT/GB08/004127 (published as WO 2009/077734) and International Application No. PCT/GB2006/001057 (published as WO 2006/100484).

Methods for forming lipid bilayers are known in the art. Suitable methods are disclosed in the Example. Lipid bilayers are commonly formed by the method of Montal and Mueller (Proc. Natl. Acad. Sci. USA., 1972:69: 3561-3566), in which a lipid monolayer is carried on aqueous solution/air interface past either side of an aperture which is perpendicular to that interface. The lipid is normally added to the surface of an aqueous electrolyte solution by first dissolving it in an organic solvent and then allowing a drop of the solvent to evaporate on the surface of the aqueous solution on either side of the aperture. Once the organic solvent has evaporated, the solution/air interfaces on either side of the aperture are physically moved up and down past the aperture until a bilayer is formed. Planar lipid bilayers may be formed across an aperture in a membrane or across an opening into a recess.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

Tip-dipping bilayer formation entails touching the aperture surface (for example, a pipette tip) onto the surface of a test solution that is carrying a monolayer of lipid. Again, the lipid monolayer is first generated at the solution/air interface by allowing a drop of lipid dissolved in organic solvent to evaporate at the solution surface. The bilayer is then formed by the Langmuir-Schaefer process and requires mechanical automation to move the aperture relative to the solution surface.

For painted bilayers, a drop of lipid dissolved in organic solvent is applied directly to the aperture, which is submerged in an aqueous test solution. The lipid solution is spread thinly over the aperture using a paintbrush or an equivalent. Thinning of the solvent results in formation of a lipid bilayer. However, complete removal of the solvent from the bilayer is difficult and consequently the bilayer formed by this method is less stable and more prone to noise during electrochemical measurement.

Patch-clamping is commonly used in the study of biological cell membranes. The cell membrane is clamped to the end of a pipette by suction and a patch of the membrane becomes attached over the aperture. The method has been adapted for producing lipid bilayers by clamping liposomes which then burst to leave a lipid bilayer sealing over the aperture of the pipette. The method requires stable, giant and unilamellar liposomes and the fabrication of small apertures in materials having a glass surface.

Liposomes can be formed by sonication, extrusion or the Mozafari method (Colas et al. (2007) Micron 38:841-847).

In a preferred embodiment, the lipid bilayer is formed as described in International Application No PCT/GB08/004127 (published as WO 2009/077734) Advantageously in this method, the lipid bilayer is formed from dried lipids. In a most preferred embodiment, the lipid bilayer is formed across an opening as described in WO2009/077734 (PCT/GB08/004127).

A lipid bilayer is formed from two opposing layers of lipids. The two layers of lipids are arranged such that their hydrophobic tail groups face towards each other to form a hydrophobic interior. The hydrophilic head groups of the lipids face outwards towards the aqueous environment on each side of the bilayer. The bilayer may be present in a number of lipid phases including, but not limited to, the liquid disordered phase (fluid lamellar), liquid ordered phase, solid ordered phase (lamellar gel phase, interdigitated gel phase) and planar bilayer crystals (lamellar sub-gel phase, lamellar crystalline phase).

Any lipid composition that forms a lipid bilayer may be used. The lipid composition is chosen such that a lipid bilayer having the required properties, such as surface charge, ability to support membrane proteins, packing density or mechanical properties, is formed. The lipid composition can comprise one or more different lipids. For instance, the lipid composition can contain up to 100 lipids. The lipid composition preferably contains 1 to 10 lipids. The lipid composition may comprise naturally-occurring lipids and/or artificial lipids.

The lipids typically comprise a head group, an interfacial moiety and two hydrophobic tail groups which may be the same or different. Suitable head groups include, but are not limited to, neutral head groups, such as diacylglycerides (DG) and ceramides (CM); zwitterionic head groups, such as phosphatidylcholine (PC), phosphatidylethanolamine (PE) and sphingomyelin (SM): negatively charged head groups, such as phosphatidylglycerol (PG); phosphatidylserine (PS), phosphatidylinositol (PI), phosphatic acid (PA) and cardiolipin (CA); and positively charged headgroups, such as trimethylammonium-Propane (TAP). Suitable interfacial moieties include, but are not limited to, naturally-occurring interfacial moieties, such as glycerol-based or ceramide-based moieties. Suitable hydrophobic tail groups include, but are not limited to, saturated hydrocarbon chains, such as lauric acid (n-Dodecanolic acid), myristic acid (n-Tetradeconic acid), palmitic acid (n-Hexadecanoic acid), stearic acid (n-Octadecanoic) and arachidic (n-Eicosanoic): unsaturated hydrocarbon chains, such as oleic acid (cis-9-Octadecanoic); and branched hydrocarbon chains, such as phytanoyl. The length of the chain and the position and number of the double bonds in the unsaturated hydrocarbon chains can vary. The length of the chains and the position and number of the branches, such as methyl groups, in the branched hydrocarbon chains can vary. The hydrophobic tail groups can be linked to the interfacial moiety as an ether or an ester. The lipids may be mycolic acid.

The lipids can also be chemically-modified. The head group or the tail group of the lipids may be chemically-modified. Suitable lipids whose head groups have been chemically-modified include, but are not limited to, PEG-modified lipids, such as 1.2-Diacyl-sn-Glycero-3-Phosphoethanolamine-N-[Methoxy (Polyethylene glycol)-2000]: functionalised PEG Lipids, such as 1,2-Distearoyl-sn-Glycero-3 Phosphoethanolamine-N-[Biotinyl(Polyethylene Glycol) 2000]; and lipids modified for conjugation, such as 1,2-Dioleoyl-sn-Glycero-3-Phosphoethanolamine-N-(succinyl) and 1.2-Dipalmitoyl-sn-Glycero-3-Phosphoethanolamine-N-(Biotinyl). Suitable lipids whose tail groups have been chemically-modified include, but are not limited to, polymerisable lipids, such as 1,2-bis (10, 12-tricosadiynoyl)-sn-Glycero-3-Phosphocholine: fluorinated lipids, such as 1-Palmitoyl-2-(16-Fluoropalmitoyl)-sn-Glycero-3-Phosphocholine: deuterated lipids, such as 1,2-Dipalmitoyl-D62-sn-Glycero-3-Phosphocholine; and ether linked lipids, such as 1.2-Di-O-phytanyl-sn-Glycero-3-Phosphocholine. The lipids may be chemically-modified or functionalised to facilitate coupling of the polynucleotide.

The amphiphilic layer, for example the lipid composition, typically comprises one or more additives that will affect the properties of the layer. Suitable additives include, but are not limited to, fatty acids, such as palmitic acid, myristic acid and oleic acid: fatty alcohols, such as palmitic alcohol, myristic alcohol and oleic alcohol; sterols, such as cholesterol, ergosterol, lanosterol, sitosterol and stigmasterol: lysophospholipids, such as 1-Acyl-2-Hydroxy-sn-Glycero-3-Phosphocholine; and ceramides.

In another preferred embodiment, the membrane is a solid state layer. Solid state layers can be formed from both organic and inorganic materials including, but not limited to, microelectronic materials, insulating materials such as $HfO_2$, $Si_3N_4$, $Al_2O_3$, and SiO, organic and inorganic polymers such as polyamide, plastics such as TEFLON® or elastomers such as two-component addition-cure silicone rubber, and glasses. The solid state layer may be by atomic layer deposition (ALD). The ALD solid state layer may comprise alternating layers of HfO; and $Al_2O_3$ The solid state layer may be formed from monatomic layers, such as graphene, or layers that are only a few atoms thick. Suitable graphene layers are disclosed in International Application No. PCT/US2008/010637 (published as WO 2009/035647). Yusko et al., Nature Nanotechnology, 2011:6: 253-260 and US Patent Application No. 2013/0048499 describe the delivery of proteins to transmembrane pores in solid state layers without the use of microparticles. The method of the invention may be used to improve the delivery in the methods disclosed in these documents.

The method is typically carried out using (i) an artificial amphiphilic layer comprising a pore. (ii) an isolated, naturally-occurring lipid bilayer comprising a pore, or (iii) a cell having a pore inserted therein. The method is typically carried out using an artificial amphiphilic layer, such as an artificial triblock copolymer layer. The layer may comprise other transmembrane and/or intramembrane proteins as well as other molecules in addition to the pore. Suitable apparatus and conditions are discussed below. The method of the invention is typically carried out in vitro.

Transmembrane Pore

A transmembrane pore is a structure that crosses the membrane to some degree. Typically, a transmembrane pore comprises a first opening and a second opening with a lumen extending between the first opening and the second opening. The transmembrane pore permits hydrated ions driven by an applied potential to flow across or within the membrane. The transmembrane pore typically crosses the entire membrane so that hydrated ions may flow from one side of the membrane to the other side of the membrane. However, the transmembrane pore does not have to cross the membrane. It may be closed at one end. For instance, the pore may be a well, gap, channel, trench or slit in the membrane along which or into which hydrated ions may flow.

Any transmembrane pore may be used in the invention. The pore may be biological or artificial. Suitable pores include, but are not limited to, protein pores, polynucleotide pores and solid state pores. The pore may be a DNA origami pore (Langecker et al., Science, 2012; 338:932-936).

The transmembrane pore is preferably a transmembrane protein pore. A transmembrane protein pore is a polypeptide or a collection of polypeptides that permits hydrated ions, such as polynucleotide, to flow from one side of a membrane to the other side of the membrane. In the present invention, the transmembrane protein pore is capable of forming a pore that permits hydrated ions driven by an applied potential to flow from one side of the membrane to the other. The transmembrane protein pore preferably permits polynucleotides to flow from one side of the membrane, such as a triblock copolymer membrane, to the other. The transmembrane protein pore allows a polynucleotide, such as DNA or RNA, to be moved through the pore.

The transmembrane protein pore may be a monomer or an oligomer. The pore is preferably made up of several repeating subunits, such as at least 6, at least 7, at least 8, at least 9, at least 10, at least 11, at least 12, at least 13, at least 14, at least 15, or at least 16 subunits. The pore is preferably a hexameric, heptameric, octameric or nonameric pore. The pore may be a homo-oligomer or a hetero-oligomer.

The transmembrane protein pore typically comprises a barrel or channel through which the ions may flow. The subunits of the pore typically surround a central axis and contribute strands to a transmembrane β barrel or channel or a transmembrane α-helix bundle or channel.

The barrel or channel of the transmembrane protein pore typically comprises amino acids that facilitate interaction with s, such as nucleotides, polynucleotides or nucleic acids. These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids.

Transmembrane protein pores for use in accordance with the invention can be derived from p-barrel pores or α-helix bundle pores. B-barrel pores comprise a barrel or channel that is formed from β-strands. Suitable β-barrel pores include, but are not limited to, B-toxins, such as α-hemolysin, anthrax toxin and leukocidins, and outer membrane proteins/porins of bacteria, such as *Mycobacterium smegmatis* porin (Msp), for example MspA. MspB. MspC or MspD, CsgG, outer membrane porin F (OmpF), outer membrane porin G (OmpG), outer membrane phospholipase A and *Neisseria* autotransporter lipoprotein (NalP) and other pores, such as lysenin α-helix bundle pores comprise a barrel or channel that is formed from α-helices. Suitable α-helix bundle pores include, but are not limited to, inner membrane proteins and a outer membrane proteins, such as WZA and ClyA toxin. The transmembrane pore may be derived from lysenin. Suitable pores derived from CsgG are disclosed in International Application No PCT/EP2015/069965. Suitable pores derived from lysenin are disclosed in International Application No. PCT/GB2013/050667 (published as WO 2013/153359). The transmembrane pore may be derived from or based on Msp, α-hemolysin (α-HL), lysenin, CsgG. ClyA, Spl and haemolytic protein fragaceatoxin C (FraC). The wild type α-hemolysin pore is formed of 7 identical monomers or sub-units (i.e., it is heptameric). The sequence of one monomer or sub-unit of α-hemolysin-NN is shown in SEQ ID NO: 4.

The transmembrane protein pore is preferably derived from Msp, more preferably from MspA. Such a pore will be oligomeric and typically comprises 7, 8, 9 or 10 monomers derived from Msp. The pore may be a homo-oligomeric pore derived from Msp comprising identical monomers. Alternatively, the pore may be a hetero-oligomeric pore derived from Msp comprising at least one monomer that differs from the others. Preferably the pore is derived from MspA or a homolog or paralog thereof.

A monomer derived from Msp typically comprises the sequence shown in SEQ ID NO: 2 or a variant thereof. SEQ ID NO: 2 is the MS-(B1) 8 mutant of the MspA monomer. It includes the following mutations: D90N, D91N, D93N, D118R, D134R and E139K. A variant of SEQ ID NO: 2 is a polypeptide that has an amino acid sequence which varies from that of SEQ ID NO: 2 and which retains its ability to form a pore. The ability of a variant to form a pore can be assayed using any method known in the art. For instance, the variant may be inserted into an amphiphilic layer along with other appropriate subunits and its ability to oligomerise to form a pore may be determined. Methods are known in the art for inserting subunits into membranes, such as amphiphilic layers. For example, subunits may be suspended in a purified form in a solution containing a triblock copolymer membrane such that it diffuses to the membrane and is inserted by binding to the membrane and assembling into a functional state. Alternatively, subunits may be directly inserted into the membrane using the "pick and place" method described in M.A. Holden, H. Bayley. J. Am. Chem. Soc. 2005, 127, 6502-6503 and International Application No. PCT/GB2006/001057 (published as WO 2006/100484).

Over the entire length of the amino acid sequence of SEQ ID NO: 2, a variant will preferably be at least 50% homologous to that sequence based on amino acid similarity or identity. More preferably, the variant may be at least 55%, at least 60%, at least 65%, at least 70%, at least 75%, at least 80%, at least 85%, at least 90% and more preferably at least 95%. 97% or 99% homologous based on amino acid simlarity or identity to the amino acid sequence of SEQ ID NO: 2 over the entire sequence. There may be at least 80%, for example at least 85%, 90% or 95%, amino acid similarity or identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et al (1984) Nucleic Acids Research 12, p387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10. Software for performing BLAST analyses is publicly available through the National Center for Biotechnology Information (http://www.ncbi.nlm.nih.gov/). Similarity can be measured using pairwise identity or by applying a scoring matrix such as BLOSUM62 and converting to an equivalent identity. Since they represent functional rather than evolved changes, deliberately mutated positions would be masked when determining homology. Similarity may be determined more sensitively by the application of position-specific scoring matrices using, for example, PSIBLAST on a comprehensive database of protein sequences. A different scoring matrix could be used that reflect amino acid chemico-physical properties rather than frequency of substitution over evolutionary time scales (e.g. charge).

SEQ ID NO: 2 is the MS-(B1) 8 mutant of the MspA monomer. The variant may comprise any of the mutations in the MspB, C or D monomers compared with MspA. The mature forms of MspB, C and D are shown in SEQ ID NOs: 5 to 7. In particular, the variant may comprise the following substitution present in MspB: A138P. The variant may comprise one or more of the following substitutions present in MspC: A96G, N102E and A138P. The variant may comprise one or more of the following mutations present in MspD: Deletion of G1, L2V. ESQ, L8V, D13G, W21A, D22E, K47T, I49H, I68V, D91G, A96Q, N102D, S103T, V104I, S136K and G141A. The variant may comprise combinations of one or more of the mutations and substitutions from Msp B, C and D. The variant preferably comprises the mutation L88N. A variant of SEQ ID NO: 2 has the mutation L88N in addition to all the mutations of MS-B1 and is called MS-(B2) 8. The pore used in the invention is preferably MS-(B2) 8. The variant of SEQ ID NO: 2 preferably comprises one or more of D56N, D56F, E59R. G75S, G77S, A96D and Q126R. A variant of SEQ ID NO: 2 has the mutations G75S/G77S/L88N/Q126R in addition to all the mutations of MS-B1 and is called MS-B2C. The pore used in the invention is preferably MS-(B2) 8 or MS-(B2C) 8. The variant of SEQ ID NO: 2 preferably comprises N93D. The variant more preferably comprises the mutations G75S/G77S/L88N/N93D/Q126R.

Amino acid substitutions may be made to the amino acid sequence of SEQ ID NO: 2 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid.

The transmembrane protein pore is preferably derived from CsgG, more preferably from CsgG from E. coli Str. K-12 substr. MC4100. Such a pore will be oligomeric and typically comprises 7, 8, 9 or 10 monomers derived from CsgG. The pore may be a homo-oligomeric pore derived from CsgG comprising identical monomers. Alternatively, the pore may be a hetero-oligomeric pore derived from CsgG comprising at least one monomer that differs from the others.

A monomer derived from CsgG typically comprises the sequence shown in SEQ ID NO: 27 or a variant thereof. A variant of SEQ ID NO. 27 is a polypeptide that has an amino acid sequence which varies from that of SEQ ID NO: 27 and which retains its ability to form a pore. The ability of a variant to form a pore can be assayed using any method known in the art as discussed above.

Over the entire length of the amino acid sequence of any one of SEQ ID NO: 27, a variant will preferably be at least 50% homologous to that sequence based on amino acid similarity or identity. More preferably, the variant may be at least 55%, at least 60%, at least 65%, at least 70%, at least 75%, at least 80%, at least 85%, at least 90% and more preferably at least 95%. 97% or 99% homologous based on amino acid similarity or identity to the amino acid sequence of SEQ ID NO: 27 over the entire sequence. There may be at least 80%, for example at least 85%, 90% or 95%, amino acid similarity or identity over a stretch of 100 or more, for example 125, 150, 175 or 200 or more, contiguous amino acids ("hard homology"). Homology can be measured as discussed above.

The variant of SEQ ID NO: 27 may comprise any of the mutations disclosed in International Application No. PCT/GB2015/069965 (published as WO 2016/034591). The variant of SEQ ID NO: 27 preferably comprises one or more of the following (i) one or more mutations at the following positions (i.e. mutations at one or more of the following positions) N40, D43, E44, S54, S57, Q62, R97, E101. E124, E131, R142, T150 and R192, such as one or more mutations at the following positions (i.e. mutations at one or more of the following positions) N40, D43, E44, S54. S57, Q62. E101, E131 and T150 or N40. D43. E44, E101 and E131: (ii) mutations at Y51/N55. Y51/F56, N55/F56 or Y51/N55/F56; (iii) Q42R or Q42K: (iv) K49R: (v) N102R. N102F, N102Y or N102W: (vi) D149N, D149Q or D149R: (vii) E185N. E185Q or E185R: (viii) D195N, D195Q or D195R; (ix) E20IN, E201Q or E201R: (x) E203N. E203Q or E203R; and (xi) deletion of one or more of the following positions F48, K49, P50. Y51, P52, A53, S54, N55, F56 and S57. The variant may comprise any combination of (i) to (xi). If the variant comprises any one of (i) and (iii) to (xi), it may further comprise a mutation at one or more of Y51. N55 and F56, such as at Y51. N55. F56. Y51/N55. Y51/F56, N55/F56 or Y51/N55/F56.

Preferred variants of SEQ ID NO: 27 which form pores in which fewer nucleotides contribute to the current as the polynucleotide moves through the pore comprise Y51A/F56A, Y51A/F56N, Y51I/F56A, Y51L/F56A, Y51T/F56A, Y51I/F56N, Y51L/F56N or Y51T/F56N or more preferably Y51I/F56A, Y51L/F56A or Y51T/F56A.

Preferred variants of SEQ ID NO: 27 which form pores displaying an increased range comprise mutations at the following positions:
Y51, F56, D149, E185, E201 and E203;
N55 and F56;
Y51 and F56;
Y51, N55 and F56; or
F56 and N102.

Preferred variants of SEQ ID NO: 27 which form pores displaying an increased range comprise:
Y51N, F56A, D149N, E185R, E201N and E203N;
N55S and F56Q;
Y51A and F56A;
Y51A and F56N;
Y51I and F56A;
Y51L and F56A;
Y51T and F56A;
Y51I and F56N;
Y51L and F56N;
Y51T and F56N;
Y51T and F56Q;
Y51A, N55S and F56A;
Y51A, N55S and F56N;
Y51T, N55S and F56Q; or
F56Q and N102R.

Preferred variants of SEQ ID NO: 27 which form pores in which fewer nucleotides contribute to the current as the polynucleotide moves through the pore comprise mutations at the following positions:
N55 and F56, such as N55X and F56Q, wherein X is any amino acid; or
Y51 and F56, such as Y51X and F56Q, wherein X is any amino acid.

Preferred variants of SEQ ID NO: 27 which form pores displaying an increased throughput comprise mutations at the following positions:
D149, E185 and E203;
D149, E185, E201 and E203; or
D149, E185, D195, E201 and E203.

Preferred variants which form pores displaying an increased throughput comprise:
D149N, E185N and E203N;
D149N, E18SN, E201N and E203N;
D149N, E185R, D195N, E201N and E203N; or
D149N, E185R, D195N, E201R and E203N.

Preferred variants of SEQ ID NO: 7 which form pores in which capture of the polynucleotide is increased comprise the following mutations:
D43N/Y5IT/F56Q;
E44N/Y5IT/F56Q;
D43N/E44N/Y5IT/F56Q;
Y51T/F56Q/Q62R;
D43N/Y51T/F56Q/Q62R;
E44N/Y51T/F56Q/Q62R; or
D43N/E44N/Y51T/F56Q/Q62R.

Preferred variants of SEQ ID NO: 27 comprise the following mutations:
D149R/E185R/E201R/E203R or Y51T/F56Q/D149R/E185R/E201R/E203R;
D149N/E185N/E201N/E203N or Y51T/F56Q/D149N/E185N/E201N/E203N;
E201R/E203R or Y51T/F56Q/E201R/E203R
E201N/E203R or Y51T/F56Q/E201N/E203R;
E203R or Y51T/F56Q/E203R;
E203N or Y51T/F56Q/E203N;
E201R or Y51T/F56Q/E201R;
E201N or Y51T/F56Q/E201N;
E185R or Y51T/F56Q/E185R;
E185N or Y51T/F56Q/E185N;
D149R or Y51T/F56Q/D149R;
D149N or Y51T/F56Q/D149N;
R142E or Y51T/F56Q/R142E;
R142N or Y51T/F56Q/R142N;
R192E or Y51T/F56Q/R192E; or
R192N or Y51T/F56Q/R192N.

Preferred variants of SEQ ID NO: 27 comprise the following mutations:
Y51A/F56Q/E101N/N102R;
Y51A/F56Q/R97N/N102G;
Y51A/F56Q/R97N/N102R;
Y51A/F56Q/R97N;
Y51A/F56Q/R97G;
Y51A/F56Q/R97L;
Y51A/F56Q/N102R;
Y51A/F56Q/N102F;
Y51A/F56Q/N102G;
Y51A/F56Q/E101R;
Y51A/F56Q/E101F;
Y51A/F56Q/E101N; or
Y51A/F56Q/E101G The variant of SEQ ID NO: 27 may comprise any of the substitutions present in another CsgG homologue. Preferred CsgG homologues are shown in SEQ ID NOs: 3 to 7 and 26 to 41 of International Application No. PCT/GB2015/069965 (published as WO 2016/034591).

Any of the proteins described herein, such as the transmembrane protein pores, may be modified to assist their identification or purification, for example by the addition of histidine residues (a his tag), aspartic acid residues (an asp tag), a streptavidin tag, a flag tag, a SUMO tag, a GST tag or a MBP tag, or by the addition of a signal sequence to promote their secretion from a cell where the polypeptide does not naturally contain such a sequence. An alternative to introducing a genetic tag is to chemically react a tag onto a native or engineered position on the pore or construct. An example of this would be to react a gel-shift reagent to a cysteine engineered on the outside of the pore. This has been demonstrated as a method for separating hemolysin hetero-oligomers (Chem Biol. 1997 July: 4 (7): 497-505).

The pore may be labelled with a revealing label. The revealing label may be any suitable label which allows the pore to be detected. Suitable labels include, but are not limited to, fluorescent molecules, radioisotopes, e.g. $^{125}$I, $^{35}$S, enzymes, antibodies, antigens, polynucleotides and ligands such as biotin.

Any of the proteins described herein, such as the transmembrane protein pores, may be made synthetically or by recombinant means. For example, the pore may be synthesised by in vitro translation and transcription (IVTT). The amino acid sequence of the pore may be modified to include non-naturally occurring amino acids or to increase the stability of the protein. When a protein is produced by synthetic means, such amino acids may be introduced during production. The pore may also be altered following either synthetic or recombinant production.

Any of the proteins described herein, such as the transmembrane protein pores, can be produced using standard methods known in the art. Polynucleotide sequences encoding a pore or construct may be derived and replicated using standard methods in the art. Polynucleotide sequences encoding a pore or construct may be expressed in a bacterial host cell using standard techniques in the art. The pore may be produced in a cell by in situ expression of the polypeptide from a recombinant expression vector. The expression vector optionally carries an inducible promoter to control the expression of the polypeptide. These methods are described in Sambrook, J and Russell, D. (2001). Molecular Cloning: A Laboratory Manual, 3rd Edition. Cold Spring Harbor Laboratory Press, Cold Spring Harbor, NY.

The pore may be produced in large scale following purification by any protein liquid chromatography system from protein producing organisms or after recombinant expression. Typical protein liquid chromatography systems include FPLC, AKTA™ systems, the Bio-Cad system, the Bio-Rad BIOLOGIC™ system and the Gilson HPLC system.

Microparticle

A microparticle may be used to deliver the target polynucleotide to the transmembrane pore. Any number of microparticles can be used in the method of the invention. For instance, the method of the invention may use a single microparticle or 2, 3, 4, 5, 6, 7, 8, 9, 10, 20, 30, 50, 100, 1,000, 5,000, 10,000, 100,000, 500,000 or 1,000,000 or more microparticles. If two or more microparticles are used, the microparticles may be the same. Alternatively, a mixture of different microparticles may be used.

Each microparticle may have one polynucleotide attached. Alternatively, each microparticle may have two or more polynucleotides, such as 3 or more, 4 or more, 5 or more. 6 or more. 7 or more, 8 or more, 9 or more, 10 or more, 20 or more, 30 or more, 50 or more, 100 or more, 500 or more. 1,000 or more. 5,000 or more. 10,000 or more. 100,000 or more. 1000,000 or more or 5000,000 or more polynucleotides, attached. A microparticle may be substantially or completed coated or covered with polynucleotide. A microparticle may have a polynucleotide attached over substantially all of or all of its surface. A microparticle may be attached to a polynucleotide via an adaptor. The adaptor may be a Y-adaptor or a hairpin adaptor (see below)

A polynucleotide. i.e. a single instance of an polynucleotide, may be attached to two or more microparticles. A polynucleotide, i.e. a single instance of an polynucleotide, may be attached to any number of the microparticles discussed above.

A microparticle is a microscopic particle whose size is typically measured in micrometres (μm). Microparticles may also known as microspheres or microbeads. The microparticle may be a nanoparticle. A nanoparticle is a microscopic particle whose size is typically measured in nanometres (nm).

A microparticle typically has a particle size of from about 0.001 μm to about 500 μm. For instance, a nanoparticle may have a particle size of from about 0.01 μm to about 200 μm or about 0.1 μm to about 100 μm. More often, a microparticle has a particle size of from about 0.5 μm to about 100 μm, or for instance from about 1 μm to about 50 μm. The microparticle may have a particle size of from about 1 nm to about 1000 nm, such as from about 10 nm to about 500 nm, about 20 nm to about 200 nm or from about 30 nm to about 100 nm.

A microparticle may be spherical or non-spherical. Spherical microparticles may be called microspheres. Non-spherical particles may for instance be plate-shaped, needle-shaped, irregular or tubular. The term "particle size" as used herein means the diameter of the particle if the particle is spherical or, if the particle is non-spherical, the volume-based particle size. The volume-based particle size is the diameter of the sphere that has the same volume as the non-spherical particle in question.

If two or more microparticles are used in the method, the average particle size of the microparticles may be any of the sizes discussed above, such as from about 0.5 μm to about 500 μm. A population of two or more microparticles preferably has a coefficient of variation (ratio of the standard deviation to the mean) of 10% or less, such as 5% or less or 2% or less.

Any method may be used to determine the size of the microparticle. Suitable methods include, but are not limited to, flow cytometry (see, for example, Chandler et al., J Thromb Haemost. 2011 June;9 (6): 1216-24).

The microparticle may be formed from any material. The microparticle is preferably formed from a ceramic, glass, silica, a polymer or a metal. The polymer may be a natural polymer, such as polyhydroxyalkanoate, dextran, polylactide, agarose, cellulose, starch or chitosan, or a synthetic polymer, such as polyurethane, polystyrene, poly (vinyl chloride), silane or methacrylate. Suitable microparticles are known in the art and are commercially available. Ceramic and glass microspheres are commercially available from 3MR. Silica and polymer microparticles are commercially available from EPRUI Nanoparticles & Microspheres Co. Ltd. Microparticles are also commercially available from Polysciences Inc., Bangs Laboratories Inc. and Life Technologies.

The microparticle may be solid. The microparticle may be hollow. The microparticle may be formed from polymer fibers.

The microparticle may be derived from the kit used to extract and isolate the polynucleotide.

The surface of the microparticle may interact with and attach the polynucleotide. The surface may naturally interact with the polynucleotide without functionalisation. The surface of the microparticle is typically functionalised to facilitate attachment of the polynucleotide. Suitable functionalisations are known in the art. For instance, the surface of the microparticle may be functionalised with a polyhistidine-tag (hexa histidine-tag. HIS-TAG®, HIS6 TAG® or HIS-TAG®). Ni-NTA, streptavidin, biotin, an oligonucleotide, a polynucleotide (such as DNA, RNA, PNA, GNA, TNA or LNA), carboxyl groups, quaternary amine groups, thiol groups, azide groups, alkyne groups, DIBO, lipid, FLAG-tag (FLAG octapeptide, polynucleotide binding proteins (including any of those discussed below), peptides, proteins, antibodies or antibody fragments. Antibody fragments are discussed in more detail below. The microparticle may also be functionalised with any of the linkers or groups discussed below with reference to attachment.

The microparticle may be functionalised with a molecule or group which specifically binds to the polynucleotide. In this instance, the polynucleotide which will be attached to the microparticle and delivered to the transmembrane pore may be called the target polynucleotide. This allows the microparticle to select or capture the target polynucleotide from a sample containing other polynucleotides. A molecule or group specifically binds to the target polynucleotide if it binds to the target polynucleotide with preferential or high affinity, but does not bind or binds with only low affinity to other or different polynucleotides. A molecule or group binds with preferential or high affinity if it binds with a Kd of $1\times10^{-6}$ M or less, more preferably $1\times10^{-7}$ M or less. $5\times10^{-8}$ M or less, more preferably $1\times10^{-8}$ M or less or more preferably $5\times10^{-9}$ M or less. A molecule or group binds with low affinity if it binds with a Kd of $1\times10^{-6}$ M or more, more preferably $1\times10^{-5}$ M or more, more preferably $1\times10^{-4}$ M or more, more preferably $1\times10^{-3}$ M or more, even more preferably $1\times10^{-2}$ M or more.

Preferably, the molecule or group binds to the target polynucleotide with an affinity that is at least 10 times, such as at least 50, at least 100, at least 200, at least 300, at least 400, at least 500, at least 1000 or at least 10,000 times, greater than its affinity for other polynucleotides. Affinity can be measured using known binding assays, such as those that make use of fluorescence and radioisotopes. Competitive binding assays are also known in the art. The strength of binding between peptides or proteins and polynucleotides can be measured using nanopore force spectroscopy as described in Hornblower et al., Nature Methods. 4:315-317. (2007).

The microparticle may be functionalised with an oligonucleotide or a polynucleotide (such as any of those discussed above) which specifically hybridises to the target polynucleotide or comprises a portion or region which is complementary to a portion or region of the target polynucleotide. This allows the microparticle to select or capture the target polynucleotide from a sample containing other polynucleotides. An oligonucleotide or polynucleotide specifically hybridises to a target polynucleotide when it hybridises with preferential or high affinity to the target polynucleotide but does not substantially hybridise, does not hybridise or hybridises with only low affinity to other polynucleotide. An oligonucleotide or polynucleotide specifically hybridises if it hybridises to the target polynucleotide with a melting temperature (Tm) that is at least 2° C., such as at least 3° C., at least 4° C., at least 5° C., at least 6° C., at least 7° C., at least 8° C., at least 9° C. or at least 10° C., greater than its Tm for other sequences. More preferably, the oligonucleotide or polynucleotide hybridises to the target polynucleotide with a Tm that is at least 2° C., such as at least 3° C. at least 4° C., at least 5° C. at least 6° C., at least 7° C., at least 8° C., at least 9° C. at least 10° C., at least 20° C. at least 30° C. or at least 40° C., greater than its I'm for other nucleic acids. Preferably, the oligonucleotide or polynucleotide hybridises to the target polynucleotide with a Tm that is at least 2° C., such as at least 3° C., at least 4° C., at least 5° C., at least 6° C., at least 7° C., at least 8° C., at least 9° C., at least 10° C., at least 20° C., at least 30° C. or at least 40° C. greater than its Tm for a sequence which differs from the target polynucleotide by one or more nucleotides, such as by 1, 2, 3, 4 or 5 or more nucleotides. The oligonucleotide or polynucleotide typically hybridises to the target polynucleotide with a $T_m$ of at least 90° C., such as at least 92° C. or at least 95° C. $T_m$ can be measured experimentally using known techniques, including the use of DNA microarrays, or can be calculated using publicly available $T_m$ calculators, such as those available over the internet.

Conditions that permit the hybridisation are well-known in the art (for example, Sambrook et al., 2001, Molecular Cloning: a laboratory manual. 3rd edition, Cold Spring Harbour Laboratory Press; and Current Protocols in Molecular Biology, Chapter 2, Ausubel et al., Eds., Greene Publishing and Wiley-Interscience, New York (1995)) Hybridisation can be carried out under low stringency conditions, for example in the presence of a buffered solution of 30 to 35% formamide, 1 M NaCl and 1% SDS (sodium dodecyl sulfate) at 37° C. followed by a 20 wash in from 1X (0, 1650 M Na⁺) to 2X (0.33 M Na⁺) SSC (standard sodium citrate) at 50° C. Hybridisation can be carried out under moderate stringency conditions, for example in the presence of a buffer solution of 40 to 45% formamide. 1 M NaCl, and 1% SDS at 37° C., followed by a wash in from 0.5X (0.0825 M Na') to 1X (0.1650 M Na⁺) SSC at 55° C. Hybridisation can be carried out under high stringency conditions, for example in the presence of a buffered solution of 50% formamide, 1 M NaCl, 1% SDS at 37° C., followed by a wash in 0.1X (0.0165 M Na⁺) SSC at 60° C.

The oligonucleotide or polynucleotide may comprise a portion or region which is substantially complementary to a portion or region of the target polynucleotide. The region or portion of the oligonucleotide or polynucleotide may therefore have 1, 2, 3, 4, 5, 6, 7, 8, 9, 10 or more mismatches across a region of 5, 10, 15, 20, 21, 22, 30, 40 or 50 nucleotides compared with the portion or region in the target polynucleotide.

A portion of region is typically 50 nucleotides or fewer, such as 40 nucleotides or fewer, 30 nucleotides or fewer, 20 nucleotides or fewer, 10 nucleotides or fewer or 5 nucleotides or fewer.

The microparticle is preferably paramagnetic or magnetic. The microparticle preferably comprises a paramagnetic or a superparamagnetic material or a paramagnetic or a superparamagnetic metal, such as iron. Any suitable magnetic microparticle may be used. For instance, magnetic beads commercially available from, for instance, Clontech, Promega, Invitrogen ThermoFisher Scientific and NEB, may be used. In some embodiments, the microparticle comprises a magnetic particle with an organic group such as a metal-chelating group, such as nitrilotriacetic acid (NTA), attached. The organic component may, for instance, comprise a group selected from —C(=O)O—, —C—O—C—, —C(=O)—, —NH—, —C(=O)—NH, —C(=O)—CH$_2$—I, —S(=O)$_2$— and —S—. The organic component may comprise a metal chelating group, such as NTA (nitrilotriacetic acid). Usually, a metal such as gold, iron, nickel or cobalt is also attached to the metal-chelating group. Magnetic beads of this sort are commonly used for capturing His-tagged proteins, but are also suitable for use in the invention.

The microparticle is most preferably a HIS-TAGR DYNABEAD® which is commercially available from Life Technologies. Mag Strep beads from IBA. Streptavidin magnetic beads from NEB. Solid Phase Reversible Immobilization (SPRI®) beads or Agencourt AMPure XP beads from Beckman Coulter or DYNADEADSR MYONE™ Streptavidin C1 (ThermoFisher Scientific).

Coupling

The target polynucleotide preferably comprises one or more anchors which are capable of coupling to the membrane. The method preferably further comprises coupling the target polynucleotide to the membrane using the one or more anchors.

The anchor comprises a group which couples (or binds) to the polynucleotide and a group which couples (or binds) to the membrane. Each anchor may covalently couple (or bind) to the polynucleotide and/or the membrane.

The polynucleotide may be coupled to the membrane using any number of anchors, such as 2, 3, 4 or more anchors. For instance, the polynucleotide may be coupled to the membrane using two anchors each of which separately couples (or binds) to both the polynucleotide and membrane.

The one or more anchors may comprise one or more molecular brakes. Each anchor may comprise one or more molecular brakes. The molecular brake(s) may be any of those discussed below.

If the membrane is an amphiphilic layer, such as a triblock copolymer membrane, the one or more anchors preferably comprise a polypeptide anchor present in the membrane and/or a hydrophobic anchor present in the membrane. The hydrophobic anchor is preferably a lipid, fatty acid, sterol, carbon nanotube, polypeptide, protein or amino acid, for example cholesterol, palmitate or tocopherol. In preferred embodiments, the one or more anchors are not the pore.

The components of the membrane, such as the amphiphilic molecules, copolymer or lipids, may be chemically-modified or functionalised to form the one or more anchors. Examples of suitable chemical modifications and suitable ways of functionalising the components of the membrane are discussed in more detail below. Any proportion of the membrane components may be functionalised, for example at least 0.01%, at least 0.1%, at least 1%, at least 10%, at least 25%, at least 50% or 100%.

The polynucleotide may be coupled directly to the membrane. The one or more anchors used to couple the polynucleotide to the membrane preferably comprise a linker. The one or more anchors may comprise one or more, such as 2, 3, 4 or more, linkers. One linker may be used to couple more than one, such as 2, 3, 4 or more, polynucleotides to the membrane.

Preferred linkers include, but are not limited to, polymers, such as polynucleotides, polyethylene glycols (PEGs), polysaccharides and polypeptides. These linkers may be linear, branched or circular. For instance, the linker may be a circular polynucleotide. The polynucleotide may hybridise to a complementary sequence on the circular polynucleotide linker.

The one or more anchors or one or more linkers may comprise a component that can be cut or broken down, such as a restriction site or a photolabile group.

Functionalised linkers and the ways in which they can couple molecules are known in the art. For instance, linkers functionalised with maleimide groups will react with and attach to cysteine residues in proteins. In the context of this invention, the protein may be present in the membrane, may be the polynucleotide itself or may be used to couple (or bind) to the polynucleotide. This is discussed in more detail below.

Crosslinkage of polynucleotides can be avoided using a "lock and key" arrangement. Only one end of each linker may react together to form a longer linker and the other ends of the linker each react with the polynucleotide or membrane respectively. Such linkers are described in International Application No PCT/GB10/000132 (published as WO 2010/086602).

The use of a linker is preferred in the sequencing embodiments discussed below. If a polynucleotide is permanently coupled directly to the membrane in the sense that it does not uncouple when interacting with the pore, then some sequence data will be lost as the sequencing run cannot continue to the end of the polynucleotide due to the distance between the membrane and the pore. If a linker is used, then the polynucleotide can be processed to completion.

The coupling may be permanent or stable. In other words, the coupling may be such that the polynucleotide remains coupled to the membrane when interacting with the pore.

The coupling may be transient. In other words, the coupling may be such that the polynucleotide may decouple from the membrane when interacting with the pore. For certain applications, such as aptamer detection and polynucleotide sequencing, the transient nature of the coupling is preferred. If a permanent or stable linker is attached directly to either the 5' or 3' end of a polynucleotide and the linker is shorter than the distance between the membrane and the transmembrane pore's channel, then some sequence data will be lost as the sequencing run cannot continue to the end of the polynucleotide. If the coupling is transient, then when the coupled end randomly becomes free of the membrane, then the polynucleotide can be processed to completion. Chemical groups that form permanent/stable or transient links are discussed in more detail below. The polynucleotide may be transiently coupled to an amphiphilic layer or triblock copolymer membrane using cholesterol or a fatty acyl chain. Any fatty acyl chain having a length of from 6 to 30 carbon atom, such as hexadecanoic acid, may be used.

In preferred embodiments, a polynucleotide, such as a nucleic acid, is coupled to an amphiphilic layer such as a triblock copolymer membrane or lipid bilayer Coupling of nucleic acids to synthetic lipid bilayers has been carried out previously with various different tethering strategies. These are summarised in Table 3 below.

TABLE 3

| Anchor comprising | Type of coupling | Reference |
|---|---|---|
| Thiol | Stable | Yoshina-Ishii, C. and S. G. Boxer (2003). "Arrays of mobile tethered vesicles on supported lipid bilayers." *J Am Chem Soc* 125(13): 3696-7. |
| Biotin | Stable | Nikolov, V., R. Lipowsky, et al. (2007). "Behavior of giant vesicles with anchored D NA molecules." *Biophys J* 92(12): 4356-68 |
| Cholesterol | Transient | Pfeiffer, I. and F. Hook (2004). "Bivalent cholesterol-based coupling of oligonucletides to lipid membrane assemblies." *J Am Chem Soc* 126(33): 10224-5 |
| Surfactant (e.g. Lipid, Palmitate, etc) | Stable | van Lengerich, B., R. J. Rawle, et al. "Covalent attachment of lipid vesicles to a fluid-supported bilayer allows observation of DNA-mediated vesicle interactions." *Langmuir* 26(11): 8666-72 |

Synthetic polynucleotides and/or linkers may be functionalised using a modified phosphoramidite in the synthesis reaction, which is easily compatible for the direct addition of suitable anchoring groups, such as cholesterol, tocopherol, palmitate, thiol, lipid and biotin groups. These different attachment chemistries give a suite of options for attachment to polynucleotides. Each different modification group couples the polynucleotide in a slightly different way and coupling is not always permanent so giving different dwell times for the polynucleotide to the membrane. The advantages of transient coupling are discussed above.

Coupling of polynucleotides to a linker or to a functionalised membrane can also be achieved by a number of other means provided that a complementary reactive group or an anchoring group can be added to the polynucleotide. The addition of reactive groups to either end of a polynucleotide has been reported previously. A thiol group can be added to the 5' of ssDNA or dsDNA using T4 polynucleotide kinase and ATPγS (Grant, G. P. and P. Z. Qin (2007). "A facile method for attaching nitroxide spin labels at the 5' terminus of nucleic acids." Nucleic Acids Res 35 (10): e77). An azide group can be added to the 5'-phosphate of ssDNA or dsDNA using T4 polynucleotide kinase and γ-[2-Azidoethyl]-ATP or γ-[6-Azidohexyl]-ATP. Using thiol or Click chemistry a tether, containing either a thiol, iodoacetamide OPSS or maleimide group (reactive to thiols) or a DIBO (dibenzocyclooxtyne) or alkyne group (reactive to azides), can be covalently attached to the polynucleotide. A more diverse selection of chemical groups, such as biotin, thiols and fluorophores, can be added using terminal transferase to incorporate modified oligonucleotides to the 3' of ssDNA (Kumar, A., P. Tchen, et al. (1988). "Nonradioactive labeling of synthetic oligonucleotide probes with terminal deoxynucleotidyl transferase." Anal Biochem 169 (2): 376-82). Streptavidin/biotin and/or streptavidin/desthiobiotin coupling may be used for any other polynucleotide. The Examples below describes how a polynucleotide can be coupled to a membrane using streptavidin/biotin and streptavidin/desthiobiotin. It may also be possible that anchors may be directly added to polynucleotides using terminal transferase with suitably modified nucleotides (e.g., cholesterol or palmitate).

The one or more anchors preferably couple the polynucleotide to the membrane via hybridisation. The hybridisation may be present in any part of the one or more anchors, such as between the one or more anchors and the polynucleotide, within the one or more anchors or between the one or more anchors and the membrane. Hybridisation in the one or more anchors allows coupling in a transient manner as discussed above. For instance, a linker may comprise two or more polynucleotides, such as 3, 4 or 5 polynucleotides, hybridised together. The one or more anchors may hybridise to the polynucleotide. The one or more anchors may hybridise directly to the polynucleotide, directly to a Y adaptor and/or leader sequence attached to the polynucleotide or directly to a hairpin loop adaptor attached to the polynucleotide (as discussed in more detail below). Alternatively, the one or more anchors may be hybridised to one or more, such as 2 or 3, intermediate polynucleotides (or "splints") which are hybridised to the polynucleotide, to a Y adaptor and/or leader sequence attached to the polynucleotide or to a hairpin loop adaptor attached to the polynucleotide (as discussed in more detail below).

The one or more anchors may comprise a single stranded or double stranded polynucleotide. One part of the anchor may be ligated to a single stranded or double stranded polynucleotide analyte. Ligation of short pieces of ssDNA have been reported using T4 RNA ligase I (Troutt, A. B., M. G. McHeyzer-Williams, et al. (1992). "Ligation-anchored PCR: a simple amplification technique with single-sided specificity." Proc Natl Acad Sci USA 89 (20): 9823-5). Alternatively, either a single stranded or double stranded polynucleotide can be ligated to a double stranded polynucleotide and then the two strands separated by thermal or chemical denaturation. To a double stranded polynucleotide, it is possible to add either a piece of single stranded polynucleotide to one or both of the ends of the duplex, or a double stranded polynucleotide to one or both ends. For addition of single stranded polynucleotides to the double stranded polynucleotide, this can be achieved using T4 RNA ligase I as for ligation to other regions of single stranded polynucleotides. For addition of double stranded polynucleotides to a double stranded polynucleotide then ligation can be "blunt-ended", with complementary 3' dA/dT tails on the polynucleotide and added polynucleotide respectively (as is routinely done for many sample prep applications to prevent concatemer or dimer formation) or using "sticky-ends" generated by restriction digestion of the polynucleotide and ligation of compatible adapters. Then, when the duplex is melted, each single strand will have either a 5' or 3' modification if a single stranded polynucleotide was used for ligation or a modification at the 5' end, the 3' end or both if a double stranded polynucleotide was used for ligation.

If the polynucleotide is a synthetic strand, the one or more anchors can be incorporated during the chemical synthesis of the polynucleotide. For instance, the polynucleotide can be synthesised using a primer having a reactive group attached to it.

Adenylated polynucleotides are intermediates in ligation reactions, where an adenosine-monophosphate is attached to the 5'-phosphate of the polynucleotide. Various kits are available for generation of this intermediate, such as the 5' DNA Adenylation Kit from NEB. By substituting ATP in the reaction for a modified nucleotide triphosphate, then addition of reactive groups (such as thiols, amines, biotin, azides, etc) to the 5' of a polynucleotide can be possible. It may also be possible that anchors could be directly added to polynucleotides using a 5' DNA adenylation kit with suitably modified nucleotides (e.g. cholesterol or palmitate).

A common technique for the amplification of sections of genomic DNA is using polymerase chain reaction (PCR). Here, using two synthetic oligonucleotide primers, a number of copies of the same section of DNA can be generated, where for each copy the 5' of each strand in the duplex will be a synthetic polynucleotide. Single or multiple nucleotides can be added to 3' end of single or double stranded DNA by employing a polymerase. Examples of polymerases which could be used include, but are not limited to, Terminal Transferase. Klenow and *E. coli* Poly (A) polymerase). By substituting ATP in the reaction for a modified nucleotide triphosphate then anchors, such as cholesterol, thiol, amine, azide, biotin or lipid, can be incorporated into double stranded polynucleotides. Therefore, each copy of the amplified polynucleotide will contain an anchor.

Ideally, the polynucleotide is coupled to the membrane without having to functionalise the polynucleotide. This can be achieved by coupling the one or more anchors, such as a polynucleotide binding protein or a chemical group, to the membrane and allowing the one or more anchors to interact with the polynucleotide or by functionalizing the membrane. The one or more anchors may be coupled to the membrane by any of the methods described herein. In particular, the one or more anchors may comprise one or more linkers, such as maleimide functionalised linkers.

In this embodiment, the polynucleotide is typically RNA, DNA, PNA, TNA or LNA and may be double or single stranded. This embodiment is particularly suited to genomic DNA polynucleotides.

The one or more anchors can comprise any group that couples to, binds to or interacts with single or double stranded polynucleotides, specific nucleotide sequences within the polynucleotide or patterns of modified nucleotides within the polynucleotide, or any other ligand that is present on the polynucleotide.

Suitable binding proteins for use in anchors include, but are not limited to, *E. coli* single stranded binding protein. P5 single stranded binding protein, T4 gp32 single stranded binding protein, the TOPO V dsDNA binding region, human histone proteins, *E. coli* HU DNA binding protein and other archaeal, prokaryotic or eukaryotic single stranded or double stranded polynucleotide (or nucleic acid) binding proteins, including those listed below.

The specific nucleotide sequences could be sequences recognised by transcription factors, ribosomes, endonucleases, topoisomerases or replication initiation factors. The patterns of modified nucleotides could be patterns of methylation or damage.

The one or more anchors can comprise any group which couples to, binds to, intercalates with or interacts with a polynucleotide. The group may intercalate or interact with the polynucleotide via electrostatic, hydrogen bonding or Van der Waals interactions Such groups include a lysine monomer, poly-lysine (which will interact with ssDNA or dsDNA), ethidium bromide (which will intercalate with dsDNA), universal bases or universal nucleotides (which can hybridise with any polynucleotide) and osmium complexes (which can react to methylated bases). A polynucleotide may therefore be coupled to the membrane using one or more universal nucleotides attached to the membrane. Each universal nucleotide may be coupled to the membrane using one or more linkers. The universal nucleotide preferably comprises one of the following nucleobases: hypoxanthine, 4-nitroindole, 5-nitroindole. 6-nitroindole, formylindole, 3-nitropyrrole, nitroimidazole. 4-nitropyrazole. 4-nitrobenzimidazole, 5-nitroindazole, 4-aminobenzimidazole or phenyl (C6-aromatic ring). The universal nucleotide more preferably comprises one of the following nucleosides: 2'-deoxvinosine, inosine, 7-deaza-2-deoxyinosine, 7-deaza-inosine, 2-aza-deoxyinosine, 2-aza-inosine, 2-O'-methyl-inosine, 4-nitroindole 2'-deoxyribonucleoside, 4-nitroindole ribonucleoside, 5-nitroindole 2'-deoxyribonucleoside, 5-nitroindole ribonucleoside, 6-nitroindole 2'-deoxyribonucleoside, 6-nitroindole ribonucleoside, 3-nitropyrrole 2'-deoxyribonucleoside, 3-nitropyrrole ribonucleoside, an acyclic sugar analogue of hypoxanthine, nitroimidazole 2'-deoxyribonucleoside, nitroimidazole ribonucleoside, 4-nitropyrazole 2'-deoxyribonucleoside. 4-nitropyrazole ribonucleoside, 4-nitrobenzimidazole 2'-deoxyribonucleoside, 4-nitrobenzimidazole ribonucleoside, 5-nitroindazole 2'-deoxyribonucleoside, 5-nitroindazole ribonucleoside, 4-aminobenzimidazole 2'-deoxyribonucleoside. 4-aminobenzimidazole ribonucleoside, phenyl C-ribonucleoside, phenyl C-2"-deoxyribosyl nucleoside, 2'-deoxynebularine, 2'-deoxyisoguanosine, K-2'-deoxyribose, P-2'-deoxyribose and pyrrolidine. The universal nucleotide more preferably comprises 2-deoxyinosine. The universal nucleotide is more preferably IMP or dIMP. The universal nucleotide is most preferably dPMP (2'-Deoxy-P-nucleoside monophosphate) or dKMP (N6-methoxy-2, 6-diaminopurine monophosphate).

The one or more anchors may couple to (or bind to) the polynucleotide via Hoogsteen hydrogen bonds (where two nucleobases are held together by hydrogen bonds) or reversed Hoogsteen hydrogen bonds (where one nucleobase is rotated through 180° with respect to the other nucleobase). For instance, the one or more anchors may comprise one or more nucleotides, one or more oligonucleotides or one or more polynucleotides which form Hoogsteen hydrogen bonds or reversed Hoogsteen hydrogen bonds with the polynucleotide. These types of hydrogen bonds allow a third polynucleotide strand to wind around a double stranded helix and form a triplex. The one or more anchors may couple to (or bind to) a double stranded polynucleotide by forming a triplex with the double stranded duplex.

In this embodiment at least 1%, at least 10%, at least 25%, at least 50% or 100% of the membrane components may be functionalised.

Where the one or more anchors comprise a protein, they may be able to anchor directly into the membrane without further functonalisation, for example if it already has an external hydrophobic region which is compatible with the membrane. Examples of such proteins include, but are not limited to, transmembrane proteins, intramembrane proteins and membrane proteins. Alternatively the protein may be expressed with a genetically fused hydrophobic region which is compatible with the membrane Such hydrophobic protein regions are known in the art.

The one or more anchors are preferably mixed with the polynucleotide before delivery to the membrane, but the one or more anchors may be contacted with the membrane and subsequently contacted with the polynucleotide.

In another aspect the polynucleotide may be functionalised, using methods described above, so that it can be recognised by a specific binding group. Specifically the polynucleotide may be functionalised with a ligand such as biotin (for binding to streptavidin), amylose (for binding to maltose binding protein or a fusion protein). Ni-NTA (for binding to poly-histidine or poly-histidine tagged proteins) or peptides (such as an antigen).

According to a preferred embodiment, the one or more anchors may be used to couple a polynucleotide to the membrane when the polynucleotide is attached to a leader sequence which preferentially threads into the pore. Leader sequences are discussed in more detail below. Preferably, the polynucleotide is attached (such as ligated) to a leader sequence which preferentially threads into the pore. Such a leader sequence may comprise a homopolymeric polynucleotide or an abasic region. The leader sequence is typically designed to hybridise to the one or more anchors either directly or via one or more intermediate polynucleotides (or splints). In such instances, the one or more anchors typically comprise a polynucleotide sequence which is complementary to a sequence in the leader sequence or a sequence in the one or more intermediate polynucleotides (or splints). In such instances, the one or more splints typically comprise a polynucleotide sequence which is complementary to a sequence in the leader sequence.

Any of the methods discussed above for coupling polynucleotides to membranes, such as amphiphilic layers, can of course be applied to other polynucleotide and membrane combinations. In some embodiments, an amino acid, peptide, polypeptide or protein is coupled to an amphiphilic layer, such as a triblock copolymer layer or lipid bilayer. Various methodologies for the chemical attachment of such polynucleotides are available. An example of a molecule used in chemical attachment is EDC (1-ethyl-3-[3-dimethylaminopropyl]carbodiimide hydrochloride). Reactive groups can also be added to the 5' of polynucleotides using commercially available kits (Thermo Pierce, Part No. 22980). Suitable methods include, but are not limited to, transient affinity attachment using histidine residues and Ni-NTA, as well as more robust covalent attachment by reactive cysteines, lysines or non natural amino acids.

Polynucleotide Characterisation

The method of the invention involves characterising a target polynucleotide. After the target polynucleotide is contacted with the pore, one or more measurements which are indicative of one or more characteristics of the target polynucleotide are taken as the polynucleotide moves with respect to the pore.

Any number of polynucleotides can be investigated. For instance, the method of the invention may concern characterising two or more polynucleotides, such as 3 or more, 4 or more. 5 or more, 6 or more, 7 or more. 8 or more, 9 or more, 10 or more, 20 or more. 30 or more, 50 or more, 100 or more, 500 or more, 1,000 or more, 5,000 or more, 10,000 or more, 100,000 or more. 1000,000 or more or 5000,000 or more, polynucleotides. The two or more polynucleotides may be delivered using the same microparticle or different microparticles.

If two or more polynucleotides are characterised, they may be different from one another. The two or more polynucleotides may be two or more instances of the same polynucleotide. This allows proof reading.

The polynucleotides can be naturally occurring or artificial. For instance, the method may be used to verify the sequence of two or more manufactured oligonucleotides. The methods are typically carried out in vitro.

The method may involve measuring two, three, four or five or more characteristics of each polynucleotide. The one or more characteristics are preferably selected from (i) the length of the polynucleotide. (ii) the identity of the polynucleotide, (iii) the sequence of the polynucleotide. (iv) the secondary structure of the polynucleotide and (v) whether or not the polynucleotide is modified. Any combination of (i) to (v) may be measured in accordance with the invention, such as {i}, {ii}, {iii}, {iv}, {v}, {i,ii}, {i,ii}, {i,iv}, {i,v}, {ii,iii)}, {ii,iv}, {ii,v}; {iii,iv}, {ii,v}, {iv,v}, {i,ii,iii}, {i,ii,v}, {i,ii,iv}, {i, iii,iv}, {i,iii,v}, {i,iv,v}, {ii,iii,iv}, {ii,iii,v}, {ii,iv,v}, {iii,iv,v}, {i,ii,iii,v}, {i,ii,iv,v}, {i,iii,iv,v}, {ii,iii,iv,v} or {i,ii,iii,iv,v}.

For (i), the length of the polynucleotide may be measured for example by determining the number of interactions between the polynucleotide and the pore or the duration of interaction between the polynucleotide and the pore.

For (ii), the identity of the polynucleotide may be measured in a number of ways. The identity of the polynucleotide may be measured in conjunction with measurement of the sequence of the polynucleotide or without measurement of the sequence of the polynucleotide. The former is straightforward: the polynucleotide is sequenced and thereby identified. The latter may be done in several ways. For instance, the presence of a particular motif in the polynucleotide may be measured (without measuring the remaining sequence of the polynucleotide). Alternatively, the measurement of a particular electrical and/or optical signal in the method may identify the polynucleotide as coming from a particular source.

For (iii), the sequence of the polynucleotide can be determined as described previously. Suitable sequencing methods, particularly those using electrical measurements, are described in Stoddart D et al., Proc Natl Acad Sci, 12: 106 (19): 7702-7, Lieberman KR et al. J Am Chem Soc. 2010: 132 (50): 17961-72, and International Application WO 2000/28312.

For (iv), the secondary structure may be measured in a variety of ways. For instance, if the method involves an electrical measurement, the secondary structure may be measured using a change in dwell time or a change in current flowing through the pore. This allows regions of single-stranded and double-stranded polynucleotide to be distinguished.

For (v), the presence or absence of any modification may be measured. The method preferably comprises determining whether or not the polynucleotide is modified by methylation, by oxidation, by damage, with one or more proteins or with one or more labels, tags or spacers. Specific modifications will result in specific interactions with the pore which can be measured using the methods described below. For instance, methylcyotsine may be distinguished from cytosine on the basis of the current flowing through the pore during its interaction with each nucleotide.

The methods may be carried out using any apparatus that is suitable for investigating a membrane/pore system in which a pore is present in a membrane. The method may be carried out using any apparatus that is suitable for transmembrane pore sensing. For example, the apparatus comprises a chamber comprising an aqueous solution and a barrier that separates the chamber into two sections. The barrier typically has an aperture in which the membrane containing the pore is formed. Alternatively the barrier forms the membrane in which the pore is present.

The methods may be carried out using the apparatus described in International Application No. PCT/GB08/000562 (WO 2008/102120).

A variety of different types of measurements may be made. This includes without limitation: electrical measurements and optical measurements. A suitable optical method involving the measurement of fluorescence is disclosed by J. Am. Chem. Soc. 2009, 131 1652-1653. Possible electrical measurements include: current measurements, impedance measurements, tunnelling measurements (Ivanov AP et al., Nano Lett. 2011 Jan. 12: 11 (1): 279-85), and FET measurements (International Application WO 2005/124888). Optical measurements may be combined with electrical measurements (Soni GV et al., Rev Sci Instrum. 2010 January: 81 (1): 014301). The measurement may be a transmembrane current measurement such as measurement of ionic current flowing through the pore.

Electrical measurements may be made using standard single channel recording equipment as describe in Stoddart D et al., Proc Natl Acad Sci, 12;106 (19): 7702-7, Lieberman KR et al. J Am Chem Soc. 2010: 132 (50): 17961-72, and International Application WO 2000/28312. Alternatively, electrical measurements may be made using a multi-channel system, for example as described in International Application WO 2009/077734 and International Application WO 2011/067559.

The method is preferably carried out with a potential applied across the membrane. The applied potential may be a voltage potential. Alternatively, the applied potential may be a chemical potential. An example of this is using a salt gradient across a membrane, such as an amphiphilic layer. A salt gradient is disclosed in Holden et al., J Am Chem Soc. 2007 Jul. 11; 129 (27): 8650-5. In some instances, the current passing through the pore as a polynucleotide moves with respect to the pore is used to estimate or determine the sequence of the polynucleotide. This is strand sequencing.

The methods may involve measuring the current passing through the pore as the polynucleotide moves with respect to the pore. Therefore the apparatus may also comprise an electrical circuit capable of applying a potential and measuring an electrical signal across the membrane and pore. The methods may be carried out using a patch clamp or a voltage clamp. The methods preferably involve the use of a voltage clamp.

The methods of the invention may involve the measuring of a current passing through the pore as the polynucleotide moves with respect to the pore. Suitable conditions for measuring ionic currents through transmembrane protein pores are known in the art and disclosed in the Example. The method is typically carried out with a voltage applied across the membrane and pore. The voltage used is typically from +5 V to −5 V, such as from +4 V to −4 V, +3 V to −3 V or +2 V to −2 V. The voltage used is typically from −600 mV to +600 mV or −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl), caesium chloride (CsCl) or a mixture of potassium ferrocyanide and potassium ferricyanide is typically used. KCl, NaCl and a mixture of potassium ferrocyanide and potassium ferricyanide are preferred. The charge carriers may be asymmetric across the membrane. For instance, the type and/or concentration of the charge carriers may be different on each side of the membrane.

The salt concentration may be at saturation. The salt concentration may be 3 M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

The methods are typically carried out in the presence of a buffer. In the exemplary apparatus discussed above, the buffer is present in the aqueous solution in the chamber. Any buffer may be used in the method of the invention. Typically, the buffer is phosphate buffer. Other suitable buffers are HEPES and Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods may be carried out at from 0° C. to 100° C., from 15° C. to 95° C., from 16° C. to 90° C. from 17° C. to 85° C. from 18° C. to 80° C., 19° C. to 70° C., or from 20° C. to 60° C. The methods are typically carried out at room temperature. The methods are optionally carried out at a temperature that supports enzyme function, such as about 37° C.

Molecular Brake

The method comprises contacting the target polynucleotide with a molecular brake which controls the movement of the target polynucleotide through the pore. Any molecular brake may be used including any of those disclosed in International Application No. PCT/GB2014/052737 (published as WO 2015/110777).

The molecular brake is preferably a polynucleotide binding protein. The polynucleotide binding protein may be any protein that is capable of binding to the polynucleotide and controlling its movement through the pore. It is straightforward in the art to determine whether or not a protein binds to a polynucleotide. The protein typically interacts with and modifies at least one property of the polynucleotide. The protein may modify the polynucleotide by cleaving it to form individual nucleotides or shorter chains of nucleotides, such as di-or trinucleotides. The moiety may modify the polynucleotide by orienting it or moving it to a specific position, i.e. controlling its movement.

The polynucleotide binding protein preferably is able to slip, slide or actively move along the polynucleotide when under force (e.g. from an applied electrical field) and in contact with a nanopore. The polynucleotide binding protein is preferably one that does not immediately disengage from the polynucleotide when brought into contact with a nanopore. The polynucleotide binding protein is preferably not covalently joined to the polynucleotide, or otherwise locked to the polynucleotide in a manner that prevents the polynucleotide moving relative to the polynucleotide and through a nanopore in contact with the polynucleotide binding protein.

The polynucleotide binding protein is preferably derived from a polynucleotide handling enzyme. A polynucleotide handling enzyme is a polypeptide that is capable of interacting with and modifying at least one property of a polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide handling enzyme does not need to display enzymatic activity as long as it is capable of binding the polynucleotide and controlling its movement through the pore. For instance, the enzyme may be modified to remove its enzymatic activity or may be used under conditions which prevent it from acting as an enzyme. Such conditions are discussed in more detail below.

The polynucleotide handling enzyme is preferably derived from a nucleolytic enzyme. The polynucleotide handling enzyme used in the construct of the enzyme is more preferably derived from a member of any of the Enzyme Classification (EC) groups 3, 1.11, 3.1.13, 3.1.14, 3.1.15, 3.1.16, 3.1.21, 3.1.22, 3.1.25, 3.1.26, 3.1.27, 3.1.30 and 3.1.31. The enzyme may be any of those disclosed in International Application No. PCT/GB10/000133 (published as WO 2010/086603).

Preferred enzymes are polymerases, exonucleases, helicases, translocases and topoisomerases, such as gyrases. Suitable enzymes include, but are not limited to, exonuclease I from *E. coli* (SEQ ID NO. 11), exonuclease III enzyme from *E. coli* (SEQ ID NO: 13), RecJ from *T.*

*thermophilus* (SEQ ID NO: 15) and bacteriophage lambda exonuclease (SEQ ID NO: 17). TatD exonuclease and variants thereof. Three subunits comprising the sequence shown in SEQ ID NO: 15 or a variant thereof interact to form a trimer exonuclease. The polymerase may be PYROPHAGER 3173 DNA Polymerase (which is commercially available from LUCIGEN®) Corporation). SD Polymerase (commercially available from BIORON®) or variants thereof. The enzyme is preferably Phi29 DNA polymerase (SEQ ID NO: 9) or a variant thereof. The topoisomerase is preferably a member of any of the Moiety Classification (EC) groups 5.99.1.2 and 5.99.1.3.

The enzyme is most preferably derived from a helicase. The helicase may be or be derived from a Hel308 helicase, a RecD helicase, such as TraI helicase or a TrwC helicase, a XPD helicase or a Dda helicase. The helicase may be or be derived from Hel308 Mbu (SEQ ID NO: 18). Hel308 Csy (SEQ ID NO: 19). Hel308 Tga (SEQ ID NO: 20), Hel308 Mhu (SEQ ID NO: 21). TraI Eco (SEQ ID NO: 22), XPD Mbu (SEQ ID NO: 23) or a variant thereof.

The helicase may be any of the helicases, modified helicases or helicase constructs disclosed in International Application Nos. PCT/GB2012/052579 (published as WO 2013/057495): PCT/GB2012/053274 (published as WO 2013/098562); PCT/GB2012/053273 (published as WO2013098561), PCT/GB2013/051925 (published as WO 2014/013260): PCT/GB2013/051924 (published as WO 2014/013259); PCT/GB2013/051928 (published as WO 2014/013262) and PCT/GB2014/052736 (published as WO/2015/055981).

The helicase preferably comprises the sequence shown in SEQ ID NO: 25 (Trwe Cba) or as variant thereof, the sequence shown in SEQ ID NO: 18 (Hel308 Mbu) or a variant thereof or the sequence shown in SEQ ID NO: 24 (Dda) or a variant thereof. Variants may differ from the native sequences in any of the ways discussed below for transmembrane pores. A preferred variant of SEQ ID NO. 24 comprises (a) E94C and A360C or (b) E94C, A360C, C109A and C136A and then optionally (ΔM1)G1 (i.e. deletion of MI and then addition G1). It may also be termed M1G. Any of the variants discussed above may further comprise M1G.

The Dda helicase preferably comprises any of the modifications disclosed in International Application Nos. PCT/GB2014/052736 and PCT/GB2015/052916 (published as WO/2015/055981 and WO 2016/055777).

Any number of helicases may be used in accordance with the invention. For instance, 1, 2, 3, 4, 5, 6, 7, 8, 9, 10 or more helicases may be used. In some embodiments, different numbers of helicases may be used.

The method of the invention preferably comprises contacting the polynucleotide with two or more helicases. The two or more helicases are typically the same helicase. The two or more helicases may be different helicases.

The two or more helicases may be any combination of the helicases mentioned above. The two or more helicases may be two or more Dda helicases. The two or more helicases may be one or more Dda helicases and one or more TrwC helicases. The two or more helicases may be different variants of the same helicase.

The two or more helicases are preferably attached to one another. The two or more helicases are more preferably covalently attached to one another. The helicases may be attached in any order and using any method. Preferred helicase constructs for use in the invention are described in International Application Nos. PCT/GB2013/051925 (published as WO 2014/013260): PCT/GB2013/051924 (published as WO 2014/013259): PCT/GB2013/051928 (published as WO 2014/013262) and PCT/GB2014/052736.

A variant of SEQ ID NO: 9, 11, 13, 15, 17, 18, 19, 20, 21, 22, 23, 24 or 25 is an enzyme that has an amino acid sequence which varies from that of SEQ ID NO: 9, 11, 13, 15, 17, 18, 19, 20, 21, 22, 23, 24 or 25 and which retains polynucleotide binding ability. This can be measured using any method known in the art. For instance, the variant can be contacted with a polynucleotide and its ability to bind to and move along the polynucleotide can be measured. The variant may include modifications that facilitate binding of the polynucleotide and/or facilitate its activity at high salt concentrations and/or room temperature Variants may be modified such that they bind polynucleotides (i.e. retain polynucleotide binding ability) but do not function as a helicase (i.e. do not move along polynucleotides when provided with all the necessary components to facilitate movement, e.g. ATP and $Mg^{2+}$). Such modifications are known in the art. For instance, modification of the $Mg^{2+}$ binding domain in helicases typically results in variants which do not function as helicases. These types of variants may act as molecular brakes (see below).

Over the entire length of the amino acid sequence of SEQ ID NO: 9, 11, 13, 15, 17, 18, 19, 20, 21, 22, 23, 24 or 25, a variant will preferably be at least 50% homologous to that sequence based on amino acid similarity or identity. More preferably, the variant polypeptide may be at least 55%, at least 60%, at least 65%, at least 70%, at least 75%, at least 80%, at least 85%, at least 90% and more preferably at least 95%. 97% or 99% homologous based on amino acid similarity or identity to the amino acid sequence of SEQ ID NO: 9, 11, 13, 15, 17, 18, 19, 20, 21, 22, 23, 24 or 25 over the entire sequence. There may be at least 80%, for example at least 85%, 90% or 95%, amino acid similarity or identity over a stretch of 200 or more, for example 230, 250, 270, 280, 300, 400, 500, 600, 700, 800, 900 or 1000 or more, contiguous amino acids ("hard homology"). Homology is determined as described above. The variant may differ from the wild-type sequence in any of the ways discussed above with reference to SEQ ID NO: 2 and 4 above. The enzyme may be covalently attached to the pore. Any method may be used to covalently attach the enzyme to the pore.

A preferred molecular brake is TrwC Cba-Q594A (SEQ ID NO: 25 with the mutation Q594A). This variant does not function as a helicase (i.e. binds polynucleotides but does not move along them when provided with all the necessary components to facilitate movement, e.g. ATP and Mg2+).

In strand sequencing, the polynucleotide is translocated through the pore either with or against an applied potential. Exonucleases that act progressively or processively on double stranded polynucleotides can be used on the cis side of the pore to feed the remaining single strand through under an applied potential or the trans side under a reverse potential. Likewise, a helicase that unwinds the double stranded DNA can also be used in a similar manner. A polymerase may also be used. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential.

Any helicase may be used in the method. Helicases may work in two modes with respect to the pore. First, the method is preferably carried out using a helicase such that it moves the polynucleotide through the pore with the field resulting from the applied voltage. In this mode the 5' end of the polynucleotide is first captured in the pore, and the helicase moves the polynucleotide into the pore such that it is passed through the pore with the field until it finally translocates through to the trans side of the membrane. Alternatively, the method is preferably carried out such that a helicase moves the polynucleotide through the pore against the field resulting from the applied voltage. In this mode the 3' end of the polynucleotide is first captured in the pore, and the helicase moves the polynucleotide through the pore such that it is pulled out of the pore against the applied field until finally ejected back to the cis side of the membrane.

The method may also be carried out in the opposite direction. The 3' end of the polynucleotide may be first captured in the pore and the helicase may move the polynucleotide into the pore such that it is passed through the pore with the field until it finally translocates through to the trans side of the membrane.

When the helicase is not provided with the necessary components to facilitate movement or is modified to hinder or prevent its movement, it can bind to the polynucleotide and act as a brake slowing the movement of the polynucleotide when it is pulled into the pore by the applied field. In the inactive mode, it does not matter whether the polynucleotide is captured either 3' or 5' down, it is the applied field which pulls the polynucleotide into the pore towards the trans side with the enzyme acting as a brake. When in the inactive mode, the movement control of the polynucleotide by the helicase can be described in a number of ways including ratcheting, sliding and braking. Helicase variants which lack helicase activity can also be used in this way.

The polynucleotide may be contacted with the polynucleotide binding protein and the pore in any order. It is preferred that, when the polynucleotide is contacted with the polynucleotide binding protein, such as a helicase, and the pore, the polynucleotide firstly forms a complex with the protein. When the voltage is applied across the pore, the polynucleotide/protein complex then forms a complex with the pore and controls the movement of the polynucleotide through the pore.

Any steps in the method using a polynucleotide binding protein are typically carried out in the presence of free nucleotides or free nucleotide analogues and an enzyme cofactor that facilitates the action of the polynucleotide binding protein. The free nucleotides may be one or more of any of the individual nucleotides discussed above. The free nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP. CMP, UMP, dAMP, dTMP, dGMP or dCMP. The free nucleotides are preferably adenosine triphosphate (ATP). The enzyme cofactor is a factor that allows the construct to function. The enzyme cofactor is preferably a divalent metal cation. The divalent metal cation is preferably $Mg^{2+}$, $Mn^{2+}$, $Ca^{2+}$ or $Co^{2+}$. The enzyme cofactor is most preferably $Mg^{2+}$.

The molecular brakes may be any compound or molecule which binds to the polynucleotide and slows the movement of the polynucleotide through the pore. The molecular brake may be any of those discussed above. The molecular brake preferably comprises a compound which binds to the polynucleotide. The compound is preferably a macrocycle A macrocycle is a cyclic macromolecule or a macromolecular cyclic portin of a molecule. The macrocycle may comprise a ring having an inner circumference made up of a chain of at least 12 connections or atoms, up to 100, 500 or more connections or atoms. The inner diameter of the macrocycle ring (Van der Waals radius) may be in the range of from about 0.5 nm to less than about 10 nm, preferably in the range of from 1nm to 3 nm. Suitable macrocycles include, but are not limited to, cyclodextrins, calixarenes, cyclic peptides, crown ethers, cucurbiturils, pillararenes, derivatives thereof or a combination thereof. The cyclodextrin or derivative thereof may be any of those disclosed in Eliseev, A. V., and Schneider, H-J. (1994) J. Am. Chem. Soc 116, 6081-6088. The cyclodextrin is more preferably heptakis-6-amino-B-cyclodextrin (am;-βCD), 6-monodeoxy-6-monoamino-β-cyclodextrin ($am_1$-βCD) or heptakis-(6-deoxy-6-guanidino)-cyclodextrin ($gu_7$-βCD).

Spacers in the Target Polynucleotide

If a helicase is used in the invention, it may be stalled at one or more spacers as discussed in International Application No. PCT/GB2014/050175 (published as WO 2014/135838). Any configuration of one or more helicases and one or more spacers disclosed in the International Application may be used in this invention.

Double Stranded Polynucleotide

If the polynucleotide is double stranded, the method preferably further comprises providing the polynucleotide with a hairpin loop at one end of the polynucleotide. The method may comprise linking the two strands of the polynucleotide at one end with a hairpin loop. The molecular brake preferably separates the two strands of the target polynucleotide and controls the movement of the target polynucleotide through the pore one strand at a time. Linking and interrogating both strands on a double stranded construct in this way increases the efficiency and accuracy of characterisation. Hairpin loops are discussed above.

Leader Sequence

The polynucleotide may be provided with a leader sequence which preferentially threads into the pore. The leader sequence facilitates the method of the invention. The leader sequence is designed to preferentially thread into the transmembrane pore and thereby facilitate the movement of polynucleotide through the pore. The leader sequence can also be used to link the polynucleotide to the one or more anchors as discussed above.

The leader sequence typically comprises a polymer. The polymer is preferably negatively charged. The polymer is preferably a polynucleotide, such as DNA or RNA, a modified polynucleotide (such as abasic DNA). PNA, LNA, polyethylene glycol (PEG) or a polypeptide. The leader preferably comprises a polynucleotide and more preferably comprises a single stranded polynucleotide. The leader sequence can comprise any of the polynucleotides discussed above. The single stranded leader sequence most preferably comprises a single strand of DNA, such as a poly dT section. The leader sequence preferably comprises the one or more spacers.

The leader sequence can be any length, but is typically 10 to 150 nucleotides in length, such as from 20 to 150 nucleotides in length. The length of the leader typically depends on the transmembrane pore used in the method.

Y Adaptors

A double stranded polynucleotide may be provided with a Y adaptor at one end and a hairpin loop at the other end. The method of the invention may comprise attaching a Y adaptor to one end of a double stranded polynucleotide and attaching a hairpin loop at the other end. The Y adaptor and/or the hairpin adaptor are typically polynucleotide adaptors. They may be formed from any of the polynucleotides discussed above.

The Y adaptor typically comprises (a) a double stranded region and (b) a single stranded region or a region that is not complementary at the other end. The Y adaptor may be described as having an overhang if it comprises a single stranded region. The presence of a non-complementary region in the Y adaptor gives the adaptor its Y shape since the two strands typically do not hybridise to each other unlike the double stranded portion. The Y adaptor may comprise one or more anchors. Anchors are discussed in more detail above.

The Y adaptor preferably comprises a leader sequence which preferentially threads into the pore. Leader sequences are discussed above.

The Y adaptor preferably comprises a selectable binding moiety as discussed above. The Y adaptor and/or the selectable binding moiety may comprise a region that can be cut, nicked, cleaved or hydrolysed as discussed above.

The Y adaptor and/or the hairpin loop may be ligated to the polynucleotide using any method known in the art. One or both of the adaptors may be ligated using a ligase, such as T4 DNA ligase, E. coli DNA ligase, Taq DNA ligase, Tma DNA ligase and 9°N DNA ligase. Alternatively, the adaptors may be added to the polynucleotide using the methods of the invention discussed below.

In a preferred embodiment, the method comprises modifying the double stranded polynucleotide so that it comprises the Y adaptor at one end and the hairpin loop at the other end. Any manner of modification can be used. The method preferably comprises modifying the double stranded polynucleotide in accordance with the invention. This is discussed in more detail below. The methods of modification and characterisation may be combined in any way.

Adding Hairpin Loops and Leader Sequences

The double stranded polynucleotide may be provided with Y and hairpin loops by contacting the polynucleotide with a MuA transposase and a population of double stranded MuA substrates, wherein a proportion of the substrates in the population are Y adaptors comprising the leader sequence and wherein a proportion of the substrates in the population are hairpin loops. The transposase fragments the double stranded polynucleotide and ligates MuA substrates to one or both ends of the fragments. This produces a plurality of modified double stranded polynucleotides comprising the leader sequence at one end and the hairpin loop at the other. The modified double stranded polynucleotides may then be investigated using the method of the invention.

These MuA based methods are disclosed in International Application No. PCT/GB2014/052505 published as (WO 2015/022544). They are also discussed in detail in International Application No PCT/GB2015/050991.

Modified Polynucleotide Analytes

Before characterisation in accordance with the invention, the polynucleotide may be modified by contacting the polynucleotide with a polymerase and a population of free nucleotides under conditions in which the polymerase forms a modified polynucleotide using the polynucleotide as a template, wherein the polymerase replaces one or more of the nucleotide species in the polynucleotide with a different nucleotide species when forming the modified polynucleotide analyte. The modified polynucleotide may then be characterised in accordance with the invention. This type of modification is described in PCT Application No. PCT/GB2015/050483. Any of the polymerases discussed above may be used. The polymerase is preferably Klenow or 90 North.

Kits

The present invention also provides a kit for characterising a double stranded target polynucleotide. The kit comprises a hairpin loop capable of linking the two strands of the target polynucleotide at one end. Such loops are discussed above. The kit also comprises one or more species which control or decrease the formation of secondary structure by the target polynucleotide. Any of the species discussed above may be present in the kit.

The kit may further comprise a microparticle for delivering the polynucleotide to a transmembrane pore in a membrane. The kit may further comprise one or more anchors which are capable of coupling the polynucleotide to a membrane. The microparticle and one or more anchors may be any of those discussed above with reference to the method of the invention. The microparticle is preferably part of the kit for extracting and/or purifying the polynucleotide.

The kit preferably further comprises a leader sequence which is capable of preferentially threading into a transmembrane pore. The kit may comprise a Y adaptor. The kit preferably further comprises a molecular brake, such as a polynucleotide binding protein. Preferred leader sequences. Y adaptors, molecular brakes and polynucleotide binding proteins are discussed above.

Any of the embodiments discussed above with reference to the method of the invention equally apply to the kits. The kit may further comprise the components of a membrane, such as the components of an amphiphilic layer or a triblock copolymer membrane. The kit may further comprise a transmembrane protein pore.

The kit of the invention may additionally comprise one or more other reagents or instruments which enable any of the embodiments mentioned above to be carried out. The kit may comprise a magnet or an electromagnet. Such reagents or instruments include one or more of the following: suitable buffer(s) (aqueous solutions), means to obtain a sample from a subject (such as a vessel or an instrument comprising a needle), means to amplify and/or express polynucleotides, a membrane as defined above or voltage or patch clamp apparatus Reagents may be present in the kit in a dry state such that a fluid sample resuspends the reagents. The kit may also, optionally, comprise instructions to enable the kit to be used in the method of the invention or details regarding for which organism the method may be used.

Apparatus

The invention also provides an apparatus for characterising a target polynucleotide. The apparatus comprises a plurality of membranes and a plurality of pores. The plurality of pores is present in the plurality of membranes. The number of pores and membranes is preferably equal. Preferably, a single pore is present in each membrane.

The apparatus also comprises conditions on the other side of the pores from which the pores are contacted with the polynucleotide which are capable of controlling the formation of secondary structure by the target polynucleotide. Any of the conditions discussed above may be present in the apparatus.

The apparatus preferably comprises a plurality of molecular brakes on the side of the pores which is contacted with the polynucleotide and which are capable of controlling the movement of the target polynucleotide through the pores. Suitable molecular brakes are discussed above.

The apparatus preferably further comprises instructions for carrying out the method of the invention. The apparatus may be any conventional apparatus for analyte analysis, such as an array or a chip. Any of the embodiments discussed above with reference to the methods of the invention are equally applicable to the apparatus of the invention. The apparatus may further comprise any of the features present in the kit of the invention.

The apparatus is preferably set up to carry out the method of the invention.

The apparatus preferably comprises:
a sensor device that is capable of supporting the plurality of pores and membranes and being operable to perform analyte characterisation using the pores and membranes, and at least one port for delivery of the material for performing the characterisation.

Alternatively, the apparatus preferably comprises:
a sensor device that is capable of supporting the plurality of pores and membranes being operable to perform analyte characterisation using the pores and membranes; and
at least one reservoir for holding material for performing the characterisation.

The apparatus more preferably comprises:
a sensor device that is capable of supporting the membrane and plurality of pores and membranes and being operable to perform analyte characterising using the pores and membranes;
at least one reservoir for holding material for performing the characterising;
a fluidics system configured to controllably supply material from the at least one reservoir to the sensor device; and
one or more containers for receiving respective samples, the fluidics system being configured to supply the samples selectively from one or more containers to the sensor device. The apparatus may be any of those described in International Application No. PCT/GB08/004127 (published as WO 2009/077734), PCT/GB10/000789 (published as WO 2010/122293), International Application No. PCT/GB10/002206 (published as WO 2011/067559) or International Application No. PCT/US99/25679 (published as WO 00/28312).

A system is also provided which comprises: (a) a transmembrane pore in a membrane, wherein the membrane defines a first side and a second side, wherein the second side provides a condition that controls formation of a secondary structure from a portion of the target polynucleotide that moves through the transmembrane pore to the second side. The condition that controls formation of a secondary structure from a portion of the target polynucleotide may be any of the conditions described herein for that purpose.

The following Examples illustrate the invention.

EXAMPLES

Example 1

This example illustrates how the formation of secondary structure by the target polynucleotide was controlled by the addition of a number of different polynucleotide sequences to the opposite side of the pore (trans side) to which the target polynucleotide was contacted (cis side).

Materials and Methods

The experimental setup initially consisted of buffer 1 (600 mM KCl, 25 mM K Phosphate buffer. 75 mM Potassium Ferrocyanide (II), 25 mM Potassium Ferricyanide (III), pH 8.0) in the cis and trans sides. The trans side also contained additional additives depending on the experiment e.g. DNA (which may have had a biotin and/or cholesterol modification present) alone or DNA and streptavidin (see table in FIG. 6 for details and description of the DNA sequences for the sequences of the DNA polynucleotides added to the trans side of the nanopore).

Electrical measurements were acquired from single MspA nanopores inserted in block co-polymer in buffer 1. After achieving a single pore inserted in the block co-polymer, then 1 mL of buffer 1 was flowed through the system to remove any excess MspA nanopores. 300 µL of buffer 1 with 0.1 nM construct 1 (see description of DNA sequences and FIG. 1 for the sequence of construct 1), 10 mM MgCl2, 1 mM ATP was then flowed into the single nanopore experimental system. The experiment was run at −120 mV and helicase-controlled DNA movement was monitored.

Description of the DNA Sequences
DNA sequence 1 is shown in SEQ ID NO: 28.
DNA Sequence 2 is shown in SEQ ID NO: 29.
DNA sequence 3 is:

```
                                   (SEQ ID NO: 32)
GCAATATCAGCACCAACAGAAACAACCT/iSp18//iSp18//iSp18//
iSp18//iSp18//iSp18/TT/3CholTEG/
```

DNA sequence 4 is:

```
                                   (SEQ ID NO: 33)
CGTTCTGTTTATGTTTCTTGTTTGTTAGCCTTTTTTTTTTTTTTTTT/
iSpC3//iSpC3//iSpC3//iSpC3/
TTTTTGGCTAACAAACAAGAAACATAAACAGAACG
```

AE202 is:

```
                                   (SEQ ID NO: 34)
              /5Chol-TEG/IIIIIIIIII
```

AE186 is:

```
                                   (SEQ ID NO: 35)
CAAATAACAACATTATCATCACTACCCCTAACAAACAACAAACATAAACA
CAACCTCCTTACCCTTCACTACTCACCACCATCTTTTTTTTCCTACCTTT
TTTTTCACCCCAAAC
```

TE60 is:

```
                                   (SEQ ID NO: 36)
CTACTGATCATAATGTTCTTATTTGT/iSp18//iSp18//iSp18//
iSp18//iSp18//iSp18/TT/3CholTEG/
```

AE203 is:

/5chol-TEG/IIIIIIIIIIIIIIIIIIIII (SEQ ID NO: 38)

AE210 is:

/5BiodT/IIIIIIIIIIIIIIIIIIIIIIIIIIIIIII/3CholTEG/ (SEQ ID NO: 39)

AE191 is:

/5BiodT/IIIIIIIIII (SEQ ID NO: 40)

AE192 is:

/5BiodT/IIIIIIIIIIIIIIIIIIII (SEQ ID NO: 41)

AE193 is:

/5BiodT/IIIIIIIIIIIIIIIIIIIIIIIIIIIIII (SEQ ID NO: 42)

AE263 is shown in SEQ ID NO: 43.
AE264 is shown in SEQ ID NO: 44.
AE265 is shown in SEQ ID NO: 45.
AE266 is shown in SEQ ID NO: 46.
AE267 is shown in SEQ ID NO: 47.
AE268 is shown in SEQ ID NO: 48.
AE269 is shown in SEQ ID NO: 49.
AE270 is shown in SEQ ID NO: 50.
AE271 is shown in SEQ ID NO: 51.
AE272 is shown in SEQ ID NO: 52.
AE273 is shown in SEQ ID NO: 53.
AE274 is shown in SEQ ID NO: 54.
AE275 is shown in SEQ ID NO: 55.
AE276 is shown in SEQ ID NO: 56.
AE277 is shown in SEQ ID NO: 57.
AE278 is shown in SEQ ID NO: 58.
AE279 is shown in SEQ ID NO: 59.
AE280 is shown in SEQ ID NO: 60.
AE281 is shown in SEQ ID NO: 61.
AE282 is shown in SEQ ID NO: 62.
AE283 is shown in SEQ ID NO: 63.
AE284 is shown in SEQ ID NO: 64.
AE285 is shown in SEQ ID NO: 65.
AE286 is shown in SEQ ID NO: 66.
AE287 is shown in SEQ ID NO: 67.
AE288 is shown in SEQ ID NO: 68.
AE289 is shown in SEQ ID NO: 69.
AE290 is shown in SEQ ID NO: 70.
AE291 is shown in SEQ ID NO: 71.
AE292 is shown in SEQ ID NO: 72.
AE258 is shown in SEQ ID NO: 73.
AE259 is shown in SEQ ID NO: 74.
AE182 is shown in SEQ ID NO: 75.

Analysis

Figure 2:
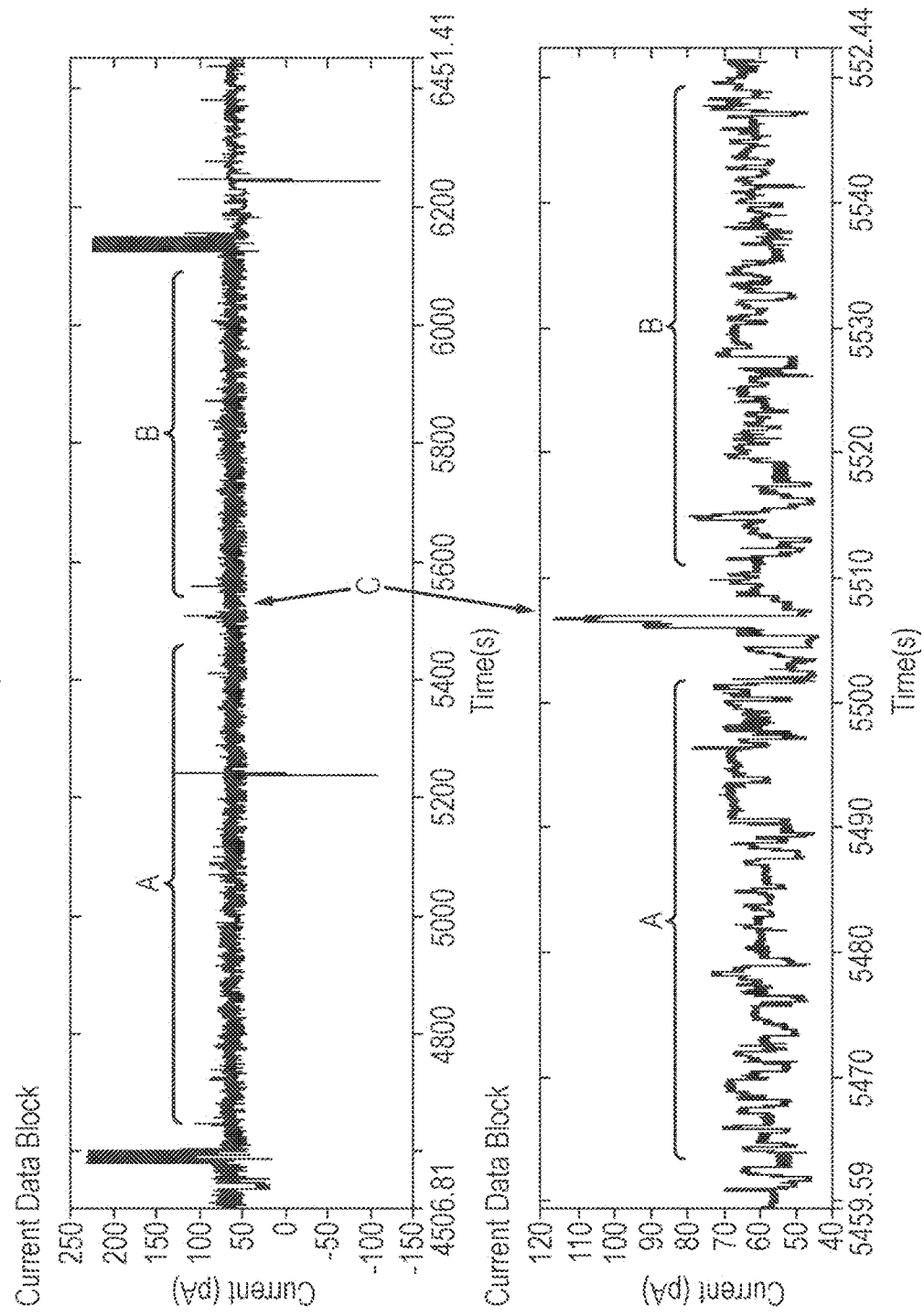
FIG. 2 shows an example current trace (y-axis label=Current (pA), x-axis label=Time(s)) of when a helicase (T4 Dda 1993-(E94C/A360C)) controlled the translocation of the DNA construct 1 through an MspA nanopore. The lower picture is a zoomed in version of the upper one. The region labelled A corresponds to the template (DNA sequence 1). The region labelled B corresponds to the complement (DNA sequence 2). The region labelled C corresponds to the hairpin (DNA sequence 4). In this figure, the template and complement have similar current range, are of similar duration and have similar speed. This is an example of a helicase controlled DNA movement exhibiting No Uplift.
Figure 4:
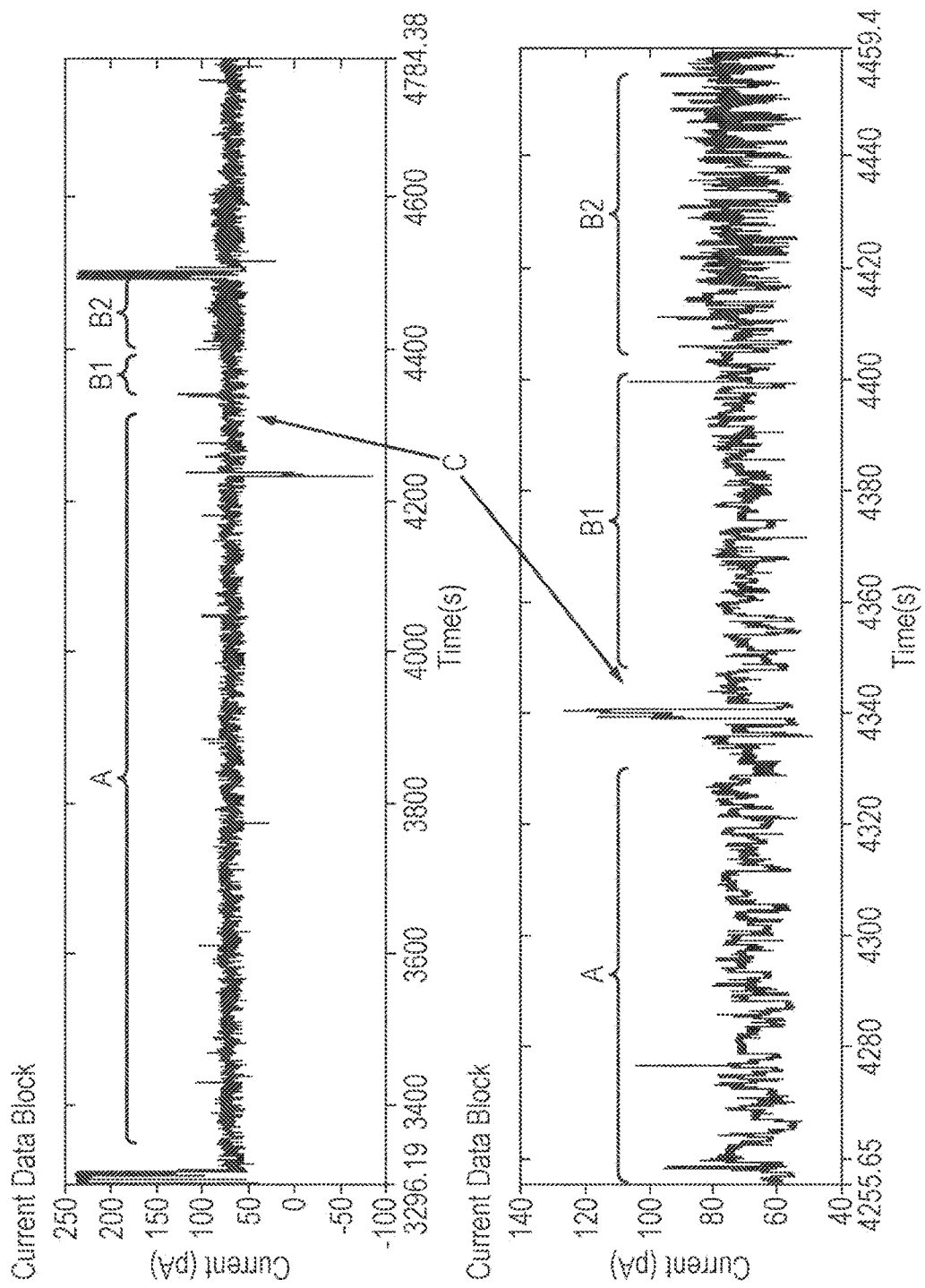
FIG. 4 shows an example current trace (y-axis label=Current (pA), x-axis label=Time(s)) of when a helicase (T4 Dda 1993-(E94C/A360C)) controlled the translocation of the DNA construct 1 through an MspA nanopore. The lower picture is a zoomed in version of the upper one. The region labelled A corresponds to the template (DNA sequence 1). The regions labelled B1 and B2 correspond to the complement (DNA sequence 2). The region labelled C corresponds to the hairpin (DNA sequence 4). In this figure, the complement initially has a similar current range and speed to the template (B1) and then changes to a behaviour where the current range is higher than the template, the speed is faster and the duration is shorter. This is an example of helicase controlled DNA movement exhibiting Delayed Uplift.

For the experiments in which there was DNA in the trans, the signals produced by construct 1 translocating through the pore in which the hairpin was clearly identified were observed and categorized as either having uplift, no uplift or delayed uplift (FIGS. 2-4) this was done with several different trans DNA sequences and concentrations. This data was compiled into a table showing what was in the trans and number of helicase controlled polynucleotide movements in each category (see FIG. 6). This data was also plotted as a bar chart (see FIG. 7).

In addition, experiments were also carried out with DNA sequence AE182 in the trans at a concentration of 500 nM in buffer 1. For these experiments the signals were observed to see if they had the expected non-uplifted section in a background of uplifted complement (FIG. 5).

Results

Figure 7:
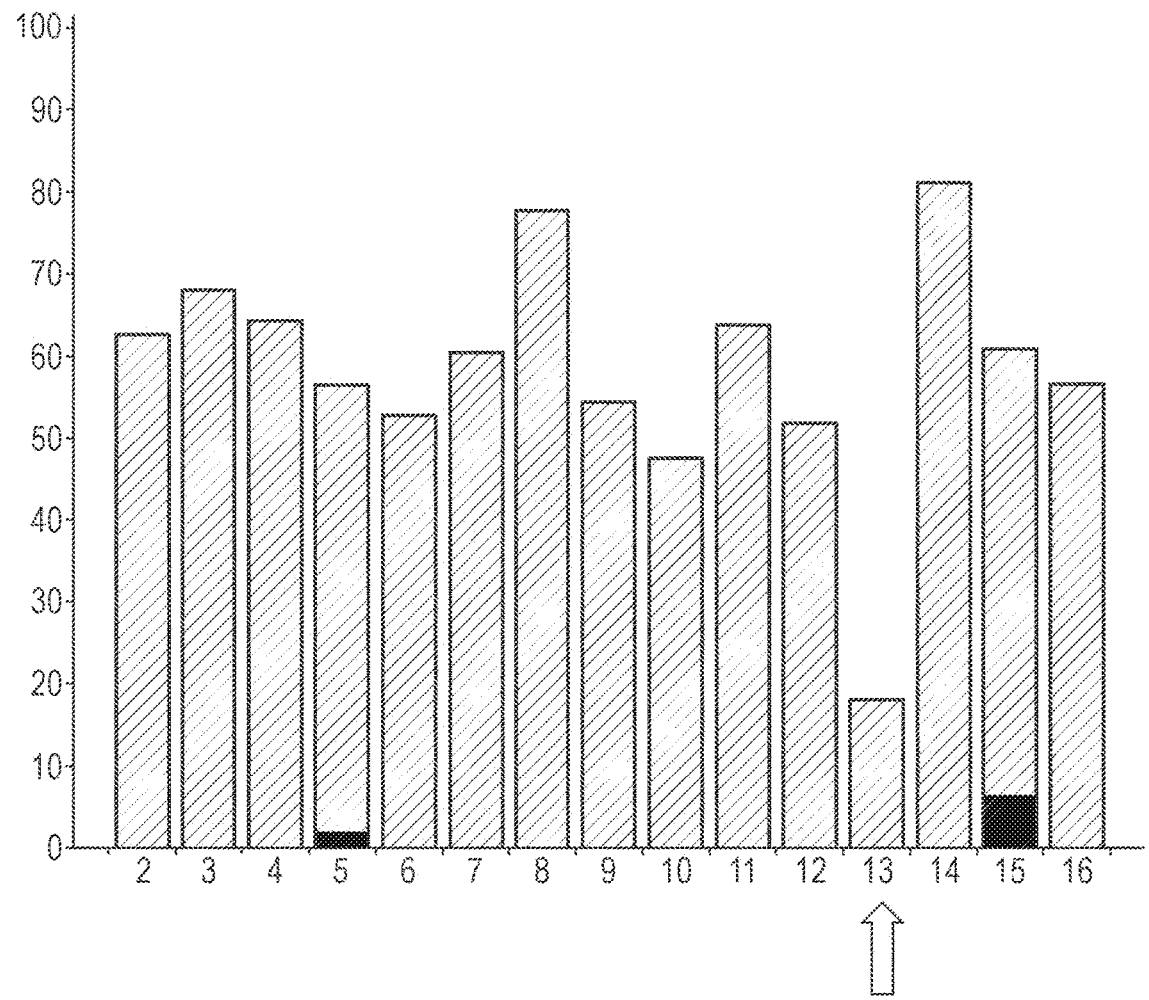
FIG. 7 shows the data in FIG. 6 as a bar chart. The numbers on the x axis correspond to the row numbers of the data table (FIG. 6). The numbers on the y axis correspond to the % of observed helicase controlled movements. The height of the black bar represents the % of translocations that have been categorised as "no uplift" as opposed to "uplift" or "delayed uplift". The control conditions (no polynucleotide sequences added to the trans side to control secondary structure) is shown in row number 13 and is marked with an arrow.

The data shown in FIGS. 6 and 7 illustrates that the addition of a variety of different polynucleotide sequences (see Col 1 of FIG. 6) which hybridise to construct 1 successfully reduced the number of helicase controlled DNA movements which exhibited uplift in the complement region of construct 1. The control condition (no addition of any polynucleotide sequences shown in row 13 of FIGS. 6 and 7) exhibited approximately 80% uplift in the helicase controlled DNA movements. Whereas conditions 2-12 and 14-16 all exhibited a decrease in the % of uplift observed in the helicase controlled DNA movements. Therefore, the addition of the polynucleotide sequences to the trans side (the opposite side of the pore to which the target polynucleotide was contacted) reduced the formation of secondary structure by the target polynucleotide sequence on the trans side of the nanopore.

Example 2

This example illustrates how the formation of secondary structure by the target polynucleotide was controlled by the addition of an exonuclease (SAN) to the opposite side of the pore (trans side) to which the target polynucleotide was contacted (cis side).

Materials and Methods

The experimental setup initially consisted of buffer 1 (600 mM KCl, 25 mM K Phosphate buffer, 75 mM Potassium Ferrocyanide (II), 25 mM Potassium Ferricyanide (III), pH 8.0) in the cis and trans. The trans side also contains 10 mM MgCl2 and 0.005 U/uL and 0.1 U/uL Salt Activated Nuclease (SAN) from Arcticzymes.

Electrical measurements were acquired from single MspA nanopores inserted in block co-polymer in buffer 1. After achieving a single pore inserted in the block co-polymer, then 1 mL of buffer 1 was flowed through the system to remove any excess MspA nanopores. 300 μL of buffer 1 with 0.1 nM construct 1 (see description of DNA sequences and FIG. 1 for the sequence of construct 1), 10 mM MgCl2, 1 mM ATP was then flowed into the single nanopore experimental system. The experiment was run at −120 mV and helicase-controlled DNA movement monitored.

Analysis

Analysis was carried out for this experiment in the same way as for Example 1 described previously.

Results

Figure 8:
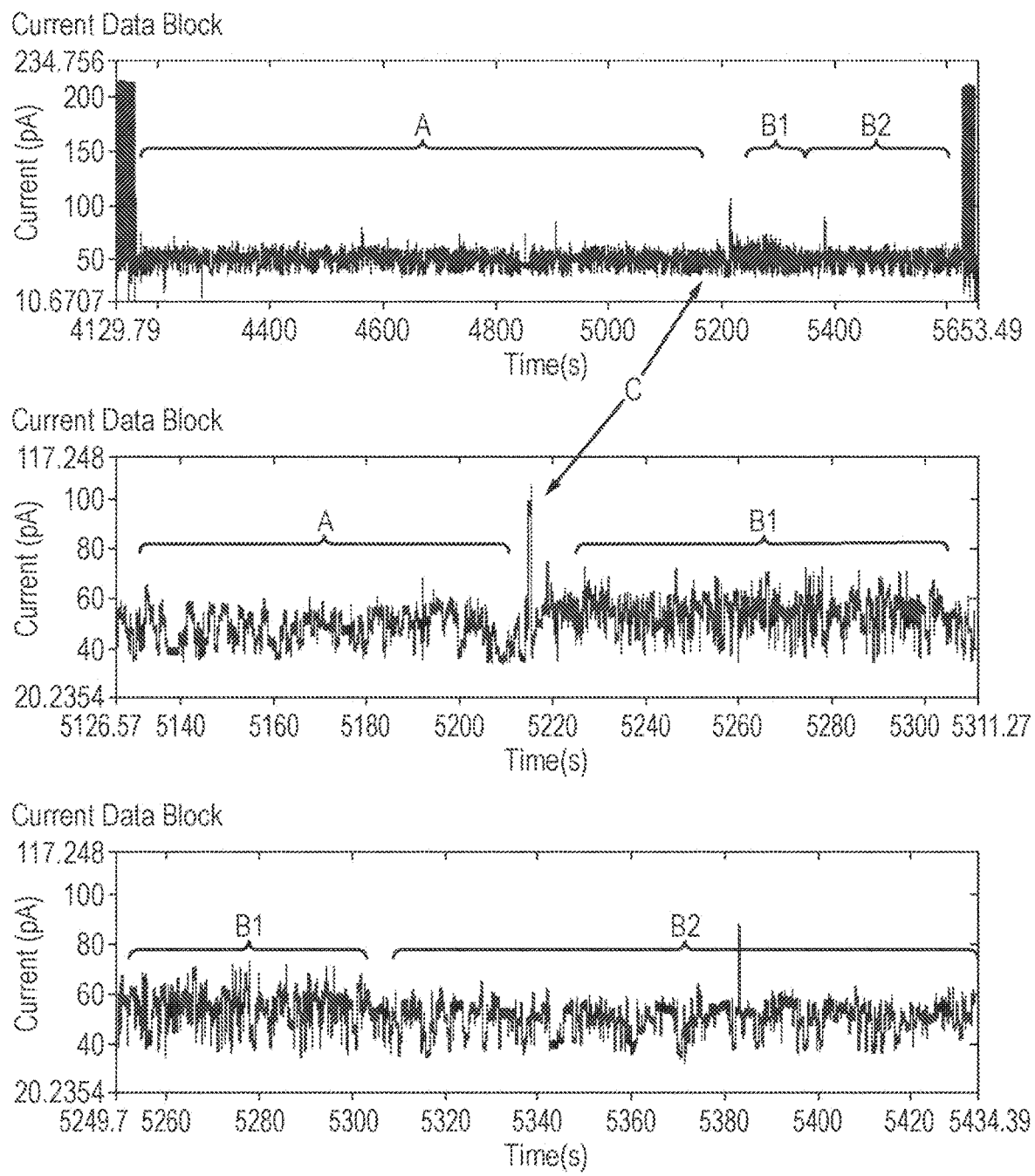
FIG. 8 shows an example current trace (y-axis label=Current (pA). x-axis label=Time(s)) of when a helicase (T4 Dda 1993-(E94C/A360C)) controlled the translocation of the DNA construct 1 through an MspA nanopore. The lower pictures are zoomed in versions of the top one. The region labelled A corresponds to the template (DNA sequence 1). The regions labelled B1 and B2 correspond to the complement (DNA sequence 2). The region labelled C corresponds to the hairpin (DNA sequence 4). In this figure, the complement initially has a higher current range and speed to the template (B1) and then changes to a behaviour where the current range and speed are similar to the template. This example trace shows that the salt active nuclease (SAN) cut construct 1 part way along the template region. Thus uplift was observed in the region labelled B1 but not in the region labelled B2 because the region of the template which hybridised to the complement had been cut off by the SAN when region B2 translocated through the nanopore.
Figure 9:
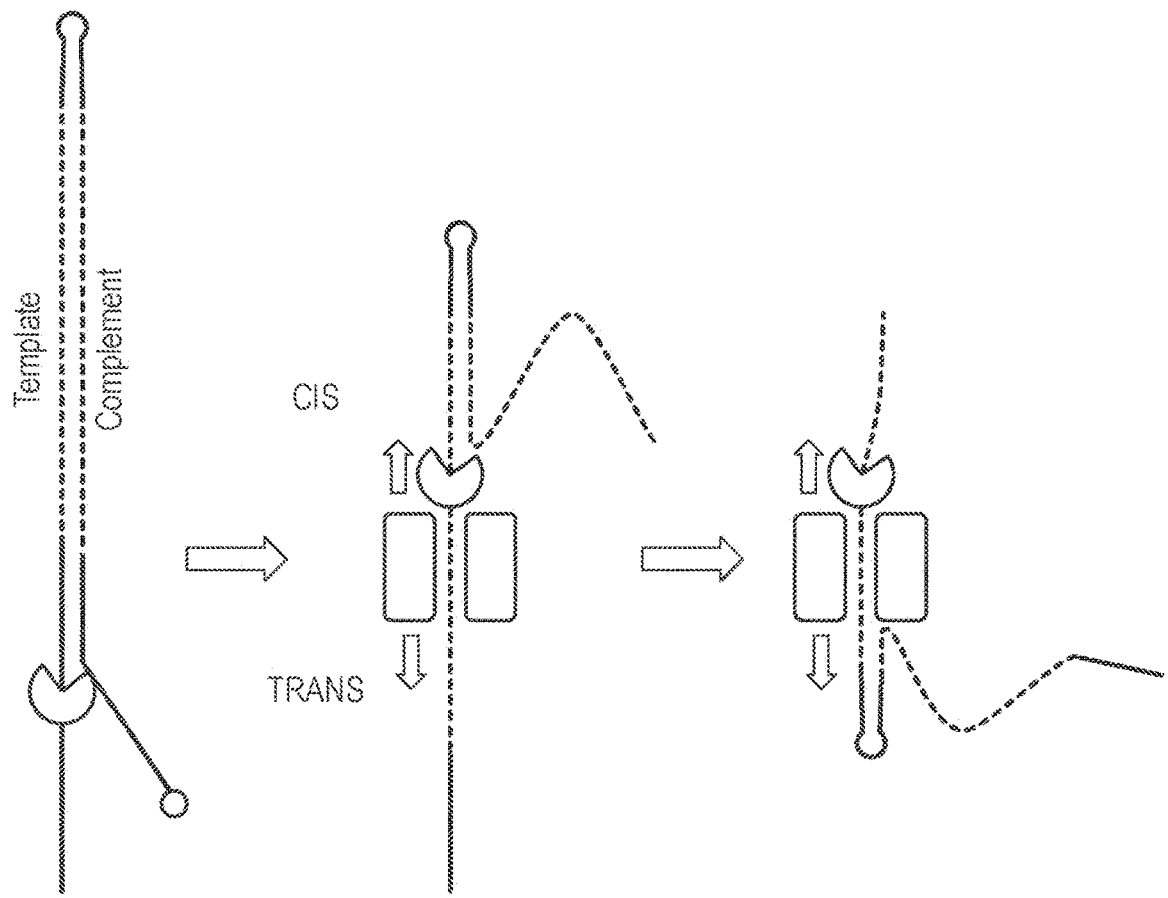
FIG. 9 shows a double stranded polynucleotide with a template region, a complement region and a prebound enzyme. The helicase controls the movement of the polynucleotide through the nanopore. Once the hairpin (which connects the template and complement regions) translocates through the nanopore then DNA begins to re-hybridise on the trans side of the nanopore. It is the rehybridisation which is thought to result in uplift being observed in the complement region under helicase controlled DNA movement.
Figure 10:
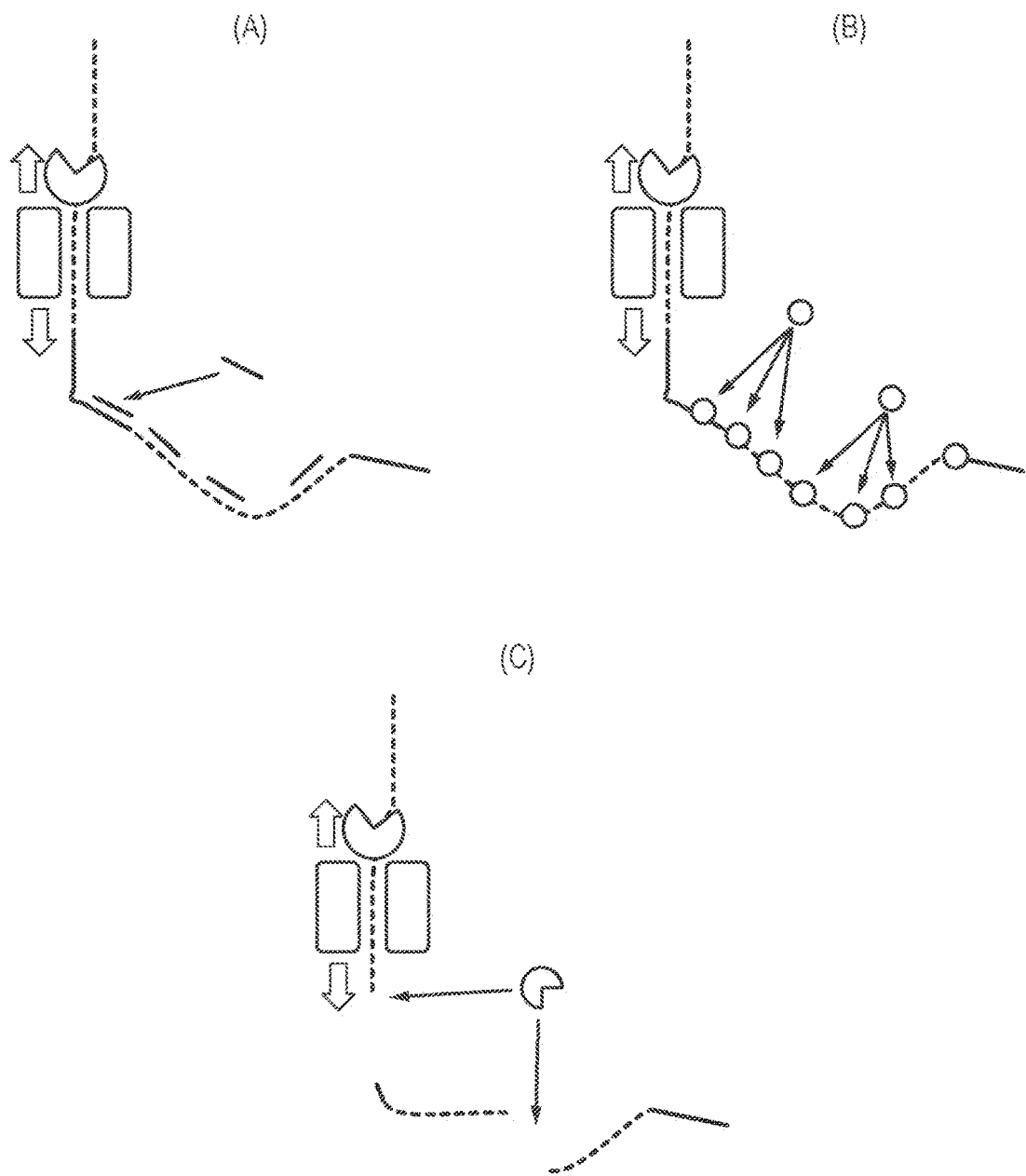
FIG. 10 shows a number of methods which can be used to control the formation of secondary structure on the trans side of the nanopore. A) shows the hybridisation of polynucleotides to the target polynucleotide on the trans side which prevents it reforming into a double-stranded construct with the complement region as it translocates through the nanopore. B) shows the use of protein or chemical traps which bind to the target polynucleotide on the trans side and prevents it reforming into a double-stranded construct with the complement region as it translocates through the nanopore. C) shows the use of a nuclease enzyme to cut the target polynucleotide on the trans side and prevents it reforming into a double-stranded construct with the complement region as it translocates through the nanopore.

For experiments for which there was SAN in trans, the helicase controlled DNA movements were observed to see if there was any uplift. 50-60% of the helicase controlled DNA movements were observed to have no uplift which is higher than the 20% no uplift observed for the control detailed in example 1. Helicase controlled DNA movements of the type shown in FIGS. 2 (non-uplifted), FIG. 3 (uplifted) and a new type of behaviour such as that shown in FIG. 8 (initial uplift in the complement strand region and then becoming non-uplifted-which indicates cleavage by SAN) were observed in this experiment. Therefore, the addition of SAN to the trans side (the opposite side of the pore to which the target polynucleotide was contacted) reduced the formation of secondary structure by the target polynucleotide sequence on the trans side of the nanopore.

Example 3

This example illustrates how the hairpin loop is designed to control the ability of the two strands of the target polynucleotide to rehybridise on the other side of the pore. G-Quadruplex (G4) are ribonucleic acid secondary structures. Incorporating them in to hairpins offers one way of attenuating uplift behaviour by providing the DNA with an alternative to rehybridisation.

A useful property of G4 is their tendency to form stable structures in certain ionic environments, meaning the hairpin structures may be formed in line with existing methods. The G4 structure is "activated" once the hairpin has been broken (i.e., stripped by the nanopore revealing the G4 sequence) and in the presence of a high concentration of suitable ions.

DNA Sequences

```
TH14    /5Phos/CGT GGTTGGTGTGGTTGG CG
        GACACTGATTGACACGGTTTAGTAGAGC/iSp18//iSp18//iSp18//iSp18/TTTTTTTTTTTT
        TTTTTTTTTTCGCCAACCACACCAACCACGTCCT (SEQ ID NO: 76)

TH15    /5Phos/CGT CCAACCACACCAACC CG
        GACACTGATTGACACGGTTTAGTAGAGC/iSp18//iSp18//iSp18//iSp18/TTTTTTTTTTTT
        TTTTTTTTTTCGGGTTGGTGTGGTTGG ACGTCCT (SEQ ID NO: 77)

TH16    /5Phos/CGT AGTCCGTGGTAGGGCAGGTTGGGGTGACCGGACACTGATTGACACGG
        TTTAGTAGAGC/iSp18//iSp18//iSp18//iSp18/TTTTTTTTTTTTTTTTTTTTTTTCGAGTCAC
        CCCAACCTGCCCTACCACGGACTACGTCCT (SEQ ID NO: 78)

TH17    /5Phos/CGTAGTCACCCCAACCTGCCCTACCACGGACTCGGACACTGATTGACACGGT
        TTAGTAGAGC/iSp18//iSp18//iSp18//iSp18/TTTTTTTTTTTTTTTTTTTTTTTCGAGTCCGT
        GGTAGGGCAGGTTGGGGTGACT ACGTCCT (SEQ ID NO: 79)
```

TH14 and 15 contain TBA sequence highlighted.

TH16 and 17 contain a TBA derivative called HD22 highlighted. This contains a psudeo G4 with additional duplex structure.

```
Control hairpin sequence =
                                        (SEQ ID NO: 80)
/5Phos/CGTCCTGTCGCTGTGTCTCGGACACTGATTGACACGGTTTAGT
AGAGC/iSpC3//iSpC3//iSpC3//iSpC3/TTTTTTTTTTTTTTTT
TTTTTTTTTTCGAGACACAGCGACAGGACGTCCT
```

Y adapter sequence 1

```
                                        (SEQ ID NO: 81)
5SpC3//iSpC3//iSpC3//iSpC3//iSpC3//iSpC3//iSpC3// iSpC3//iSpC3//iSpC3//iSpC3//iSpC3//iSpC3//iSpC3// iSpC3//iSpC3//iSpC3//iSpC3//iSpC3//iSpC3//iSpC3// iSpC3//iSpC3//iSpC3//iSpC3//iSpC3//iSpC3//iSpC3// iSpC3//iSpC3/GGCGTCTGCTTGGGTGTTTAACCTTTTTTTTTTT/ iSp18//iSp18//iSp18//iSp18/GGTTGTTTCTGTTGGTGCTGATA

TTGCT
```

Y Adapter Sequence 2

```
                                        (SEQ ID NO: 82)
5Phos/GCAATATCAGCACCAACAGAAA/iBNA-MeC//iBNA-A//
iBNA-A//iBNA-MeC//iBNA-MeC/TTTGAGGCGAGCGGTCAA
```

Y Adapter Sequence 3

```
                                        (SEQ ID NO: 83)
/5BNA-G//iBNA-G//iBNA-T//iBNA-T//iBNA-A/
AACACCCAAGCAGACGCCTT
```

Method

Oligos were stocked at 100 uM in TE pH 8.0. The oligos were then diluted to 500 nM in 10 mM Tris, 2 mM EDTA, 50 mM NaCl and heated at 95° C. for 15 min. The diluted oligos were then transferred to an ice bath for 15 min.

Figure 11:
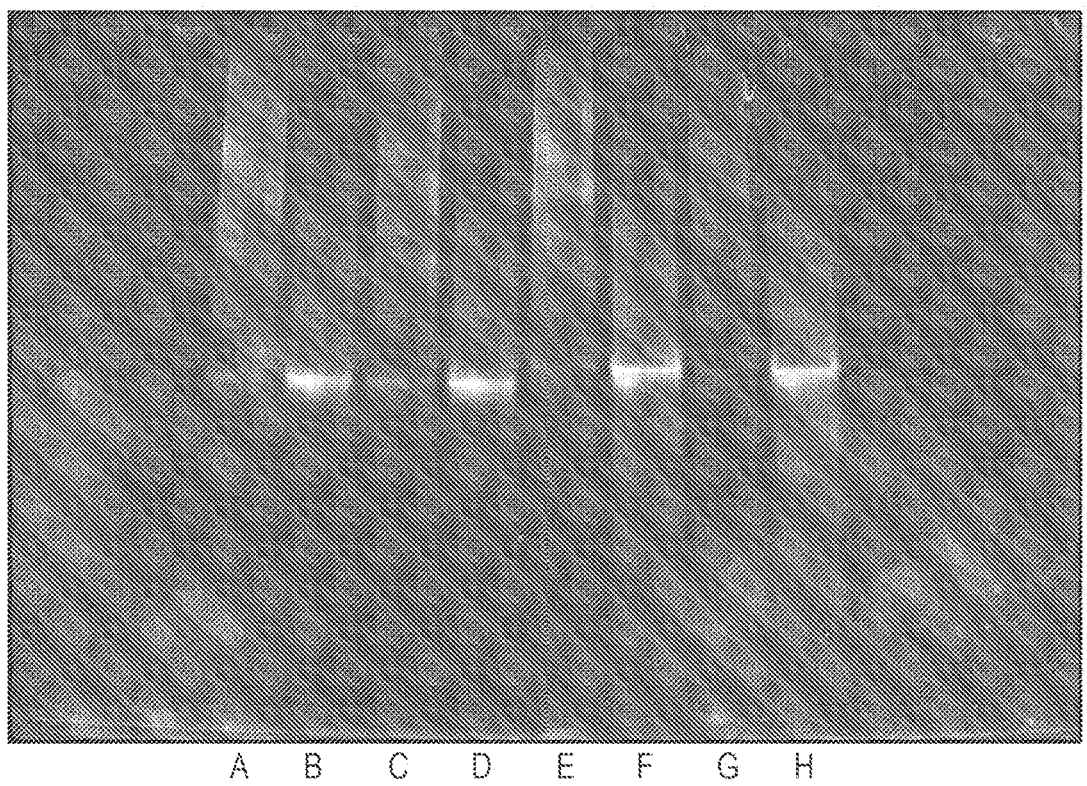
FIG. 11 shows a 4-20% TBE gel showing the quardruplex containing oligos. Col A=oligo TH14 (stock). Col B=TH14 (snapcooled). Col C=TH15 (stock). Col D=THIS (snapcooled). Col E=TH16 (stock). Col F=TH16 (snapcooled). Col G=TH17 (stock). Col H=TH17 (snapcooled). A single band in the gel shown in FIG. 11 suggests the oligonucleotide is a single species.

1 ng of stock was run against 1 ng of snapcooled DNA on a 4-20% TBE gel (2 ul DNA+4 ul native sample buffer, 4-20% TBE gel (see FIG. 11), TBE running buffer. 100 mV 1 hr, 160 mV 30 min. TBE/Sybr Gold 5 min, $H_2O$ 5min). A single band in the gel shown in FIG. 11 suggests the oligonucleotide is a single species.

The Y-adapter sequences were annealed. The Y-adapter and the appropriate hairpin adapter (TH14, 15, 16 or 17) were then ligated to dsDNA. A helicase to control the DNA movement was also loaded onto the DNA. This was known as DNA construct produced by ligation.

Electrical measurements were acquired from single MspA nanopores inserted in block co-polymer in buffer (25 mM K Phosphate buffer, 150 mM Potassium Ferrocyanide (II), 150 mM Potassium Ferricyanide (III), pH 8.0). After achieving a single pore inserted in the block co-polymer, then buffer (2 mL, 25 mM K Phosphate buffer, 150 mM Potassium Ferrocyanide (II), 150 mM Potassium Ferricyanide (III), pH 8.0) was flowed through the system to remove any excess MspA nanopores. 150 µL of 500 mM KCl, 25 mM K Phosphate, pH8.0 was then flowed through the system. After 10 minutes a further 150 µL of 500 mM KCl, 25 mM K Phosphate, pH8.0 was flowed through the system and then the enzyme (see list below, 10 nM final concentration), DNA construct produced by ligation (see previous method) (0.1 nM final concentration), fuel (MgCl2 2 mM final concentration, ATP 2 mM final concentration) pre-mix (150 µL total) was then flowed into the single nanopore experimental system. The experiment was run at −140 mV and helicase-controlled DNA movement monitored.

Results

The DNA will face range of other ionic environments before it meets the trans-side of a nanopore (ligation buffer, wash buffers, running buffers etc.). The structure remained as a hairpin at least until ligation had occurred. PAGE analysis suggests the hairpin confirmation is stable and preferred. The hairpin structure was preferred to G4 until denatured by the nanopore.

Figure 12:
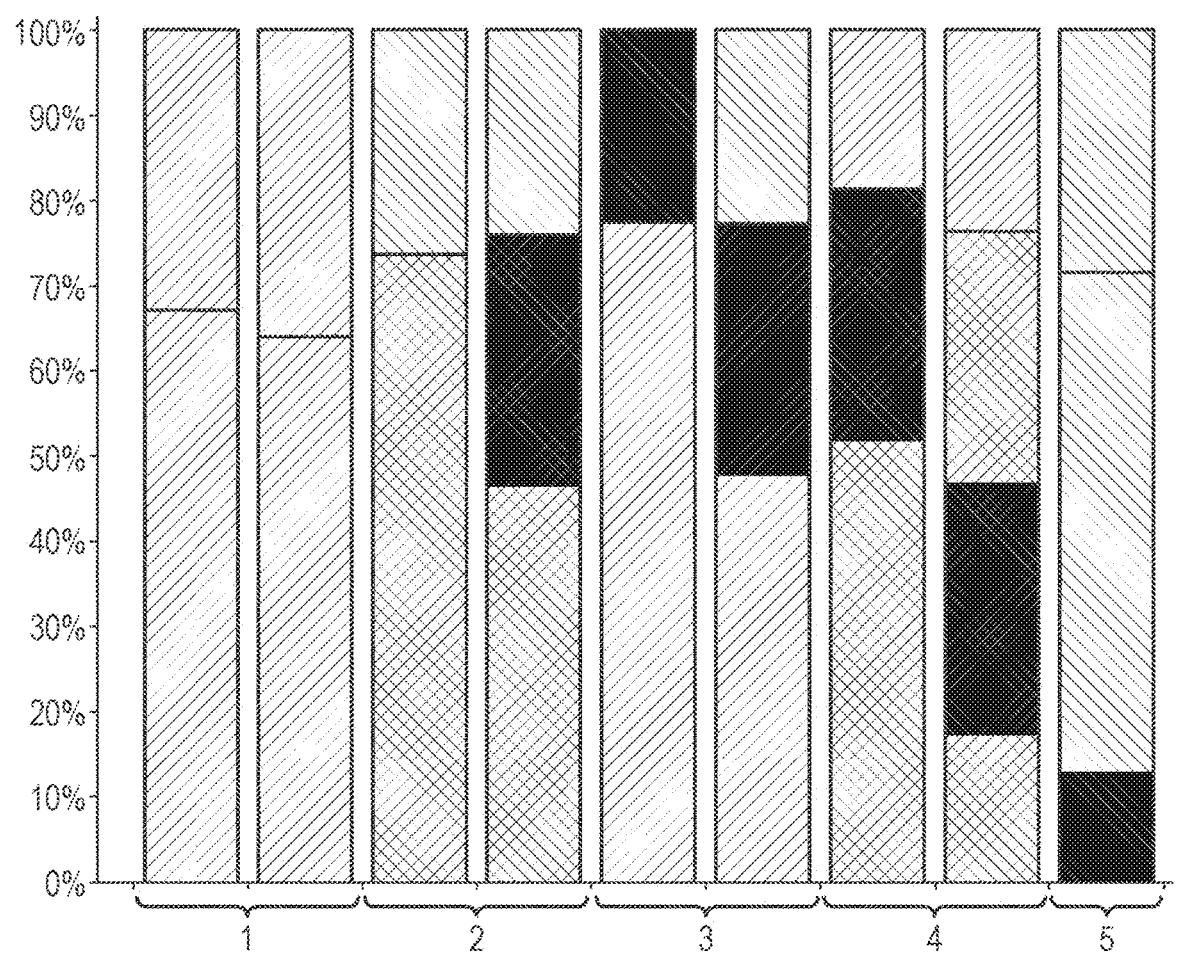
FIG. 12 shows a bar chart. The numbers on the x axis correspond the oligo's which have quadruplexes present in their hairpins and were ligated to dsDNA-1=control, 2=TH14, 3=TH15, 4=TH16 and 5=TH17. The numbers on the y axis correspond to the % of observed helicase controlled movements. The height of the lower region of the bar represents the % of translocations that have been categorised as no uplift and the height of the upper region of the bar represents the % of translocations that have been categorized as uplift. i.e. the shorter the upper region of the bar, the lower the uplift. The results for control conditions (no polynucleotide sequences added to the trans side to control secondary structure) are shown in row number 1.

As shown in FIG. 12, all G4 designs (TH14-TH17) showed an improved proportion of non-uplifted to uplifted. Therefore, the use of hairpins containing G4 controlled the ability of the two strands of the target polynucleotide to rehybridise on the other side of the pore.

---

The invention claimed is:

1. A method of characterising a target polynucleotide, comprising:
   (a) providing a transmembrane pore in a membrane having a cis side and a trans side and carrying out steps (b)-(d) under one applied potential;
   (b) contacting, on the cis side of the membrane, the target polynucleotide with the transmembrane pore and a molecular brake which controls the movement of a strand of the target polynucleotide through the transmembrane pore;
   (c) taking one or more measurements as the molecular brake controls the movement of the strand through the transmembrane pore, wherein the one or more measurements are indicative of one or more characteristics of the target polynucleotide as the target polynucleotide moves through the transmembrane pore; and
   (d) decreasing formation of secondary structure by the target polynucleotide by using an endonuclease on the trans side of the membrane to cleave a portion of the strand of the target polynucleotide that has translocated to the trans side of the membrane as the molecular brake controls movement of the strand of the target polynucleotide through the transmembrane pore.

2. The method according to claim 1, wherein the endonuclease decreases formation of random secondary structure by the target polynucleotide on the trans side of the membrane, wherein the random secondary structure comprises (a) one or more helices, (b) one or more loops, (c) one or more pseudoknots, (d) one or more quadruplexes, or (e) a combination thereof.

3. The method according to claim 1, wherein the molecular brake is a polynucleotide binding protein.

4. The method according to claim 1, wherein the transmembrane pore is (i) a protein pore or (ii) a solid state pore.

5. The method according to claim 1, wherein the entire target polynucleotide moves through the transmembrane pore and is characterised.

6. The method according to claim 1, wherein characterising the target polynucleotide comprises estimating the sequence of the target polynucleotide or sequencing the target polynucleotide.

7. The method according to claim 1, wherein the molecular brake is a polymerase, helicase or exonuclease.

8. The method according to claim 1, wherein the transmembrane pore is a protein pore or based on Msp, α-hemolysin (α-HL), lysenin, CsgG, ClyA, Sp1 or FraC.

9. The method according to claim 1, wherein the target polynucleotide is single-stranded.

10. The method according to claim 1, wherein the molecular brake is a helicase.

11. A method characterising a target polynucleotide, wherein the target polynucleotide is double stranded and the method comprises:
   (a) providing a construct comprising the target polynucleotide in which the two strands of the target polynucleotide are linked at one end of the target polynucleotide by a hairpin loop;
   (b) providing a transmembrane pore in a membrane having a cis side and a trans side and carrying out steps (c)-(e) under one applied potential;
   (c) contacting, on the cis side of the membrane, the construct with the transmembrane pore and a molecular brake which separates the two strands of the construct and controls the movement of the construct through the transmembrane pore one strand at a time;
   (d) taking one or more measurements as the molecular brake controls the movement of the strand through the transmembrane pore, wherein the one or more measurements are indicative of one or more characteristics of the target polynucleotide as the construct moves through the transmembrane pore; and
   (e) decreasing formation of secondary structure by the target polynucleotide by using an endonuclease on the trans side of the membrane to cleave a portion of each strand of the target polynucleotide that has translocated to the trans side of the membrane as the molecular brake controls movement of the construct through the transmembrane pore one strand at a time.

12. The method according to claim 11, wherein the endonuclease decreases rehybridization of the two strands of the target polynucleotide on the trans side of the membrane or prevent the two strands of the target polynucleotide from rehybridising on the trans side of the membrane.

13. The method according to claim 11, wherein the molecular brake is a polynucleotide binding protein.

14. The method according to claim 11, wherein the transmembrane pore is (i) a protein pore or (ii) a solid state pore.

15. The method according to claim 11, wherein the entire target polynucleotide moves through the transmembrane pore and is characterised.

16. The method according to claim 11, wherein characterising the target polynucleotide comprises estimating the sequence of the target polynucleotide or sequencing the target polynucleotide.

17. The method according to claim 11, wherein the molecular brake is a polymerase, helicase or exonuclease.

18. The method according to claim 11, wherein the transmembrane pore is a protein pore or based on Msp, α-hemolysin (α-HL), lysenin, CsgG, ClyA, Sp1 or FraC.

19. The method according to claim 11, wherein the molecular brake is a helicase.

* * * * *

SEQUENCE LISTING

<160> NUMBER OF SEQ ID NOS: 83

<210> SEQ ID NO 1
<211> LENGTH: 558
<212> TYPE: DNA
<213> ORGANISM: Artificial Sequence
<220> FEATURE:
<223> OTHER INFORMATION: MS-B1

<400> SEQUENCE: 1

```
atgggtctgg ataatgaact gagcctggtg gacggtcaag atcgtaccct gacggtgcaa      60
caatgggata cctttctgaa tggcgttttt ccgctggatc gtaatcgcct gacccgtgaa     120
tggtttcatt ccggtcgcgc aaaatatatc gtcgcaggcc cgggtgctga cgaattcgaa     180
ggcacgctgg aactgggtta tcagattggc tttccgtggt cactgggcgt tggtatcaac     240
ttctcgtaca ccacgccgaa tattctgatc aacaatggta acattaccgc accgccgttt     300
ggcctgaaca gcgtgattac gccgaacctg tttccgggtg ttagcatctc tgcccgtctg     360
ggcaatggtc cgggcattca agaagtggca acctttagtg tgcgcgtttc cggcgctaaa     420
ggcggtgtcg cggtgtctaa cgcccacggt accgttacgg gcgcggccgg cggtgtcctg     480
ctgcgtccgt tcgcgcgcct gattgcctct accggcgaca gcgttacgac ctatggcgaa     540
ccgtggaata tgaactaa                                                    558
```

<210> SEQ ID NO 2
<211> LENGTH: 184
<212> TYPE: PRT
<213> ORGANISM: Artificial Sequence
<220> FEATURE:
<223> OTHER INFORMATION: MS-B1

<400> SEQUENCE: 2

```
Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asn Asn Gly Asn Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Arg Leu Gly Asn Gly Pro Gly Ile Gln Glu Val
        115                 120                 125

Ala Thr Phe Ser Val Arg Val Ser Gly Ala Lys Gly Val Ala Val
    130                 135                 140

Ser Asn Ala His Gly Thr Val Thr Gly Ala Ala Gly Gly Val Leu Leu
145                 150                 155                 160
```

```
Arg Pro Phe Ala Arg Leu Ile Ala Ser Thr Gly Asp Ser Val Thr Thr
                165                 170                 175

Tyr Gly Glu Pro Trp Asn Met Asn
            180
```

<210> SEQ ID NO 3
<211> LENGTH: 885
<212> TYPE: DNA
<213> ORGANISM: Artificial Sequence
<220> FEATURE:
<223> OTHER INFORMATION: alpha-HL-NN

<400> SEQUENCE: 3

```
atggcagatt ctgatattaa tattaaaacc ggtactacag atattggaag caatactaca      60
gtaaaaacag gtgatttagt cacttatgat aaagaaaatg gcatgcacaa aaaagtattt    120
tatagttta  tcgatgataa aaatcacaat aaaaaactgc tagttattag aacaaaaggt    180
accattgctg gtcaatatag agtttatagc gaagaaggtg ctaacaaaag tggtttagcc    240
tggccttcag cctttaaggt acagttgcaa ctacctgata tgaagtagc  tcaaatatct    300
gattactatc caagaaattc gattgataca aaaaactata tgagtacttt aacttatgga    360
ttcaacggta tgttactgg  tgatgataca ggaaaaattg gcggccttat tggtgcaaat    420
gtttcgattg tcatacact  gaactatgtt caacctgatt tcaaaacaat tttagagagc    480
ccaactgata aaaagtagg  ctggaaagtg atatttaaca atatggtgaa tcaaaattgg    540
ggaccatacg atcgagattc ttggaacccg gtatatggca atcaactttt catgaaaact    600
agaaatggtt ctatgaaagc agcagataac ttccttgatc ctaacaaagc aagttctcta    660
ttatcttcag ggttttcacc agacttcgct acagttatta ctatggatag aaaagcatcc    720
aaacaacaaa caaatataga tgtaatatac gaacagagttc gtgatgatta ccaattgcat    780
tggacttcaa caaattggaa aggtaccaat actaaagata atggacaga  tcgttcttca    840
gaaagatata aaatcgattg ggaaaaagaa gaaatgacaa attaa                   885
```

<210> SEQ ID NO 4
<211> LENGTH: 293
<212> TYPE: PRT
<213> ORGANISM: Artificial Sequence
<220> FEATURE:
<223> OTHER INFORMATION: alpha-HL-NN

<400> SEQUENCE: 4

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Asn Tyr
            100                 105                 110

Met Ser Thr Leu Thr Tyr Gly Phe Asn Gly Asn Val Thr Gly Asp Asp
        115                 120                 125
```

```
Thr Gly Lys Ile Gly Gly Leu Ile Gly Ala Asn Val Ser Ile Gly His
        130                 135                 140

Thr Leu Asn Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Glu Arg Tyr Lys Ile Asp Trp Glu Lys
        275                 280                 285

Glu Glu Met Thr Asn
    290

<210> SEQ ID NO 5
<211> LENGTH: 184
<212> TYPE: PRT
<213> ORGANISM: Artificial Sequence
<220> FEATURE:
<223> OTHER INFORMATION: MspB

<400> SEQUENCE: 5

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
                20                  25                  30

Arg Asn Arg Leu Thr Arg Glu Trp Phe His Ser Gly Arg Ala Lys Tyr
            35                  40                  45

Ile Val Ala Gly Pro Gly Ala Asp Glu Phe Glu Gly Thr Leu Glu Leu
        50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180
```

<210> SEQ ID NO 6
<211> LENGTH: 184
<212> TYPE: PRT
<213> ORGANISM: Artificial Sequence
<220> FEATURE:
<223> OTHER INFORMATION: MspC

<400> SEQUENCE: 6

```
Gly Leu Asp Asn Glu Leu Ser Leu Val Asp Gly Gln Asp Arg Thr Leu
1               5                   10                  15
Thr Val Gln Gln Trp Asp Thr Phe Leu Asn Gly Val Phe Pro Leu Asp
            20                  25                  30
Arg Asn Arg Leu Thr Arg Glu Trp Phe His Ser Gly Arg Ala Lys Tyr
        35                  40                  45
Ile Val Ala Gly Pro Gly Ala Asp Glu Phe Glu Gly Thr Leu Glu Leu
    50                  55                  60
Gly Tyr Gln Ile Gly Phe Pro Trp Ser Leu Gly Val Gly Ile Asn Phe
65                  70                  75                  80
Ser Tyr Thr Thr Pro Asn Ile Leu Ile Asp Asp Gly Asp Ile Thr Gly
                85                  90                  95
Pro Pro Phe Gly Leu Glu Ser Val Ile Thr Pro Asn Leu Phe Pro Gly
            100                 105                 110
Val Ser Ile Ser Ala Asp Leu Gly Asn Gly Pro Gly Ile Gln Glu Val
        115                 120                 125
Ala Thr Phe Ser Val Asp Val Ser Gly Pro Ala Gly Gly Val Ala Val
    130                 135                 140
Ser Asn Ala His Gly Thr Val Thr Gly Ala Ala Gly Gly Val Leu Leu
145                 150                 155                 160
Arg Pro Phe Ala Arg Leu Ile Ala Ser Thr Gly Asp Ser Val Thr Thr
                165                 170                 175
Tyr Gly Glu Pro Trp Asn Met Asn
            180
```

<210> SEQ ID NO 7
<211> LENGTH: 183
<212> TYPE: PRT
<213> ORGANISM: Artificial Sequence
<220> FEATURE:
<223> OTHER INFORMATION: MspD

<400> SEQUENCE: 7

```
Val Asp Asn Gln Leu Ser Val Val Asp Gly Gln Gly Arg Thr Leu Thr
1               5                   10                  15
Val Gln Gln Ala Glu Thr Phe Leu Asn Gly Val Phe Pro Leu Asp Arg
            20                  25                  30
Asn Arg Leu Thr Arg Glu Trp Phe His Ser Gly Arg Ala Thr Tyr His
        35                  40                  45
Val Ala Gly Pro Gly Ala Asp Glu Phe Glu Gly Thr Leu Glu Leu Gly
    50                  55                  60
Tyr Gln Val Gly Phe Pro Trp Ser Leu Gly Val Gly Ile Asn Phe Ser
65                  70                  75                  80
Tyr Thr Thr Pro Asn Ile Leu Ile Asp Gly Gly Asp Ile Thr Gln Pro
                85                  90                  95
Pro Phe Gly Leu Asp Thr Ile Ile Thr Pro Asn Leu Phe Pro Gly Val
            100                 105                 110
Ser Ile Ser Ala Asp Leu Gly Asn Gly Pro Gly Ile Gln Glu Val Ala
```

```
              115                 120                 125
Thr Phe Ser Val Asp Val Lys Gly Ala Lys Gly Ala Val Ala Val Ser
            130                 135                 140

Asn Ala His Gly Thr Val Thr Gly Ala Ala Gly Gly Val Leu Leu Arg
145                 150                 155                 160

Pro Phe Ala Arg Leu Ile Ala Ser Thr Gly Asp Ser Val Thr Thr Tyr
                165                 170                 175

Gly Glu Pro Trp Asn Met Asn
            180

<210> SEQ ID NO 8
<211> LENGTH: 1830
<212> TYPE: DNA
<213> ORGANISM: Artificial Sequence
<220> FEATURE:
<223> OTHER INFORMATION: Phi29 DNA polymerase

<400> SEQUENCE: 8
atgaaacaca tgccgcgtaa aatgtatagc tgcgcgtttg aaaccacgac caaagtggaa      60
gattgtcgcg tttgggccta tggctacatg aacatcgaag atcattctga atacaaaatc     120
ggtaacagtc tggatgaatt tatggcatgg gtgctgaaag ttcaggcgga tctgtacttc     180
cacaacctga atttgatgg cgcattcatt atcaactggc tggaacgtaa tggctttaaa     240 tggagcgcg atggtctgcc gaacacgtat aataccatta tctctcgtat gggccagtgg     300
tatatgattg atatctgcct gggctacaaa ggtaaacgca aaattcatac cgtgatctat     360
gatagcctga aaaactgcc gtttccggtg aagaaaattg cgaaagattt caaactgacg     420
gttctgaaag gcgatattga ttatcacaaa gaacgtccgg ttggttacaa aatcacccg     480 gaagaatacg catacatcaa aaacgatatc cagatcatcg cagaagcgct gctgattcag     540
tttaaacagg gcctggatcg catgaccgcg ggcagtgata gcctgaaagg tttcaaagat     600
atcatcacga ccaaaaaatt caaaaaagtg ttcccgacgc tgagcctggg tctggataaa     660
gaagttcgtt atgcctaccg cggcggtttt acctggctga cgatcgtttt caaagaaaaa     720
gaaattggcg agggtatggt gttgatgtt aatagtctgt atccggcaca gatgtacagc     780
cgcctgctgc gtatggcga accgatcgtg ttcgagggta atatgtttg ggatgaagat     840 tacccgctgc atattcagca catccgttgt gaatttgaac tgaaagaagg ctatattccg     900
accattcaga tcaaacgtag tcgcttctat aagggtaacg aatacctgaa aagctctggc     960
ggtgaaatcg cggatctgtg gctgagtaac gtggatctgg aactgatgaa agaacactac    1020
gatctgtaca cgttgaata tcagcggc ctgaaattta agccacgac cggtctgttc      1080 aaagatttca tcgataaatg gacctacatc aaaacgacct ctgaaggcgc gattaaacag    1140
ctggccaaac tgatgctgaa cagcctgtat ggcaaattcg cctctaatcc ggatgtgacc    1200
ggtaaagttc cgtacctgaa agaaaatggc gcactgggtt ttcgcctggg cgaagaagaa    1260
acgaaagatc cggtgtatac cccgatgggt gttttcatta cggcctgggc acgttacacg    1320
accatcaccg cggcccaggc atgctatgat cgcattatct actgtgatac cgattctatt    1380
catctgacgg gcaccgaaat cccgatgtg attaaagata tcgttgatcc gaaaaaactg    1440
ggttattggg cccacgaaag tacgtttaaa cgtgcaaaat acctgcgcca gaaaacctac    1500
atccaggata tctacatgaa agaagtggat ggcaaactgg ttgaaggttc tccggatgat    1560
tacaccgata tcaaattcag tgtgaaatgc gccggcatga cggataaaat caaaaaagaa    1620
gtgaccttcg aaaacttcaa agttggtttc agccgcaaaa tgaaaccgaa accggtgcag    1680
```

```
gttccgggcg gtgtggttct ggtggatgat acgtttacca ttaaatctgg cggtagtgcg   1740
tggagccatc cgcagttcga aaaggcggt  ggctctggtg gcggttctgg cggtagtgcc    1800
tggagccacc cgcagtttga aaaataataa                                     1830
```

```
<210> SEQ ID NO 9
<211> LENGTH: 608
<212> TYPE: PRT
<213> ORGANISM: Artificial Sequence
<220> FEATURE:
<223> OTHER INFORMATION: Phi29 DNA polymerase

<400> SEQUENCE: 9
```

```
Met Lys His Met Pro Arg Lys Met Tyr Ser Cys Ala Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335
```

```
Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
            355                 360                 365

Tyr Ile Lys Thr Thr Ser Glu Gly Ala Ile Lys Gln Leu Ala Lys Leu
        370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
            435                 440                 445

Tyr Asp Arg Ile Ile Tyr Cys Asp Thr Asp Ser Ile His Leu Thr Gly
        450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Phe Ser Val
            515                 520                 525

Lys Cys Ala Gly Met Thr Asp Lys Ile Lys Lys Glu Val Thr Phe Glu
530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys Ser
                565                 570                 575

Gly Gly Ser Ala Trp Ser His Pro Gln Phe Glu Lys Gly Gly Ser
            580                 585                 590

Gly Gly Gly Ser Gly Gly Ser Ala Trp Ser His Pro Gln Phe Glu Lys
            595                 600                 605

<210> SEQ ID NO 10
<211> LENGTH: 1390
<212> TYPE: DNA
<213> ORGANISM: Artificial Sequence
<220> FEATURE:
<223> OTHER INFORMATION: WT EcoExo I

<400> SEQUENCE: 10
atgatgaacg atggcaaaca gcagagcacc ttcctgtttc atgattatga aaccttcggt      60
acccatccgg ccctggatcg tccggcgcag tttgcggcca ttcgcaccga tagcgaattc     120
aatgtgattg cgaaccgga agtgttttat tgcaaaccgg ccgatgatta tctgccgcag     180
ccgggtgcgg tgctgattac cggtattacc ccgcaggaag cgcgcgcgaa aggtgaaaac     240
gaagcggcgt tgccgcgcg cattcatagc ctgtttaccg tgccgaaaac ctgcattctg     300
ggctataaca atgtgcgctt cgatgatgaa gttacccgta atatctttta tcgtaacttt     360
tatgatccgt atgcgtggag ctggcagcat gataacagcc gttgggatct gctggatgtg     420 atgcgcgcg gctatgcgct cgccccggaa ggcattaatt ggccggaaaa cgatgatggc     480
ctgccgagct ttcgtctgga acatctgacc aaagccaacg gcattgaaca tagcaatgcc     540
```

```
catgatgcga tggccgatgt ttatgcgacc attgcgatgg cgaaactggt taaaacccgt    600
cagccgcgcc tgtttgatta tctgtttacc caccgtaaca acacaaaact gatggcgctg    660
attgatgttc gcagatgaa accgctggtg catgtgagcg gcatgtttgg cgcctggcgc    720
ggcaacacca gctgggtggc cccgctggcc tggcacccgg aaaatcgtaa cgccgtgatt    780
atggttgatc tggccggtga tattagcccg ctgctggaac tggatagcga taccctgcgt    840
gaacgcctgt ataccgccaa aaccgatctg gcgataatg ccgccgtgcc ggtgaaactg    900
gttcacatta caaatgccc ggtgctggcc caggcgaaca ccctgcgccc ggaagatgcg    960
gatcgtctgg gtattaatcg ccagcattgt ctggataatc tgaaaatcct gcgtgaaaac   1020
ccgcaggtgc gtgaaaaagt ggtggcgatc ttcgcggaag cggaaccgtt caccccgagc   1080
gataacgtgg atgcgcagct gtataacggc ttctttagcg atgccgatcg cgcggcgatg   1140
aaaatcgttc tggaaaccga accgcgcaat ctgccggcgc tggatattac ctttgttgat   1200
aaacgtattg aaaaactgct gtttaattat cgtgcgcgca attttccggg taccctggat   1260
tatgccgaac agcagcgttg gctggaacat cgtcgtcagg ttttcacccc ggaatttctg   1320
cagggttatg cggatgaact gcagatgctg gttcagcagt atgccgatga taaagaaaaa   1380
gtggcgctgc                                                          1390
```

<210> SEQ ID NO 11
<211> LENGTH: 485
<212> TYPE: PRT
<213> ORGANISM: Artificial Sequence
<220> FEATURE:
<223> OTHER INFORMATION: WT EcoExo I

<400> SEQUENCE: 11

```
Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
        35                  40                  45

Phe Tyr Cys Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Cys Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
        115                 120                 125

Gln His Asp Asn Ser Arg Trp Asp Leu Leu Asp Val Met Arg Ala Cys
    130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
            180                 185                 190

Met Ala Lys Leu Val Lys Thr Arg Gln Pro Arg Leu Phe Asp Tyr Leu
        195                 200                 205
```

```
Phe Thr His Arg Asn Lys His Lys Leu Met Ala Leu Ile Asp Val Pro
    210                 215                 220
Gln Met Lys Pro Leu Val His Val Ser Gly Met Phe Gly Ala Trp Arg
225                 230                 235                 240
Gly Asn Thr Ser Trp Val Ala Pro Leu Ala Trp His Pro Glu Asn Arg
                245                 250                 255
Asn Ala Val Ile Met Val Asp Leu Ala Gly Asp Ile Ser Pro Leu Leu
            260                 265                 270
Glu Leu Asp Ser Asp Thr Leu Arg Glu Arg Leu Tyr Thr Ala Lys Thr
        275                 280                 285
Asp Leu Gly Asp Asn Ala Ala Val Pro Val Lys Leu Val His Ile Asn
    290                 295                 300
Lys Cys Pro Val Leu Ala Gln Ala Asn Thr Leu Arg Pro Glu Asp Ala
305                 310                 315                 320
Asp Arg Leu Gly Ile Asn Arg Gln His Cys Leu Asp Asn Leu Lys Ile
                325                 330                 335
Leu Arg Glu Asn Pro Gln Val Arg Glu Lys Val Val Ala Ile Phe Ala
            340                 345                 350
Glu Ala Glu Pro Phe Thr Pro Ser Asp Asn Val Asp Ala Gln Leu Tyr
        355                 360                 365
Asn Gly Phe Phe Ser Asp Ala Asp Arg Ala Ala Met Lys Ile Val Leu
    370                 375                 380
Glu Thr Glu Pro Arg Asn Leu Pro Ala Leu Asp Ile Thr Phe Val Asp
385                 390                 395                 400
Lys Arg Ile Glu Lys Leu Leu Phe Asn Tyr Arg Ala Arg Asn Phe Pro
                405                 410                 415
Gly Thr Leu Asp Tyr Ala Glu Gln Gln Arg Trp Leu Glu His Arg Arg
            420                 425                 430
Gln Val Phe Thr Pro Glu Phe Leu Gln Gly Tyr Ala Asp Glu Leu Gln
        435                 440                 445
Met Leu Val Gln Gln Tyr Ala Asp Asp Lys Glu Lys Val Ala Leu Leu
    450                 455                 460
Lys Ala Leu Trp Gln Tyr Ala Glu Glu Ile Val Ser Gly Ser Gly His
465                 470                 475                 480
His His His His
            485

<210> SEQ ID NO 12
<211> LENGTH: 804
<212> TYPE: DNA
<213> ORGANISM: Artificial Sequence
<220> FEATURE:
<223> OTHER INFORMATION: exonuclease III enzyme from E. coli

<400> SEQUENCE: 12
atgaaatttg tctcttttaa tatcaacggc ctgcgcgcca gacctcacca gcttgaagcc      60
atcgtcgaaa agcaccaacc ggatgtgatt ggcctgcagg agacaaaagt tcatgacgat     120
atgtttccgc tcgaagaggt ggcgaagctc ggctacaacg tgttttatca cgggcagaaa     180
ggccattatg gcgtggcgct gctgaccaaa gagacgccga ttgccgtgcg tcgcggcttt     240
cccggtgacg acgaagaggc gcagcggcgg attattatgg cggaaatccc ctcactgctg     300
ggtaatgtca ccgtgatcaa cggttacttc ccgcagggtg aaagccgcga ccatccgata     360
aaattcccgg caaaagcgca gttttatcag aatctgcaaa actacctgga aaccgaactc     420
```

```
aaacgtgata atccggtact gattatgggc gatatgaata tcagccctac agatctggat    480
atcggcattg gcgaagaaaa ccgtaagcgc tggctgcgta ccggtaaatg ctctttcctg    540
ccggaagagc gcgaatggat ggacaggctg atgagctggg ggttggtcga taccttccgc    600
catgcgaatc cgcaaacagc agatcgtttc tcatggtttg attaccgctc aaaaggtttt    660
gacgataacc gtggtctgcg catcgacctg ctgctcgcca gccaaccgct ggcagaatgt    720
tgcgtagaaa ccggcatcga ctatgaaatc cgcagcatgg aaaaaccgtc cgatcacgcc    780
cccgtctggg cgaccttccg ccgc                                           804
```

<210> SEQ ID NO 13
<211> LENGTH: 268
<212> TYPE: PRT
<213> ORGANISM: Artificial Sequence
<220> FEATURE:
<223> OTHER INFORMATION: exonuclease III enzyme from E. coli

<400> SEQUENCE: 13

```
Met Lys Phe Val Ser Phe Asn Ile Asn Gly Leu Arg Ala Arg Pro His
1               5                   10                  15

Gln Leu Glu Ala Ile Val Glu Lys His Gln Pro Asp Val Ile Gly Leu
            20                  25                  30

Gln Glu Thr Lys Val His Asp Asp Met Phe Pro Leu Glu Glu Val Ala
        35                  40                  45

Lys Leu Gly Tyr Asn Val Phe Tyr His Gly Gln Lys Gly His Tyr Gly
    50                  55                  60

Val Ala Leu Leu Thr Lys Glu Thr Pro Ile Ala Val Arg Arg Gly Phe
65                  70                  75                  80

Pro Gly Asp Asp Glu Glu Ala Gln Arg Arg Ile Ile Met Ala Glu Ile
                85                  90                  95

Pro Ser Leu Leu Gly Asn Val Thr Val Ile Asn Gly Tyr Phe Pro Gln
            100                 105                 110

Gly Glu Ser Arg Asp His Pro Ile Lys Phe Pro Ala Lys Ala Gln Phe
        115                 120                 125

Tyr Gln Asn Leu Gln Asn Tyr Leu Glu Thr Glu Leu Lys Arg Asp Asn
    130                 135                 140

Pro Val Leu Ile Met Gly Asp Met Asn Ile Ser Pro Thr Asp Leu Asp
145                 150                 155                 160

Ile Gly Ile Gly Glu Glu Asn Arg Lys Arg Trp Leu Arg Thr Gly Lys
                165                 170                 175

Cys Ser Phe Leu Pro Glu Glu Arg Glu Trp Met Asp Arg Leu Met Ser
            180                 185                 190

Trp Gly Leu Val Asp Thr Phe Arg His Ala Asn Pro Gln Thr Ala Asp
        195                 200                 205

Arg Phe Ser Trp Phe Asp Tyr Arg Ser Lys Gly Phe Asp Asp Asn Arg
    210                 215                 220

Gly Leu Arg Ile Asp Leu Leu Leu Ala Ser Gln Pro Leu Ala Glu Cys
225                 230                 235                 240

Cys Val Glu Thr Gly Ile Asp Tyr Glu Ile Arg Ser Met Glu Lys Pro
                245                 250                 255

Ser Asp His Ala Pro Val Trp Ala Thr Phe Arg Arg
            260                 265
```

<210> SEQ ID NO 14
<211> LENGTH: 1275
<212> TYPE: DNA

<213> ORGANISM: Artificial Sequence
<220> FEATURE:
<223> OTHER INFORMATION: TthRecJ-cd

<400> SEQUENCE: 14

```
atgtttcgtc gtaaagaaga tctggatccg ccgctggcac tgctgccgct gaaaggcctg      60
cgcgaagccg ccgcactgct ggaagaagcg ctgcgtcaag gtaaacgcat cgtgttcac     120
ggcgactatg atgcggatgg cctgaccggc accgcgatcc tggttcgtgg tctgccgcc    180
ctgggtgcgg atgttcatcc gtttatcccg caccgcctgg aagaaggcta tggtgtcctg    240
atggaacgcg tcccggaaca tctggaagcc tcggacctgt ttctgaccgt tgactgcggc    300
attaccaacc atgcggaact gcgcgaactg ctggaaaatg gcgtggaagt cattgttacc    360
gatcatcata cgccgggcaa aacgccgccc ccgggtctgg tcgtgcatcc ggcgctgacg    420
ccggatctga agaaaaaacc gaccggcgca ggcgtggcgt ttctgctgct gtgggcactg    480
catgaacgcc tgggcctgcc gccgccgctg aatacgcgg acctggcagc cgttggcacc    540
attgccgacg ttgccccgct gtggggttgg aatcgtgcac tggtgaaaga aggtctggca    600
cgcatcccgg cttcatcttg ggtgggcctg cgtctgctgg ctgaagccgt gggctatacc    660
ggcaaagcgg tcgaagtcgc tttccgcatc gcgccgcgca tcaatgcggc ttcccgcctg    720
ggcgaagcgg aaaaagccct gcgcctgctg ctgacggatg atgcggcaga agctcaggcg    780
ctggtcggcg aactgcaccg tctgaacgcc gtcgtcaga ccctgaaaga agcgatgctg    840
cgcaaactgc tgccgcaggc cgacccggaa gcgaaagcca tcgttctgct ggacccggaa    900
ggccatccgg tgttatggg tattgtggcc tctcgcatcc tggaagcgac cctgcgcccg    960
gtctttctgg tggcccaggg caaaggcacc gtgcgttcgc tggctccgat tccgccgtc   1020
gaagcactgc gcagcgcgga agatctgctg ctgcgttatg gtggtcataa agaagcggcg   1080
ggtttcgcaa tggatgaagc gctgtttccg gcgttcaaag cacgcgttga agcgtatgcc   1140
gcacgttttcc cggatccggt tcgtgaagtg gcactgctgg atctgctgcc ggaaccgggc   1200
ctgctgccgc aggtgttccg tgaactggca ctgctggaac cgtatggtga aggtaacccg   1260
gaaccgctgt cctg                                                     1275
```

<210> SEQ ID NO 15
<211> LENGTH: 425
<212> TYPE: PRT
<213> ORGANISM: Artificial Sequence
<220> FEATURE:
<223> OTHER INFORMATION: TthRecJ-cd

<400> SEQUENCE: 15

```
Met Phe Arg Arg Lys Glu Asp Leu Asp Pro Pro Leu Ala Leu Leu Pro
1               5                   10                  15

Leu Lys Gly Leu Arg Glu Ala Ala Ala Leu Leu Glu Glu Ala Leu Arg
            20                  25                  30

Gln Gly Lys Arg Ile Arg Val His Gly Asp Tyr Asp Ala Asp Gly Leu
        35                  40                  45

Thr Gly Thr Ala Ile Leu Val Arg Gly Leu Ala Ala Leu Gly Ala Asp
    50                  55                  60

Val His Pro Phe Ile Pro His Arg Leu Glu Glu Gly Tyr Gly Val Leu
65                  70                  75                  80

Met Glu Arg Val Pro Glu His Leu Glu Ala Ser Asp Leu Phe Leu Thr
                85                  90                  95

Val Asp Cys Gly Ile Thr Asn His Ala Glu Leu Arg Glu Leu Leu Glu
```

|     | 100 |     |     | 105 |     |     | 110 |     |     |
| --- | --- | --- | --- | --- | --- | --- | --- | --- | --- |

Asn Gly Val Glu Val Ile Val Thr Asp His His Thr Pro Gly Lys Thr
               115                 120                 125

Pro Pro Pro Gly Leu Val Val His Pro Ala Leu Thr Pro Asp Leu Lys
       130                 135                 140

Glu Lys Pro Thr Gly Ala Gly Val Ala Phe Leu Leu Trp Ala Leu
145                 150                 155                 160

His Glu Arg Leu Gly Leu Pro Pro Leu Glu Tyr Ala Asp Leu Ala
               165                 170                 175

Ala Val Gly Thr Ile Ala Asp Val Ala Pro Leu Trp Gly Trp Asn Arg
               180                 185                 190

Ala Leu Val Lys Glu Gly Leu Ala Arg Ile Pro Ala Ser Ser Trp Val
               195                 200                 205

Gly Leu Arg Leu Leu Ala Glu Ala Val Gly Tyr Thr Gly Lys Ala Val
               210                 215                 220

Glu Val Ala Phe Arg Ile Ala Pro Arg Ile Asn Ala Ala Ser Arg Leu
225                 230                 235                 240

Gly Glu Ala Glu Lys Ala Leu Arg Leu Leu Leu Thr Asp Asp Ala Ala
               245                 250                 255

Glu Ala Gln Ala Leu Val Gly Glu Leu His Arg Leu Asn Ala Arg Arg
               260                 265                 270

Gln Thr Leu Glu Glu Ala Met Leu Arg Lys Leu Leu Pro Gln Ala Asp
               275                 280                 285

Pro Glu Ala Lys Ala Ile Val Leu Leu Asp Pro Glu Gly His Pro Gly
               290                 295                 300

Val Met Gly Ile Val Ala Ser Arg Ile Leu Glu Ala Thr Leu Arg Pro
305                 310                 315                 320

Val Phe Leu Val Ala Gln Gly Lys Gly Thr Val Arg Ser Leu Ala Pro
               325                 330                 335

Ile Ser Ala Val Glu Ala Leu Arg Ser Ala Glu Asp Leu Leu Leu Arg
               340                 345                 350

Tyr Gly Gly His Lys Glu Ala Ala Gly Phe Ala Met Asp Glu Ala Leu
               355                 360                 365

Phe Pro Ala Phe Lys Ala Arg Val Glu Ala Tyr Ala Ala Arg Phe Pro
       370                 375                 380

Asp Pro Val Arg Glu Val Ala Leu Leu Asp Leu Leu Pro Glu Pro Gly
385                 390                 395                 400

Leu Leu Pro Gln Val Phe Arg Glu Leu Ala Leu Leu Glu Pro Tyr Gly
               405                 410                 415

Glu Gly Asn Pro Glu Pro Leu Phe Leu
               420                 425

<210> SEQ ID NO 16
<211> LENGTH: 738
<212> TYPE: DNA
<213> ORGANISM: Artificial Sequence
<220> FEATURE:
<223> OTHER INFORMATION: bacteriophage lambda exo (redX)

<400> SEQUENCE: 16
tccggaagcg gctctggtag tggttctggc atgacaccgg acattatcct gcagcgtacc    60
gggatcgatg tgagagctgt cgaacagggg gatgatgcgt ggcacaaatt acggctcggc   120
gtcatcaccg cttcagaagt tcacaacgtg atagcaaaac cccgctccgg aaagaagtgg   180
cctgacatga aaatgtccta cttccacacc ctgcttgctg aggtttgcac cggtgtggct   240

```
ccggaagtta acgctaaagc actggcctgg ggaaaacagt acgagaacga cgccagaacc    300
ctgtttgaat tcacttccgg cgtgaatgtt actgaatccc cgatcatcta tcgcgacgaa    360
agtatgcgta ccgcctgctc tcccgatggt ttatgcagtg acggcaacgg ccttgaactg    420
aaatgcccgt ttacctcccg ggatttcatg aagttccggc tcggtggttt cgaggccata    480
aagtcagctt acatggccca ggtgcagtac agcatgtggg tgacgcgaaa aaatgcctgg    540
tactttgcca actatgaccc gcgtatgaag cgtgaaggcc tgcattatgt cgtgattgag    600
cgggatgaaa agtacatggc gagttttgac gagatcgtgc cggagttcat cgaaaaaatg    660
gacgaggcac tggctgaaat tggttttgta tttggggagc aatggcgatc tggctctggt    720
tccggcagcg gttccgga                                                  738
```

```
<210> SEQ ID NO 17
<211> LENGTH: 226
<212> TYPE: PRT
<213> ORGANISM: Artificial Sequence
<220> FEATURE:
<223> OTHER INFORMATION: bacteriophage lambda exo (redX)

<400> SEQUENCE: 17

Met Thr Pro Asp Ile Ile Leu Gln Arg Thr Gly Ile Asp Val Arg Ala
1               5                   10                  15

Val Glu Gln Gly Asp Asp Ala Trp His Lys Leu Arg Leu Gly Val Ile
            20                  25                  30

Thr Ala Ser Glu Val His Asn Val Ile Ala Lys Pro Arg Ser Gly Lys
        35                  40                  45

Lys Trp Pro Asp Met Lys Met Ser Tyr Phe His Thr Leu Leu Ala Glu
    50                  55                  60

Val Cys Thr Gly Val Ala Pro Glu Val Asn Ala Lys Ala Leu Ala Trp
65                  70                  75                  80

Gly Lys Gln Tyr Glu Asn Asp Ala Arg Thr Leu Phe Glu Phe Thr Ser
                85                  90                  95

Gly Val Asn Val Thr Glu Ser Pro Ile Ile Tyr Arg Asp Glu Ser Met
            100                 105                 110

Arg Thr Ala Cys Ser Pro Asp Gly Leu Cys Ser Asp Gly Asn Gly Leu
        115                 120                 125

Glu Leu Lys Cys Pro Phe Thr Ser Arg Asp Phe Met Lys Phe Arg Leu
    130                 135                 140

Gly Gly Phe Glu Ala Ile Lys Ser Ala Tyr Met Ala Gln Val Gln Tyr
145                 150                 155                 160

Ser Met Trp Val Thr Arg Lys Asn Ala Trp Tyr Phe Ala Asn Tyr Asp
                165                 170                 175

Pro Arg Met Lys Arg Glu Gly Leu His Tyr Val Val Ile Glu Arg Asp
            180                 185                 190

Glu Lys Tyr Met Ala Ser Phe Asp Glu Ile Val Pro Glu Phe Ile Glu
        195                 200                 205

Lys Met Asp Glu Ala Leu Ala Glu Ile Gly Phe Val Phe Gly Glu Gln
    210                 215                 220

Trp Arg
225
```

```
<210> SEQ ID NO 18
<211> LENGTH: 760
<212> TYPE: PRT
<213> ORGANISM: Artificial Sequence
```

<220> FEATURE:
<223> OTHER INFORMATION: Hel308 Mbu

<400> SEQUENCE: 18

```
Met Met Ile Arg Glu Leu Asp Ile Pro Arg Asp Ile Gly Phe Tyr
1               5                   10                  15

Glu Asp Ser Gly Ile Lys Glu Leu Tyr Pro Pro Gln Ala Glu Ala Ile
                20                  25                  30

Glu Met Gly Leu Leu Glu Lys Lys Asn Leu Leu Ala Ala Ile Pro Thr
        35                  40                  45

Ala Ser Gly Lys Thr Leu Leu Ala Glu Leu Ala Met Ile Lys Ala Ile
    50                  55                  60

Arg Glu Gly Gly Lys Ala Leu Tyr Ile Val Pro Leu Arg Ala Leu Ala
65                  70                  75                  80

Ser Glu Lys Phe Glu Arg Phe Lys Glu Leu Ala Pro Phe Gly Ile Lys
                85                  90                  95

Val Gly Ile Ser Thr Gly Asp Leu Asp Ser Arg Ala Asp Trp Leu Gly
                100                 105                 110

Val Asn Asp Ile Ile Val Ala Thr Ser Glu Lys Thr Asp Ser Leu Leu
            115                 120                 125

Arg Asn Gly Thr Ser Trp Met Asp Glu Ile Thr Thr Val Val Val Asp
    130                 135                 140

Glu Ile His Leu Leu Asp Ser Lys Asn Arg Gly Pro Thr Leu Glu Val
145                 150                 155                 160

Thr Ile Thr Lys Leu Met Arg Leu Asn Pro Asp Val Gln Val Val Ala
                165                 170                 175

Leu Ser Ala Thr Val Gly Asn Ala Arg Glu Met Ala Asp Trp Leu Gly
                180                 185                 190

Ala Ala Leu Val Leu Ser Glu Trp Arg Pro Thr Asp Leu His Glu Gly
            195                 200                 205

Val Leu Phe Gly Asp Ala Ile Asn Phe Pro Gly Ser Gln Lys Lys Ile
            210                 215                 220

Asp Arg Leu Glu Lys Asp Asp Ala Val Asn Leu Val Leu Asp Thr Ile
225                 230                 235                 240

Lys Ala Glu Gly Gln Cys Leu Val Phe Glu Ser Ser Arg Arg Asn Cys
                245                 250                 255

Ala Gly Phe Ala Lys Thr Ala Ser Ser Lys Val Ala Lys Ile Leu Asp
                260                 265                 270

Asn Asp Ile Met Ile Lys Leu Ala Gly Ile Ala Glu Glu Val Glu Ser
            275                 280                 285

Thr Gly Glu Thr Asp Thr Ala Ile Val Leu Ala Asn Cys Ile Arg Lys
    290                 295                 300

Gly Val Ala Phe His His Ala Gly Leu Asn Ser Asn His Arg Lys Leu
305                 310                 315                 320

Val Glu Asn Gly Phe Arg Gln Asn Leu Ile Lys Val Ile Ser Ser Thr
                325                 330                 335

Pro Thr Leu Ala Ala Gly Leu Asn Leu Pro Ala Arg Arg Val Ile Ile
                340                 345                 350

Arg Ser Tyr Arg Arg Phe Asp Ser Asn Phe Gly Met Gln Pro Ile Pro
            355                 360                 365

Val Leu Glu Tyr Lys Gln Met Ala Gly Arg Ala Gly Arg Pro His Leu
            370                 375                 380

Asp Pro Tyr Gly Glu Ser Val Leu Leu Ala Lys Thr Tyr Asp Glu Phe
385                 390                 395                 400
```

```
Ala Gln Leu Met Glu Asn Tyr Val Glu Ala Asp Ala Glu Asp Ile Trp
            405                 410                 415

Ser Lys Leu Gly Thr Glu Asn Ala Leu Arg Thr His Val Leu Ser Thr
        420                 425                 430

Ile Val Asn Gly Phe Ala Ser Thr Arg Gln Glu Leu Phe Asp Phe Phe
            435                 440                 445

Gly Ala Thr Phe Phe Ala Tyr Gln Gln Asp Lys Trp Met Leu Glu Glu
450                 455                 460

Val Ile Asn Asp Cys Leu Glu Phe Leu Ile Asp Lys Ala Met Val Ser
465                 470                 475                 480

Glu Thr Glu Asp Ile Glu Asp Ala Ser Lys Leu Phe Leu Arg Gly Thr
                485                 490                 495

Arg Leu Gly Ser Leu Val Ser Met Leu Tyr Ile Asp Pro Leu Ser Gly
            500                 505                 510

Ser Lys Ile Val Asp Gly Phe Lys Asp Ile Gly Lys Ser Thr Gly Gly
        515                 520                 525

Asn Met Gly Ser Leu Glu Asp Asp Lys Gly Asp Asp Ile Thr Val Thr
            530                 535                 540

Asp Met Thr Leu Leu His Leu Val Cys Ser Thr Pro Asp Met Arg Gln
545                 550                 555                 560

Leu Tyr Leu Arg Asn Thr Asp Tyr Thr Ile Val Asn Glu Tyr Ile Val
                565                 570                 575

Ala His Ser Asp Glu Phe His Glu Ile Pro Asp Lys Leu Lys Glu Thr
            580                 585                 590

Asp Tyr Glu Trp Phe Met Gly Glu Val Lys Thr Ala Met Leu Leu Glu
        595                 600                 605

Glu Trp Val Thr Glu Val Ser Ala Glu Asp Ile Thr Arg His Phe Asn
610                 615                 620

Val Gly Glu Gly Asp Ile His Ala Leu Ala Asp Thr Ser Glu Trp Leu
625                 630                 635                 640

Met His Ala Ala Ala Lys Leu Ala Glu Leu Leu Gly Val Glu Tyr Ser
                645                 650                 655

Ser His Ala Tyr Ser Leu Glu Lys Arg Ile Arg Tyr Gly Ser Gly Leu
            660                 665                 670

Asp Leu Met Glu Leu Val Gly Ile Arg Gly Val Gly Arg Val Arg Ala
        675                 680                 685

Arg Lys Leu Tyr Asn Ala Gly Phe Val Ser Val Ala Lys Leu Lys Gly
        690                 695                 700

Ala Asp Ile Ser Val Leu Ser Lys Leu Val Gly Pro Lys Val Ala Tyr
705                 710                 715                 720

Asn Ile Leu Ser Gly Ile Gly Val Arg Val Asn Asp Lys His Phe Asn
                725                 730                 735

Ser Ala Pro Ile Ser Ser Asn Thr Leu Asp Thr Leu Leu Asp Lys Asn
            740                 745                 750

Gln Lys Thr Phe Asn Asp Phe Gln
        755                 760

<210> SEQ ID NO 19
<211> LENGTH: 707
<212> TYPE: PRT
<213> ORGANISM: Artificial Sequence
<220> FEATURE:
<223> OTHER INFORMATION: Hel308 Csy

<400> SEQUENCE: 19
```

```
Met Arg Ile Ser Glu Leu Asp Ile Pro Arg Pro Ala Ile Glu Phe Leu
1               5                   10                  15

Glu Gly Glu Gly Tyr Lys Lys Leu Tyr Pro Pro Gln Ala Ala Ala Ala
                20                  25                  30

Lys Ala Gly Leu Thr Asp Gly Lys Ser Val Leu Val Ser Ala Pro Thr
            35                  40                  45

Ala Ser Gly Lys Thr Leu Ile Ala Ala Ile Ala Met Ile Ser His Leu
        50                  55                  60

Ser Arg Asn Arg Gly Lys Ala Val Tyr Leu Ser Pro Leu Arg Ala Leu
65                      70                  75                  80

Ala Ala Glu Lys Phe Ala Glu Phe Gly Lys Ile Gly Ile Pro Leu
                85                  90                  95

Gly Arg Pro Val Arg Val Gly Val Ser Thr Gly Asp Phe Glu Lys Ala
                100                 105                 110

Gly Arg Ser Leu Gly Asn Asn Asp Ile Leu Val Leu Thr Asn Glu Arg
            115                 120                 125

Met Asp Ser Leu Ile Arg Arg Pro Asp Trp Met Asp Glu Val Gly
        130                 135                 140

Leu Val Ile Ala Asp Glu Ile His Leu Ile Gly Asp Arg Ser Arg Gly
145                 150                 155                 160

Pro Thr Leu Glu Met Val Leu Thr Lys Leu Arg Gly Leu Arg Ser Ser
                165                 170                 175

Pro Gln Val Val Ala Leu Ser Ala Thr Ile Ser Asn Ala Asp Glu Ile
            180                 185                 190

Ala Gly Trp Leu Asp Cys Thr Leu Val His Ser Thr Trp Arg Pro Val
        195                 200                 205

Pro Leu Ser Glu Gly Val Tyr Gln Asp Gly Glu Val Ala Met Gly Asp
    210                 215                 220

Gly Ser Arg His Glu Val Ala Ala Thr Gly Gly Pro Ala Val Asp
225                 230                 235                 240

Leu Ala Ala Glu Ser Val Ala Glu Gly Gly Gln Ser Leu Ile Phe Ala
                245                 250                 255

Asp Thr Arg Ala Arg Ser Ala Ser Leu Ala Ala Lys Ala Ser Ala Val
            260                 265                 270

Ile Pro Glu Ala Lys Gly Ala Asp Ala Ala Lys Leu Ala Ala Ala
    275                 280                 285

Lys Lys Ile Ile Ser Ser Gly Gly Glu Thr Leu Ala Lys Thr Leu
    290                 295                 300

Ala Glu Leu Val Glu Lys Gly Ala Ala Phe His His Ala Gly Leu Asn
305                 310                 315                 320

Gln Asp Cys Arg Ser Val Val Glu Glu Phe Arg Ser Gly Arg Ile
            325                 330                 335

Arg Leu Leu Ala Ser Thr Pro Thr Leu Ala Ala Gly Val Asn Leu Pro
            340                 345                 350

Ala Arg Arg Val Val Ile Ser Ser Val Met Arg Tyr Asn Ser Ser Ser
        355                 360                 365

Gly Met Ser Glu Pro Ile Ser Ile Leu Glu Tyr Lys Gln Leu Cys Gly
    370                 375                 380

Arg Ala Gly Arg Pro Gln Tyr Asp Lys Ser Gly Glu Ala Ile Val Val
385                 390                 395                 400

Gly Gly Val Asn Ala Asp Glu Ile Phe Asp Arg Tyr Ile Gly Gly Glu
            405                 410                 415
```

-continued

```
Pro Glu Pro Ile Arg Ser Ala Met Val Asp Asp Arg Ala Leu Arg Ile
            420                 425                 430

His Val Leu Ser Leu Val Thr Thr Ser Pro Gly Ile Lys Glu Asp Asp
        435                 440                 445

Val Thr Glu Phe Phe Leu Gly Thr Leu Gly Gln Gln Ser Gly Glu
    450                 455                 460

Ser Thr Val Lys Phe Ser Val Ala Val Ala Leu Arg Phe Leu Gln Glu
465                 470                 475                 480

Glu Gly Met Leu Gly Arg Arg Gly Gly Arg Leu Ala Ala Thr Lys Met
                485                 490                 495

Gly Arg Leu Val Ser Arg Leu Tyr Met Asp Pro Met Thr Ala Val Thr
            500                 505                 510

Leu Arg Asp Ala Val Gly Glu Ala Ser Pro Gly Arg Met His Thr Leu
        515                 520                 525

Gly Phe Leu His Leu Val Ser Glu Cys Ser Glu Phe Met Pro Arg Phe
    530                 535                 540

Ala Leu Arg Gln Lys Asp His Glu Val Ala Glu Met Met Leu Glu Ala
545                 550                 555                 560

Gly Arg Gly Glu Leu Leu Arg Pro Val Tyr Ser Tyr Glu Cys Gly Arg
                565                 570                 575

Gly Leu Leu Ala Leu His Arg Trp Ile Gly Glu Ser Pro Glu Ala Lys
            580                 585                 590

Leu Ala Glu Asp Leu Lys Phe Glu Ser Gly Asp Val His Arg Met Val
        595                 600                 605

Glu Ser Ser Gly Trp Leu Leu Arg Cys Ile Trp Glu Ile Ser Lys His
610                 615                 620

Gln Glu Arg Pro Asp Leu Leu Gly Glu Leu Asp Val Leu Arg Ser Arg
625                 630                 635                 640

Val Ala Tyr Gly Ile Lys Ala Glu Leu Val Pro Leu Val Ser Ile Lys
                645                 650                 655

Gly Ile Gly Arg Val Arg Ser Arg Arg Leu Phe Arg Gly Gly Ile Lys
            660                 665                 670

Gly Pro Gly Asp Leu Ala Ala Val Pro Val Glu Arg Leu Ser Arg Val
        675                 680                 685

Glu Gly Ile Gly Ala Thr Leu Ala Asn Asn Ile Lys Ser Gln Leu Arg
    690                 695                 700

Lys Gly Gly
705
```

<210> SEQ ID NO 20
<211> LENGTH: 720
<212> TYPE: PRT
<213> ORGANISM: Artificial Sequence
<220> FEATURE:
<223> OTHER INFORMATION: Hel308 Tga

<400> SEQUENCE: 20

```
Met Lys Val Asp Glu Leu Pro Val Asp Glu Arg Leu Lys Ala Val Leu
1               5                   10                  15

Lys Glu Arg Gly Ile Glu Glu Leu Tyr Pro Pro Gln Ala Glu Ala Leu
            20                  25                  30

Lys Ser Gly Ala Leu Glu Gly Arg Asn Leu Val Leu Ala Ile Pro Thr
        35                  40                  45

Ala Ser Gly Lys Thr Leu Val Ser Glu Ile Val Met Val Asn Lys Leu
    50                  55                  60
```

Ile Gln Glu Gly Gly Lys Ala Val Tyr Leu Val Pro Leu Lys Ala Leu
 65                  70                  75                  80

Ala Glu Glu Lys Tyr Arg Glu Phe Lys Glu Trp Glu Lys Leu Gly Leu
                 85                  90                  95

Lys Val Ala Ala Thr Gly Asp Tyr Asp Ser Thr Asp Asp Trp Leu
            100                 105                 110

Gly Arg Tyr Asp Ile Ile Val Ala Thr Ala Glu Lys Phe Asp Ser Leu
            115                 120                 125

Leu Arg His Gly Ala Arg Trp Ile Asn Asp Val Lys Leu Val Val Ala
        130                 135                 140

Asp Glu Val His Leu Ile Gly Ser Tyr Asp Arg Gly Ala Thr Leu Glu
145                 150                 155                 160

Met Ile Leu Thr His Met Leu Gly Arg Ala Gln Ile Leu Ala Leu Ser
                165                 170                 175

Ala Thr Val Gly Asn Ala Glu Glu Leu Ala Glu Trp Leu Asp Ala Ser
                180                 185                 190

Leu Val Val Ser Asp Trp Arg Pro Val Gln Leu Arg Arg Gly Val Phe
            195                 200                 205

His Leu Gly Thr Leu Ile Trp Glu Asp Gly Lys Val Glu Ser Tyr Pro
        210                 215                 220

Glu Asn Trp Tyr Ser Leu Val Val Asp Ala Val Lys Arg Gly Lys Gly
225                 230                 235                 240

Ala Leu Val Phe Val Asn Thr Arg Arg Ser Ala Glu Lys Glu Ala Leu
                245                 250                 255

Ala Leu Ser Lys Leu Val Ser Ser His Leu Thr Lys Pro Glu Lys Arg
            260                 265                 270

Ala Leu Glu Ser Leu Ala Ser Gln Leu Glu Asp Asn Pro Thr Ser Glu
        275                 280                 285

Lys Leu Lys Arg Ala Leu Arg Gly Gly Val Ala Phe His His Ala Gly
290                 295                 300

Leu Ser Arg Val Glu Arg Thr Leu Ile Glu Asp Ala Phe Arg Glu Gly
305                 310                 315                 320

Leu Ile Lys Val Ile Thr Ala Thr Pro Thr Leu Ser Ala Gly Val Asn
                325                 330                 335

Leu Pro Ser Phe Arg Val Ile Ile Arg Asp Thr Lys Arg Tyr Ala Gly
            340                 345                 350

Phe Gly Trp Thr Asp Ile Pro Val Leu Glu Ile Gln Gln Met Met Gly
        355                 360                 365

Arg Ala Gly Arg Pro Arg Tyr Asp Lys Tyr Gly Glu Ala Ile Ile Val
370                 375                 380

Ala Arg Thr Asp Glu Pro Gly Lys Leu Met Glu Arg Tyr Ile Arg Gly
385                 390                 395                 400

Lys Pro Glu Lys Leu Phe Ser Met Leu Ala Asn Glu Gln Ala Phe Arg
                405                 410                 415

Ser Gln Val Leu Ala Leu Ile Thr Asn Phe Gly Ile Arg Ser Phe Pro
            420                 425                 430

Glu Leu Val Arg Phe Leu Glu Arg Thr Phe Tyr Ala His Gln Arg Lys
        435                 440                 445

Asp Leu Ser Ser Leu Glu Tyr Lys Ala Lys Glu Val Val Tyr Phe Leu
450                 455                 460

Ile Glu Asn Glu Phe Ile Asp Leu Asp Leu Glu Asp Arg Phe Ile Pro
465                 470                 475                 480

Leu Pro Phe Gly Lys Arg Thr Ser Gln Leu Tyr Ile Asp Pro Leu Thr

```
                        485                 490                 495
Ala Lys Lys Phe Lys Asp Ala Phe Pro Ala Ile Glu Arg Asn Pro Asn
                    500                 505                 510

Pro Phe Gly Ile Phe Gln Leu Ile Ala Ser Thr Pro Asp Met Ala Thr
                515                 520                 525

Leu Thr Ala Arg Arg Arg Glu Met Glu Asp Tyr Leu Asp Leu Ala Tyr
            530                 535                 540

Glu Leu Glu Asp Lys Leu Tyr Ala Ser Ile Pro Tyr Tyr Glu Asp Ser
545                 550                 555                 560

Arg Phe Gln Gly Phe Leu Gly Gln Val Lys Thr Ala Lys Val Leu Leu
                565                 570                 575

Asp Trp Ile Asn Glu Val Pro Glu Ala Arg Ile Tyr Glu Thr Tyr Ser
                580                 585                 590

Ile Asp Pro Gly Asp Leu Tyr Arg Leu Glu Leu Ala Asp Trp Leu
                595                 600                 605

Met Tyr Ser Leu Ile Glu Leu Tyr Lys Leu Phe Glu Pro Lys Glu Glu
                610                 615                 620

Ile Leu Asn Tyr Leu Arg Asp Leu His Leu Arg Leu Arg His Gly Val
625                 630                 635                 640

Arg Glu Glu Leu Leu Glu Leu Val Arg Leu Pro Asn Ile Gly Arg Lys
                645                 650                 655

Arg Ala Arg Ala Leu Tyr Asn Ala Gly Phe Arg Ser Val Glu Ala Ile
                660                 665                 670

Ala Asn Ala Lys Pro Ala Glu Leu Leu Ala Val Glu Gly Ile Gly Ala
                675                 680                 685

Lys Ile Leu Asp Gly Ile Tyr Arg His Leu Gly Ile Glu Lys Arg Val
                690                 695                 700

Thr Glu Glu Lys Pro Lys Arg Lys Gly Thr Leu Glu Asp Phe Leu Arg
705                 710                 715                 720
```

<210> SEQ ID NO 21
<211> LENGTH: 799
<212> TYPE: PRT
<213> ORGANISM: Artificial Sequence
<220> FEATURE:
<223> OTHER INFORMATION: Hel308 Mhu

<400> SEQUENCE: 21

```
Met Glu Ile Ala Ser Leu Pro Leu Pro Asp Ser Phe Ile Arg Ala Cys
1               5                   10                  15

His Ala Lys Gly Ile Arg Ser Leu Tyr Pro Pro Gln Ala Glu Cys Ile
                20                  25                  30

Glu Lys Gly Leu Leu Glu Gly Lys Asn Leu Leu Ile Ser Ile Pro Thr
            35                  40                  45

Ala Ser Gly Lys Thr Leu Leu Ala Glu Met Ala Met Trp Ser Arg Ile
50                  55                  60

Ala Ala Gly Gly Lys Cys Leu Tyr Ile Val Pro Leu Arg Ala Leu Ala
65                  70                  75                  80

Ser Glu Lys Tyr Asp Glu Phe Ser Lys Lys Gly Val Ile Arg Val Gly
                85                  90                  95

Ile Ala Thr Gly Asp Leu Asp Arg Thr Asp Ala Tyr Leu Gly Glu Asn
            100                 105                 110

Asp Ile Ile Val Ala Thr Ser Glu Lys Thr Asp Ser Leu Leu Arg Asn
            115                 120                 125

Arg Thr Pro Trp Leu Ser Gln Ile Thr Cys Ile Val Leu Asp Glu Val
```

```
              130                 135                 140
His Leu Ile Gly Ser Glu Asn Arg Gly Ala Thr Leu Glu Met Val Ile
145                 150                 155                 160

Thr Lys Leu Arg Tyr Thr Asn Pro Val Met Gln Ile Ile Gly Leu Ser
                165                 170                 175

Ala Thr Ile Gly Asn Pro Ala Gln Leu Ala Glu Trp Leu Asp Ala Thr
            180                 185                 190

Leu Ile Thr Ser Thr Trp Arg Pro Val Asp Leu Arg Gln Gly Val Tyr
        195                 200                 205

Tyr Asn Gly Lys Ile Arg Phe Ser Asp Ser Glu Arg Pro Ile Gln Gly
    210                 215                 220

Lys Thr Lys His Asp Asp Leu Asn Leu Cys Leu Asp Thr Ile Glu Glu
225                 230                 235                 240

Gly Gly Gln Cys Leu Val Phe Val Ser Ser Arg Arg Asn Ala Glu Gly
                245                 250                 255

Phe Ala Lys Lys Ala Ala Gly Ala Leu Lys Ala Gly Ser Pro Asp Ser
                260                 265                 270

Lys Ala Leu Ala Gln Glu Leu Arg Arg Leu Arg Asp Arg Asp Glu Gly
            275                 280                 285

Asn Val Leu Ala Asp Cys Val Glu Arg Gly Ala Ala Phe His His Ala
            290                 295                 300

Gly Leu Ile Arg Gln Glu Arg Thr Ile Ile Glu Glu Gly Phe Arg Asn
305                 310                 315                 320

Gly Tyr Ile Glu Val Ile Ala Ala Thr Pro Thr Leu Ala Ala Gly Leu
                325                 330                 335

Asn Leu Pro Ala Arg Arg Val Ile Ile Arg Asp Tyr Asn Arg Phe Ala
                340                 345                 350

Ser Gly Leu Gly Met Val Pro Ile Pro Val Gly Glu Tyr His Gln Met
            355                 360                 365

Ala Gly Arg Ala Gly Arg Pro His Leu Asp Pro Tyr Gly Glu Ala Val
        370                 375                 380

Leu Leu Ala Lys Asp Ala Pro Ser Val Glu Arg Leu Phe Glu Thr Phe
385                 390                 395                 400

Ile Asp Ala Glu Ala Glu Arg Val Asp Ser Gln Cys Val Asp Asp Ala
                405                 410                 415

Ser Leu Cys Ala His Ile Leu Ser Leu Ile Ala Thr Gly Phe Ala His
                420                 425                 430

Asp Gln Glu Ala Leu Ser Ser Phe Met Glu Arg Thr Phe Tyr Phe Phe
            435                 440                 445

Gln His Pro Lys Thr Arg Ser Leu Pro Arg Leu Val Ala Asp Ala Ile
    450                 455                 460

Arg Phe Leu Thr Thr Ala Gly Met Val Glu Arg Glu Asn Thr Leu
465                 470                 475                 480

Ser Ala Thr Arg Leu Gly Ser Leu Val Ser Arg Leu Tyr Leu Asn Pro
                485                 490                 495

Cys Thr Ala Arg Leu Ile Leu Asp Ser Leu Lys Ser Cys Lys Thr Pro
                500                 505                 510

Thr Leu Ile Gly Leu Leu His Val Ile Cys Val Ser Pro Asp Met Gln
            515                 520                 525

Arg Leu Tyr Leu Lys Ala Ala Asp Thr Gln Leu Leu Arg Thr Phe Leu
        530                 535                 540

Phe Lys His Lys Asp Asp Leu Ile Leu Pro Leu Pro Phe Glu Gln Glu
545                 550                 555                 560
```

```
Glu Glu Glu Leu Trp Leu Ser Gly Leu Lys Thr Ala Leu Val Leu Thr
                565                 570                 575

Asp Trp Ala Asp Glu Phe Ser Glu Gly Met Ile Glu Arg Tyr Gly
            580                 585                 590

Ile Gly Ala Gly Asp Leu Tyr Asn Ile Val Asp Ser Gly Lys Trp Leu
                595                 600                 605

Leu His Gly Thr Glu Arg Leu Val Ser Val Glu Met Pro Glu Met Ser
                610                 615                 620

Gln Val Val Lys Thr Leu Ser Val Arg Val His His Gly Val Lys Ser
625                 630                 635                 640

Glu Leu Leu Pro Leu Val Ala Leu Arg Asn Ile Gly Arg Val Arg Ala
                645                 650                 655

Arg Thr Leu Tyr Asn Ala Gly Tyr Pro Asp Pro Glu Ala Val Ala Arg
                660                 665                 670

Ala Gly Leu Ser Thr Ile Ala Arg Ile Ile Gly Glu Gly Ile Ala Arg
                675                 680                 685

Gln Val Ile Asp Glu Ile Thr Gly Val Lys Arg Ser Gly Ile His Ser
                690                 695                 700

Ser Asp Asp Asp Tyr Gln Gln Lys Thr Pro Glu Leu Leu Thr Asp Ile
705                 710                 715                 720

Pro Gly Ile Gly Lys Lys Met Ala Glu Lys Leu Gln Asn Ala Gly Ile
                725                 730                 735

Ile Thr Val Ser Asp Leu Leu Thr Ala Asp Glu Val Leu Leu Ser Asp
                740                 745                 750

Val Leu Gly Ala Ala Arg Ala Arg Lys Val Leu Ala Phe Leu Ser Asn
                755                 760                 765

Ser Glu Lys Glu Asn Ser Ser Ser Asp Lys Thr Glu Glu Ile Pro Asp
770                 775                 780

Thr Gln Lys Ile Arg Gly Gln Ser Ser Trp Glu Asp Phe Gly Cys
785                 790                 795

<210> SEQ ID NO 22
<211> LENGTH: 1756
<212> TYPE: PRT
<213> ORGANISM: Artificial Sequence
<220> FEATURE:
<223> OTHER INFORMATION: TraI Eco

<400> SEQUENCE: 22

Met Met Ser Ile Ala Gln Val Arg Ser Ala Gly Ser Ala Gly Asn Tyr
1               5                   10                  15

Tyr Thr Asp Lys Asp Asn Tyr Tyr Val Leu Gly Ser Met Gly Glu Arg
                20                  25                  30

Trp Ala Gly Lys Gly Ala Glu Gln Leu Gly Leu Gln Gly Ser Val Asp
                35                  40                  45

Lys Asp Val Phe Thr Arg Leu Leu Glu Gly Arg Leu Pro Asp Gly Ala
            50                  55                  60

Asp Leu Ser Arg Met Gln Asp Gly Ser Asn Lys His Arg Pro Gly Tyr
65                  70                  75                  80

Asp Leu Thr Phe Ser Ala Pro Lys Ser Val Ser Met Met Ala Met Leu
                85                  90                  95

Gly Gly Asp Lys Arg Leu Ile Asp Ala His Asn Gln Ala Val Asp Phe
                100                 105                 110

Ala Val Arg Gln Val Glu Ala Leu Ala Ser Thr Arg Val Met Thr Asp
                115                 120                 125
```

```
Gly Gln Ser Glu Thr Val Leu Thr Gly Asn Leu Val Met Ala Leu Phe
        130                 135                 140

Asn His Asp Thr Ser Arg Asp Gln Glu Pro Gln Leu His Thr His Ala
145                 150                 155                 160

Val Val Ala Asn Val Thr Gln His Asn Gly Glu Trp Lys Thr Leu Ser
                165                 170                 175

Ser Asp Lys Val Gly Lys Thr Gly Phe Ile Glu Asn Val Tyr Ala Asn
            180                 185                 190

Gln Ile Ala Phe Gly Arg Leu Tyr Arg Glu Lys Leu Lys Glu Gln Val
        195                 200                 205

Glu Ala Leu Gly Tyr Glu Thr Glu Val Val Gly Lys His Gly Met Trp
    210                 215                 220

Glu Met Pro Gly Val Pro Val Glu Ala Phe Ser Gly Arg Ser Gln Ala
225                 230                 235                 240

Ile Arg Glu Ala Val Gly Glu Asp Ala Ser Leu Lys Ser Arg Asp Val
                245                 250                 255

Ala Ala Leu Asp Thr Arg Lys Ser Lys Gln His Val Asp Pro Glu Ile
            260                 265                 270

Arg Met Ala Glu Trp Met Gln Thr Leu Lys Glu Thr Gly Phe Asp Ile
        275                 280                 285

Arg Ala Tyr Arg Asp Ala Ala Asp Gln Arg Thr Glu Ile Arg Thr Gln
    290                 295                 300

Ala Pro Gly Pro Ala Ser Gln Asp Gly Pro Asp Val Gln Gln Ala Val
305                 310                 315                 320

Thr Gln Ala Ile Ala Gly Leu Ser Glu Arg Lys Val Gln Phe Thr Tyr
                325                 330                 335

Thr Asp Val Leu Ala Arg Thr Val Gly Ile Leu Pro Pro Glu Asn Gly
            340                 345                 350

Val Ile Glu Arg Ala Arg Ala Gly Ile Asp Glu Ala Ile Ser Arg Glu
        355                 360                 365

Gln Leu Ile Pro Leu Asp Arg Glu Lys Gly Leu Phe Thr Ser Gly Ile
    370                 375                 380

His Val Leu Asp Glu Leu Ser Val Arg Ala Leu Ser Arg Asp Ile Met
385                 390                 395                 400

Lys Gln Asn Arg Val Thr Val His Pro Glu Lys Ser Val Pro Arg Thr
                405                 410                 415

Ala Gly Tyr Ser Asp Ala Val Ser Val Leu Ala Gln Asp Arg Pro Ser
            420                 425                 430

Leu Ala Ile Val Ser Gly Gln Gly Ala Ala Gly Gln Arg Glu Arg
        435                 440                 445

Val Ala Glu Leu Val Met Met Ala Arg Glu Gln Gly Arg Glu Val Gln
    450                 455                 460

Ile Ile Ala Ala Asp Arg Arg Ser Gln Met Asn Leu Lys Gln Asp Glu
465                 470                 475                 480

Arg Leu Ser Gly Glu Leu Ile Thr Gly Arg Arg Gln Leu Leu Glu Gly
                485                 490                 495

Met Ala Phe Thr Pro Gly Ser Thr Val Ile Val Asp Gln Gly Glu Lys
            500                 505                 510

Leu Ser Leu Lys Glu Thr Leu Thr Leu Leu Asp Gly Ala Ala Arg His
        515                 520                 525

Asn Val Gln Val Leu Ile Thr Asp Ser Gly Gln Arg Thr Gly Thr Gly
530                 535                 540
```

```
Ser Ala Leu Met Ala Met Lys Asp Ala Gly Val Asn Thr Tyr Arg Trp
545                 550                 555                 560

Gln Gly Gly Glu Gln Arg Pro Ala Thr Ile Ile Ser Glu Pro Asp Arg
                565                 570                 575

Asn Val Arg Tyr Ala Arg Leu Ala Gly Asp Phe Ala Ala Ser Val Lys
            580                 585                 590

Ala Gly Glu Glu Ser Val Ala Gln Val Ser Gly Val Arg Glu Gln Ala
        595                 600                 605

Ile Leu Thr Gln Ala Ile Arg Ser Glu Leu Lys Thr Gln Gly Val Leu
    610                 615                 620

Gly His Pro Glu Val Thr Met Thr Ala Leu Ser Pro Val Trp Leu Asp
625                 630                 635                 640

Ser Arg Ser Arg Tyr Leu Arg Asp Met Tyr Arg Pro Gly Met Val Met
                645                 650                 655

Glu Gln Trp Asn Pro Glu Thr Arg Ser His Asp Arg Tyr Val Ile Asp
                660                 665                 670

Arg Val Thr Ala Gln Ser His Ser Leu Thr Leu Arg Asp Ala Gln Gly
            675                 680                 685

Glu Thr Gln Val Val Arg Ile Ser Ser Leu Asp Ser Ser Trp Ser Leu
        690                 695                 700

Phe Arg Pro Glu Lys Met Pro Val Ala Asp Gly Glu Arg Leu Arg Val
705                 710                 715                 720

Thr Gly Lys Ile Pro Gly Leu Arg Val Ser Gly Gly Asp Arg Leu Gln
                725                 730                 735

Val Ala Ser Val Ser Glu Asp Ala Met Thr Val Val Pro Gly Arg
            740                 745                 750

Ala Glu Pro Ala Ser Leu Pro Val Ser Asp Ser Pro Phe Thr Ala Leu
        755                 760                 765

Lys Leu Glu Asn Gly Trp Val Glu Thr Pro Gly His Ser Val Ser Asp
    770                 775                 780

Ser Ala Thr Val Phe Ala Ser Val Thr Gln Met Ala Met Asp Asn Ala
785                 790                 795                 800

Thr Leu Asn Gly Leu Ala Arg Ser Gly Arg Asp Val Arg Leu Tyr Ser
                805                 810                 815

Ser Leu Asp Glu Thr Arg Thr Ala Glu Lys Leu Ala Arg His Pro Ser
            820                 825                 830

Phe Thr Val Val Ser Glu Gln Ile Lys Ala Arg Ala Gly Glu Thr Leu
        835                 840                 845

Leu Glu Thr Ala Ile Ser Leu Gln Lys Ala Gly Leu His Thr Pro Ala
    850                 855                 860

Gln Gln Ala Ile His Leu Ala Leu Pro Val Leu Glu Ser Lys Asn Leu
865                 870                 875                 880

Ala Phe Ser Met Val Asp Leu Leu Thr Glu Ala Lys Ser Phe Ala Ala
                885                 890                 895

Glu Gly Thr Gly Phe Thr Glu Leu Gly Gly Glu Ile Asn Ala Gln Ile
            900                 905                 910

Lys Arg Gly Asp Leu Leu Tyr Val Asp Val Ala Lys Gly Tyr Gly Thr
        915                 920                 925

Gly Leu Leu Val Ser Arg Ala Ser Tyr Glu Ala Glu Lys Ser Ile Leu
    930                 935                 940

Arg His Ile Leu Glu Gly Lys Glu Ala Val Thr Pro Leu Met Glu Arg
945                 950                 955                 960

Val Pro Gly Glu Leu Met Glu Thr Leu Thr Ser Gly Gln Arg Ala Ala
```

-continued

```
            965                 970                 975
Thr Arg Met Ile Leu Glu Thr Ser Asp Arg Phe Thr Val Val Gln Gly
                980                 985                 990
Tyr Ala Gly Val Gly Lys Thr Thr Gln Phe Arg Ala Val Met Ser Ala
            995                1000                1005
Val Asn Met Leu Pro Ala Ser Glu Arg Pro Arg Val Val Gly Leu
           1010                1015                1020
Gly Pro Thr His Arg Ala Val Gly Glu Met Arg Ser Ala Gly Val
           1025                1030                1035
Asp Ala Gln Thr Leu Ala Ser Phe Leu His Asp Thr Gln Leu Gln
           1040                1045                1050
Gln Arg Ser Gly Glu Thr Pro Asp Phe Ser Asn Thr Leu Phe Leu
           1055                1060                1065
Leu Asp Glu Ser Ser Met Val Gly Asn Thr Glu Met Ala Arg Ala
           1070                1075                1080
Tyr Ala Leu Ile Ala Ala Gly Gly Gly Arg Ala Val Ala Ser Gly
           1085                1090                1095
Asp Thr Asp Gln Leu Gln Ala Ile Ala Pro Gly Gln Ser Phe Arg
           1100                1105                1110
Leu Gln Gln Thr Arg Ser Ala Ala Asp Val Val Ile Met Lys Glu
           1115                1120                1125
Ile Val Arg Gln Thr Pro Glu Leu Arg Glu Ala Val Tyr Ser Leu
           1130                1135                1140
Ile Asn Arg Asp Val Glu Arg Ala Leu Ser Gly Leu Glu Ser Val
           1145                1150                1155
Lys Pro Ser Gln Val Pro Arg Leu Glu Gly Ala Trp Ala Pro Glu
           1160                1165                1170
His Ser Val Thr Glu Phe Ser His Ser Gln Glu Ala Lys Leu Ala
           1175                1180                1185
Glu Ala Gln Gln Lys Ala Met Leu Lys Gly Glu Ala Phe Pro Asp
           1190                1195                1200
Ile Pro Met Thr Leu Tyr Glu Ala Ile Val Arg Asp Tyr Thr Gly
           1205                1210                1215
Arg Thr Pro Glu Ala Arg Glu Gln Thr Leu Ile Val Thr His Leu
           1220                1225                1230
Asn Glu Asp Arg Arg Val Leu Asn Ser Met Ile His Asp Ala Arg
           1235                1240                1245
Glu Lys Ala Gly Glu Leu Gly Lys Glu Gln Val Met Val Pro Val
           1250                1255                1260
Leu Asn Thr Ala Asn Ile Arg Asp Gly Glu Leu Arg Arg Leu Ser
           1265                1270                1275
Thr Trp Glu Lys Asn Pro Asp Ala Leu Ala Leu Val Asp Asn Val
           1280                1285                1290
Tyr His Arg Ile Ala Gly Ile Ser Lys Asp Asp Gly Leu Ile Thr
           1295                1300                1305
Leu Gln Asp Ala Glu Gly Asn Thr Arg Leu Ile Ser Pro Arg Glu
           1310                1315                1320
Ala Val Ala Glu Gly Val Thr Leu Tyr Thr Pro Asp Lys Ile Arg
           1325                1330                1335
Val Gly Thr Gly Asp Arg Met Arg Phe Thr Lys Ser Asp Arg Glu
           1340                1345                1350
Arg Gly Tyr Val Ala Asn Ser Val Trp Thr Val Thr Ala Val Ser
           1355                1360                1365
```

```
Gly Asp Ser Val Thr Leu Ser Asp Gly Gln Gln Thr Arg Val Ile
    1370                1375                1380

Arg Pro Gly Gln Glu Arg Ala Glu Gln His Ile Asp Leu Ala Tyr
    1385                1390                1395

Ala Ile Thr Ala His Gly Ala Gln Gly Ala Ser Glu Thr Phe Ala
    1400                1405                1410

Ile Ala Leu Glu Gly Thr Glu Gly Asn Arg Lys Leu Met Ala Gly
    1415                1420                1425

Phe Glu Ser Ala Tyr Val Ala Leu Ser Arg Met Lys Gln His Val
    1430                1435                1440

Gln Val Tyr Thr Asp Asn Arg Gln Gly Trp Thr Asp Ala Ile Asn
    1445                1450                1455

Asn Ala Val Gln Lys Gly Thr Ala His Asp Val Leu Glu Pro Lys
    1460                1465                1470

Pro Asp Arg Glu Val Met Asn Ala Gln Arg Leu Phe Ser Thr Ala
    1475                1480                1485

Arg Glu Leu Arg Asp Val Ala Ala Gly Arg Ala Val Leu Arg Gln
    1490                1495                1500

Ala Gly Leu Ala Gly Gly Asp Ser Pro Ala Arg Phe Ile Ala Pro
    1505                1510                1515

Gly Arg Lys Tyr Pro Gln Pro Tyr Val Ala Leu Pro Ala Phe Asp
    1520                1525                1530

Arg Asn Gly Lys Ser Ala Gly Ile Trp Leu Asn Pro Leu Thr Thr
    1535                1540                1545

Asp Asp Gly Asn Gly Leu Arg Gly Phe Ser Gly Glu Gly Arg Val
    1550                1555                1560

Lys Gly Ser Gly Asp Ala Gln Phe Val Ala Leu Gln Gly Ser Arg
    1565                1570                1575

Asn Gly Glu Ser Leu Leu Ala Asp Asn Met Gln Asp Gly Val Arg
    1580                1585                1590

Ile Ala Arg Asp Asn Pro Asp Ser Gly Val Val Val Arg Ile Ala
    1595                1600                1605

Gly Glu Gly Arg Pro Trp Asn Pro Gly Ala Ile Thr Gly Gly Arg
    1610                1615                1620

Val Trp Gly Asp Ile Pro Asp Asn Ser Val Gln Pro Gly Ala Gly
    1625                1630                1635

Asn Gly Glu Pro Val Thr Ala Glu Val Leu Ala Gln Arg Gln Ala
    1640                1645                1650

Glu Glu Ala Ile Arg Arg Glu Thr Glu Arg Arg Ala Asp Glu Ile
    1655                1660                1665

Val Arg Lys Met Ala Glu Asn Lys Pro Asp Leu Pro Asp Gly Lys
    1670                1675                1680

Thr Glu Leu Ala Val Arg Asp Ile Ala Gly Gln Glu Arg Asp Arg
    1685                1690                1695

Ser Ala Ile Ser Glu Arg Glu Thr Ala Leu Pro Glu Ser Val Leu
    1700                1705                1710

Arg Glu Ser Gln Arg Glu Arg Glu Ala Val Arg Glu Val Ala Arg
    1715                1720                1725

Glu Asn Leu Leu Gln Glu Arg Leu Gln Gln Met Glu Arg Asp Met
    1730                1735                1740

Val Arg Asp Leu Gln Lys Glu Lys Thr Leu Gly Gly Asp
    1745                1750                1755
```

<210> SEQ ID NO 23
<211> LENGTH: 726
<212> TYPE: PRT
<213> ORGANISM: Artificial Sequence
<220> FEATURE:
<223> OTHER INFORMATION: XPD Mbu

<400> SEQUENCE: 23

```
Met Ser Asp Lys Pro Ala Phe Met Lys Tyr Phe Thr Gln Ser Cys
1               5                   10                  15

Tyr Pro Asn Gln Gln Glu Ala Met Asp Arg Ile His Ser Ala Leu Met
                20                  25                  30

Gln Gln Gln Leu Val Leu Phe Glu Gly Ala Cys Gly Thr Gly Lys Thr
            35                  40                  45

Leu Ser Ala Leu Val Pro Ala Leu His Val Gly Lys Met Leu Gly Lys
        50                  55                  60

Thr Val Ile Ile Ala Thr Asn Val His Gln Gln Met Val Gln Phe Ile
65                  70                  75                  80

Asn Glu Ala Arg Asp Ile Lys Lys Val Gln Asp Val Lys Val Ala Val
                85                  90                  95

Ile Lys Gly Lys Thr Ala Met Cys Pro Gln Glu Ala Asp Tyr Glu Glu
            100                 105                 110

Cys Ser Val Lys Arg Glu Asn Thr Phe Glu Leu Met Glu Thr Glu Arg
        115                 120                 125

Glu Ile Tyr Leu Lys Arg Gln Glu Leu Asn Ser Ala Arg Asp Ser Tyr
130                 135                 140

Lys Lys Ser His Asp Pro Ala Phe Val Thr Leu Arg Asp Glu Leu Ser
145                 150                 155                 160

Lys Glu Ile Asp Ala Val Glu Glu Lys Ala Arg Gly Leu Arg Asp Arg
                165                 170                 175

Ala Cys Asn Asp Leu Tyr Glu Val Leu Arg Ser Asp Ser Glu Lys Phe
            180                 185                 190

Arg Glu Trp Leu Tyr Lys Glu Val Arg Ser Pro Glu Glu Ile Asn Asp
        195                 200                 205

His Ala Ile Lys Asp Gly Met Cys Gly Tyr Glu Leu Val Lys Arg Glu
210                 215                 220

Leu Lys His Ala Asp Leu Leu Ile Cys Asn Tyr His His Val Leu Asn
225                 230                 235                 240

Pro Asp Ile Phe Ser Thr Val Leu Gly Trp Ile Glu Lys Glu Pro Gln
                245                 250                 255

Glu Thr Ile Val Ile Phe Asp Glu Ala His Asn Leu Glu Ser Ala Ala
            260                 265                 270

Arg Ser His Ser Ser Leu Ser Leu Thr Glu His Ser Ile Glu Lys Ala
        275                 280                 285

Ile Thr Glu Leu Glu Ala Asn Leu Asp Leu Leu Ala Asp Asp Asn Ile
290                 295                 300

His Asn Leu Phe Asn Ile Phe Leu Glu Val Ile Ser Asp Thr Tyr Asn
305                 310                 315                 320

Ser Arg Phe Lys Phe Gly Glu Arg Glu Arg Val Arg Lys Asn Trp Tyr
                325                 330                 335

Asp Ile Arg Ile Ser Asp Pro Tyr Glu Arg Asn Asp Ile Val Arg Gly
            340                 345                 350

Lys Phe Leu Arg Gln Ala Lys Gly Asp Phe Gly Glu Lys Asp Asp Ile
        355                 360                 365
```

```
Gln Ile Leu Leu Ser Glu Ala Ser Glu Leu Gly Ala Lys Leu Asp Glu
    370                 375                 380

Thr Tyr Arg Asp Gln Tyr Lys Lys Gly Leu Ser Ser Val Met Lys Arg
385                 390                 395                 400

Ser His Ile Arg Tyr Val Ala Asp Phe Met Ser Ala Tyr Ile Glu Leu
                405                 410                 415

Ser His Asn Leu Asn Tyr Tyr Pro Ile Leu Asn Val Arg Arg Asp Met
            420                 425                 430

Asn Asp Glu Ile Tyr Gly Arg Val Glu Leu Phe Thr Cys Ile Pro Lys
        435                 440                 445

Asn Val Thr Glu Pro Leu Phe Asn Ser Leu Phe Ser Val Ile Leu Met
450                 455                 460

Ser Ala Thr Leu His Pro Phe Glu Met Val Lys Lys Thr Leu Gly Ile
465                 470                 475                 480

Thr Arg Asp Thr Cys Glu Met Ser Tyr Gly Thr Ser Phe Pro Glu Glu
                485                 490                 495

Lys Arg Leu Ser Ile Ala Val Ser Ile Pro Pro Leu Phe Ala Lys Asn
            500                 505                 510

Arg Asp Asp Arg His Val Thr Glu Leu Leu Glu Gln Val Leu Leu Asp
        515                 520                 525

Ser Ile Glu Asn Ser Lys Gly Asn Val Ile Leu Phe Phe Gln Ser Ala
    530                 535                 540

Phe Glu Ala Lys Arg Tyr Tyr Ser Lys Ile Glu Pro Leu Val Asn Val
545                 550                 555                 560

Pro Val Phe Leu Asp Glu Val Gly Ile Ser Ser Gln Asp Val Arg Glu
                565                 570                 575

Glu Phe Phe Ser Ile Gly Glu Glu Asn Gly Lys Ala Val Leu Leu Ser
            580                 585                 590

Tyr Leu Trp Gly Thr Leu Ser Glu Gly Ile Asp Tyr Arg Asp Gly Arg
        595                 600                 605

Gly Arg Thr Val Ile Ile Ile Gly Val Gly Tyr Pro Ala Leu Asn Asp
    610                 615                 620

Arg Met Asn Ala Val Glu Ser Ala Tyr Asp His Val Phe Gly Tyr Gly
625                 630                 635                 640

Ala Gly Trp Glu Phe Ala Ile Gln Val Pro Thr Ile Arg Lys Ile Arg
                645                 650                 655

Gln Ala Met Gly Arg Val Val Arg Ser Pro Thr Asp Tyr Gly Ala Arg
            660                 665                 670

Ile Leu Leu Asp Gly Arg Phe Leu Thr Asp Ser Lys Lys Arg Phe Gly
        675                 680                 685

Lys Phe Ser Val Phe Glu Val Phe Pro Pro Ala Glu Arg Ser Glu Phe
    690                 695                 700

Val Asp Val Asp Pro Glu Lys Val Lys Tyr Ser Leu Met Asn Phe Phe
705                 710                 715                 720

Met Asp Asn Asp Glu Gln
                725

<210> SEQ ID NO 24
<211> LENGTH: 439
<212> TYPE: PRT
<213> ORGANISM: Artificial Sequence
<220> FEATURE:
<223> OTHER INFORMATION: Dda 1993

<400> SEQUENCE: 24
```

```
Met Thr Phe Asp Asp Leu Thr Glu Gly Gln Lys Asn Ala Phe Asn Ile
1               5                   10                  15

Val Met Lys Ala Ile Lys Glu Lys Lys His His Val Thr Ile Asn Gly
            20                  25                  30

Pro Ala Gly Thr Gly Lys Thr Thr Leu Thr Lys Phe Ile Ile Glu Ala
            35                  40                  45

Leu Ile Ser Thr Gly Glu Thr Gly Ile Ile Leu Ala Ala Pro Thr His
        50                  55                  60

Ala Ala Lys Lys Ile Leu Ser Lys Leu Ser Gly Lys Glu Ala Ser Thr
65                  70                  75                  80

Ile His Ser Ile Leu Lys Ile Asn Pro Val Thr Tyr Glu Glu Asn Val
                85                  90                  95

Leu Phe Glu Gln Lys Glu Val Pro Asp Leu Ala Lys Cys Arg Val Leu
            100                 105                 110

Ile Cys Asp Glu Val Ser Met Tyr Asp Arg Lys Leu Phe Lys Ile Leu
            115                 120                 125

Leu Ser Thr Ile Pro Pro Trp Cys Thr Ile Gly Ile Gly Asp Asn
        130                 135                 140

Lys Gln Ile Arg Pro Val Asp Pro Gly Glu Asn Thr Ala Tyr Ile Ser
145                 150                 155                 160

Pro Phe Phe Thr His Lys Asp Phe Tyr Gln Cys Glu Leu Thr Glu Val
                165                 170                 175

Lys Arg Ser Asn Ala Pro Ile Ile Asp Val Ala Thr Asp Val Arg Asn
                180                 185                 190

Gly Lys Trp Ile Tyr Asp Lys Val Val Asp Gly His Gly Val Arg Gly
            195                 200                 205

Phe Thr Gly Asp Thr Ala Leu Arg Asp Phe Met Val Asn Tyr Phe Ser
    210                 215                 220

Ile Val Lys Ser Leu Asp Asp Leu Phe Glu Asn Arg Val Met Ala Phe
225                 230                 235                 240

Thr Asn Lys Ser Val Asp Lys Leu Asn Ser Ile Ile Arg Lys Lys Ile
                245                 250                 255

Phe Glu Thr Asp Lys Asp Phe Ile Val Gly Glu Ile Ile Val Met Gln
            260                 265                 270

Glu Pro Leu Phe Lys Thr Tyr Lys Ile Asp Gly Lys Pro Val Ser Glu
        275                 280                 285

Ile Ile Phe Asn Asn Gly Gln Leu Val Arg Ile Ile Glu Ala Glu Tyr
        290                 295                 300

Thr Ser Thr Phe Val Lys Ala Arg Gly Val Pro Gly Glu Tyr Leu Ile
305                 310                 315                 320

Arg His Trp Asp Leu Thr Val Glu Thr Tyr Gly Asp Asp Glu Tyr Tyr
                325                 330                 335

Arg Glu Lys Ile Lys Ile Ile Ser Ser Asp Glu Glu Leu Tyr Lys Phe
                340                 345                 350

Asn Leu Phe Leu Gly Lys Thr Ala Glu Thr Tyr Lys Asn Trp Asn Lys
            355                 360                 365

Gly Gly Lys Ala Pro Trp Ser Asp Phe Trp Asp Ala Lys Ser Gln Phe
370                 375                 380

Ser Lys Val Lys Ala Leu Pro Ala Ser Thr Phe His Lys Ala Gln Gly
385                 390                 395                 400

Met Ser Val Asp Arg Ala Phe Ile Tyr Thr Pro Cys Ile His Tyr Ala
                405                 410                 415

Asp Val Glu Leu Ala Gln Gln Leu Leu Tyr Val Gly Val Thr Arg Gly
```

```
                420             425             430
Arg Tyr Asp Val Phe Tyr Val
        435

<210> SEQ ID NO 25
<211> LENGTH: 970
<212> TYPE: PRT
<213> ORGANISM: Artificial Sequence
<220> FEATURE:
<223> OTHER INFORMATION: TrwC Cba

<400> SEQUENCE: 25

Met Leu Ser Val Ala Asn Val Arg Ser Pro Ser Ala Ala Ser Tyr
1               5                   10                  15

Phe Ala Ser Asp Asn Tyr Tyr Ala Ser Ala Asp Ala Asp Arg Ser Gly
                20                  25                  30

Gln Trp Ile Gly Asp Gly Ala Lys Arg Leu Gly Leu Glu Gly Lys Val
            35                  40                  45

Glu Ala Arg Ala Phe Asp Ala Leu Leu Arg Gly Glu Leu Pro Asp Gly
50                  55                  60

Ser Ser Val Gly Asn Pro Gly Gln Ala His Arg Pro Gly Thr Asp Leu
65                  70                  75                  80

Thr Phe Ser Val Pro Lys Ser Trp Ser Leu Leu Ala Leu Val Gly Lys
                85                  90                  95

Asp Glu Arg Ile Ile Ala Ala Tyr Arg Glu Ala Val Val Glu Ala Leu
                100                 105                 110

His Trp Ala Glu Lys Asn Ala Ala Glu Thr Arg Val Val Glu Lys Gly
            115                 120                 125

Met Val Val Thr Gln Ala Thr Gly Asn Leu Ala Ile Gly Leu Phe Gln
130                 135                 140

His Asp Thr Asn Arg Asn Gln Glu Pro Asn Leu His Phe His Ala Val
145                 150                 155                 160

Ile Ala Asn Val Thr Gln Gly Lys Asp Gly Lys Trp Arg Thr Leu Lys
                165                 170                 175

Asn Asp Arg Leu Trp Gln Leu Asn Thr Thr Leu Asn Ser Ile Ala Met
                180                 185                 190

Ala Arg Phe Arg Val Ala Val Glu Lys Leu Gly Tyr Glu Pro Gly Pro
            195                 200                 205

Val Leu Lys His Gly Asn Phe Glu Ala Arg Gly Ile Ser Arg Glu Gln
            210                 215                 220

Val Met Ala Phe Ser Thr Arg Arg Lys Glu Val Leu Glu Ala Arg Arg
225                 230                 235                 240

Gly Pro Gly Leu Asp Ala Gly Arg Ile Ala Ala Leu Asp Thr Arg Ala
                245                 250                 255

Ser Lys Glu Gly Ile Glu Asp Arg Ala Thr Leu Ser Lys Gln Trp Ser
                260                 265                 270

Glu Ala Ala Gln Ser Ile Gly Leu Asp Leu Lys Pro Leu Val Asp Arg
            275                 280                 285

Ala Arg Thr Lys Ala Leu Gly Gln Gly Met Glu Ala Thr Arg Ile Gly
        290                 295                 300

Ser Leu Val Glu Arg Gly Arg Ala Trp Leu Ser Arg Phe Ala Ala His
305                 310                 315                 320

Val Arg Gly Asp Pro Ala Asp Pro Leu Val Pro Ser Val Leu Lys
                325                 330                 335

Gln Asp Arg Gln Thr Ile Ala Ala Ala Gln Ala Val Ala Ser Ala Val
```

```
                    340                 345                 350
Arg His Leu Ser Gln Arg Glu Ala Ala Phe Glu Arg Thr Ala Leu Tyr
                355                 360                 365
Lys Ala Ala Leu Asp Phe Gly Leu Pro Thr Thr Ile Ala Asp Val Glu
            370                 375                 380
Lys Arg Thr Arg Ala Leu Val Arg Ser Gly Asp Leu Ile Ala Gly Lys
385                 390                 395                 400
Gly Glu His Lys Gly Trp Leu Ala Ser Arg Asp Ala Val Val Thr Glu
                405                 410                 415
Gln Arg Ile Leu Ser Glu Val Ala Ala Gly Lys Gly Asp Ser Ser Pro
            420                 425                 430
Ala Ile Thr Pro Gln Lys Ala Ala Ser Val Gln Ala Ala Ala Leu
            435                 440                 445
Thr Gly Gln Gly Phe Arg Leu Asn Glu Gly Gln Leu Ala Ala Ala Arg
        450                 455                 460
Leu Ile Leu Ile Ser Lys Asp Arg Thr Ile Ala Val Gln Gly Ile Ala
465                 470                 475                 480
Gly Ala Gly Lys Ser Ser Val Leu Lys Pro Val Ala Glu Val Leu Arg
                485                 490                 495
Asp Glu Gly His Pro Val Ile Gly Leu Ala Ile Gln Asn Thr Leu Val
            500                 505                 510
Gln Met Leu Glu Arg Asp Thr Gly Ile Gly Ser Gln Thr Leu Ala Arg
        515                 520                 525
Phe Leu Gly Gly Trp Asn Lys Leu Leu Asp Asp Pro Gly Asn Val Ala
        530                 535                 540
Leu Arg Ala Glu Ala Gln Ala Ser Leu Lys Asp His Val Leu Val Leu
545                 550                 555                 560
Asp Glu Ala Ser Met Val Ser Asn Glu Asp Lys Glu Lys Leu Val Arg
                565                 570                 575
Leu Ala Asn Leu Ala Gly Val His Arg Leu Val Leu Ile Gly Asp Arg
            580                 585                 590
Lys Gln Leu Gly Ala Val Asp Ala Gly Lys Pro Phe Ala Leu Leu Gln
        595                 600                 605
Arg Ala Gly Ile Ala Arg Ala Glu Met Ala Thr Asn Leu Arg Ala Arg
        610                 615                 620
Asp Pro Val Val Arg Glu Ala Gln Ala Ala Gln Ala Gly Asp Val
625                 630                 635                 640
Arg Lys Ala Leu Arg His Leu Lys Ser His Thr Val Glu Ala Arg Gly
                645                 650                 655
Asp Gly Ala Gln Val Ala Ala Glu Thr Trp Leu Ala Leu Asp Lys Glu
            660                 665                 670
Thr Arg Ala Arg Thr Ser Ile Tyr Ala Ser Gly Arg Ala Ile Arg Ser
        675                 680                 685
Ala Val Asn Ala Ala Val Gln Gln Gly Leu Leu Ala Ser Arg Glu Ile
        690                 695                 700
Gly Pro Ala Lys Met Lys Leu Glu Val Leu Asp Arg Val Asn Thr Thr
705                 710                 715                 720
Arg Glu Glu Leu Arg His Leu Pro Ala Tyr Arg Ala Gly Arg Val Leu
                725                 730                 735
Glu Val Ser Arg Lys Gln Gln Ala Leu Gly Leu Phe Ile Gly Glu Tyr
            740                 745                 750
Arg Val Ile Gly Gln Asp Arg Lys Gly Lys Leu Val Glu Val Glu Asp
        755                 760                 765
```

-continued

```
Lys Arg Gly Lys Arg Phe Arg Phe Asp Pro Ala Arg Ile Arg Ala Gly
            770                 775                 780
Lys Gly Asp Asp Asn Leu Thr Leu Leu Glu Pro Arg Lys Leu Glu Ile
785                 790                 795                 800
His Glu Gly Asp Arg Ile Arg Trp Thr Arg Asn Asp His Arg Arg Gly
                805                 810                 815
Leu Phe Asn Ala Asp Gln Ala Arg Val Val Glu Ile Ala Asn Gly Lys
            820                 825                 830
Val Thr Phe Glu Thr Ser Lys Gly Asp Leu Val Glu Leu Lys Lys Asp
            835                 840                 845
Asp Pro Met Leu Lys Arg Ile Asp Leu Ala Tyr Ala Leu Asn Val His
850                 855                 860
Met Ala Gln Gly Leu Thr Ser Asp Arg Gly Ile Ala Val Met Asp Ser
865                 870                 875                 880
Arg Glu Arg Asn Leu Ser Asn Gln Lys Thr Phe Leu Val Thr Val Thr
                885                 890                 895
Arg Leu Arg Asp His Leu Thr Leu Val Val Asp Ser Ala Asp Lys Leu
            900                 905                 910
Gly Ala Ala Val Ala Arg Asn Lys Gly Glu Lys Ala Ser Ala Ile Glu
            915                 920                 925
Val Thr Gly Ser Val Lys Pro Thr Ala Thr Lys Gly Ser Gly Val Asp
930                 935                 940
Gln Pro Lys Ser Val Glu Ala Asn Lys Ala Glu Lys Glu Leu Thr Arg
945                 950                 955                 960
Ser Lys Ser Lys Thr Leu Asp Phe Gly Ile
                965                 970
```

<210> SEQ ID NO 26
<211> LENGTH: 786
<212> TYPE: DNA
<213> ORGANISM: Artificial Sequence
<220> FEATURE:
<223> OTHER INFORMATION: WT CsgG from E. coli Str. K-12 substr. MC4100

<400> SEQUENCE: 26

```
tgtctgaccg caccgccgaa agaagcggca cgtccgaccc tgatgccgcg tgcacagtct      60
tataaagatc tgacccatct gccggctccg acgggcaaaa ttttgttag cgtctataac     120
atccaggacg aaaccggtca atttaaaccg tacccggcga gtaatttctc cacggccgtt     180
ccgcagagtg caaccgctat gctggtcacg gcactgaaag attcccgttg gttcattccg     240
ctggaacgcc agggcctgca aaacctgctg aatgaacgta aaattatccg cgcagctcag     300
gaaaacggta ccgtgccat taacaatcgt attccgctgc aaagcctgac cgccgcaaac     360
atcatggttg aaggctctat catcggttac gaatcaaacg tcaaatcggg cggtgtgggc     420
gcacgttatt ttggcattgg tgctgatacc cagtaccaac tggaccagat cgcagttaac     480
ctgcgcgtgg ttaatgtcag caccggcgaa attctgagct ctgtgaatac cagcaaaacg     540
atcctgtctt acgaagtgca ggctggtgtt tttcgtttca ttgattatca acgcctgctg     600
gaaggcgaag tcggttacac ctcaaacgaa ccggtgatgc tgtgtctgat gtcggcgatt     660
gaaacgggtg ttatttttcct gatcaatgat ggcatcgacc gtggtctgtg ggatctgcag     720
aacaaagccg aacgtcaaaa tgacattctg gtgaaatacc gccacatgag tgttccgccg     780
gaatcc                                                                 786
```

```
<210> SEQ ID NO 27
<211> LENGTH: 262
<212> TYPE: PRT
<213> ORGANISM: Artificial Sequence
<220> FEATURE:
<223> OTHER INFORMATION: WT CsgG from E. coli Str. K-12 substr. MC4100

<400> SEQUENCE: 27

Cys Leu Thr Ala Pro Pro Lys Glu Ala Ala Arg Pro Thr Leu Met Pro
1               5                   10                  15

Arg Ala Gln Ser Tyr Lys Asp Leu Thr His Leu Pro Ala Pro Thr Gly
            20                  25                  30

Lys Ile Phe Val Ser Val Tyr Asn Ile Gln Asp Glu Thr Gly Gln Phe
        35                  40                  45

Lys Pro Tyr Pro Ala Ser Asn Phe Ser Thr Ala Val Pro Gln Ser Ala
    50                  55                  60

Thr Ala Met Leu Val Thr Ala Leu Lys Asp Ser Arg Trp Phe Ile Pro
65                  70                  75                  80

Leu Glu Arg Gln Gly Leu Gln Asn Leu Leu Asn Glu Arg Lys Ile Ile
                85                  90                  95

Arg Ala Ala Gln Glu Asn Gly Thr Val Ala Ile Asn Asn Arg Ile Pro
            100                 105                 110

Leu Gln Ser Leu Thr Ala Ala Asn Ile Met Val Glu Gly Ser Ile Ile
        115                 120                 125

Gly Tyr Glu Ser Asn Val Lys Ser Gly Gly Val Gly Ala Arg Tyr Phe
    130                 135                 140

Gly Ile Gly Ala Asp Thr Gln Tyr Gln Leu Asp Gln Ile Ala Val Asn
145                 150                 155                 160

Leu Arg Val Val Asn Val Ser Thr Gly Glu Ile Leu Ser Ser Val Asn
                165                 170                 175

Thr Ser Lys Thr Ile Leu Ser Tyr Glu Val Gln Ala Gly Val Phe Arg
            180                 185                 190

Phe Ile Asp Tyr Gln Arg Leu Leu Glu Gly Glu Val Gly Tyr Thr Ser
        195                 200                 205

Asn Glu Pro Val Met Leu Cys Leu Met Ser Ala Ile Glu Thr Gly Val
    210                 215                 220

Ile Phe Leu Ile Asn Asp Gly Ile Asp Arg Gly Leu Trp Asp Leu Gln
225                 230                 235                 240

Asn Lys Ala Glu Arg Gln Asn Asp Ile Leu Val Lys Tyr Arg His Met
                245                 250                 255

Ser Val Pro Pro Glu Ser
            260

<210> SEQ ID NO 28
<211> LENGTH: 3662
<212> TYPE: DNA
<213> ORGANISM: Artificial Sequence
<220> FEATURE:
<223> OTHER INFORMATION: DNA sequence 1 corrected
<220> FEATURE:
<221> NAME/KEY: misc_feature
<222> LOCATION: (46)..(47)
<223> OTHER INFORMATION: Modified by 4 iSpC3; C3 phosphoramidite spacer
<220> FEATURE:
<221> NAME/KEY: misc_feature
<222> LOCATION: (73)..(74)
<223> OTHER INFORMATION: Modified by 4 i5NitInd; 5-Nitroindole,
      universal base

<400> SEQUENCE: 28
```

```
tttttttttt tttttttttt tttttttttt tttttttttt tttttttggtt gtttctgttg    60
gtgctgatat tgcgccatca gattgtgttt gttagtcgct gccatcagat tgtgtttgtt   120
agtcgctttt ttttttttgga attttttttt tggaattttt tttttgcgct aacaacctcc   180
tgccgttttg cccgtgcata tcggtcacga acaaatctga ttactaaaca cagtagcctg   240
gatttgttct atcagtaatc gaccttattc ctaattaaat agagcaaatc cccttattgg   300
gggtaagaca tgaagatgcc agaaaaacat gacctgttgg ccgccattct cgcggcaaag   360
gaacaaggca tcggggcaat ccttgcgttt gcaatggcgt accttcgcgg cagatataat   420
ggcggtgcgt ttacaaaaac agtaatcgac gcaacgatgt cgccattat cgcctagttc    480
attcgtgacc ttctcgactt cgccggacta agtagcaatc tcgcttatat aacgagcgtg   540
tttatcggct acatcggtac tgactcgatt ggttcgctta tcaaacgctt cgctgctaaa   600
aaagccggag tagaagatgg tagaaatcaa taatcaacgt aaggcgttcc tcgatatgct   660
ggcgtggtcg gagggaactg ataacggacg tcagaaaacc agaaatcatg gttatgacgt   720
cattgtaggc ggagagctat ttactgatta ctccgatcac cctcgcaaac ttgtcacgct   780
aaacccaaaa ctcaaatcaa caggcgccgg acgctaccag cttctttccc gttggtggga   840
tgcctaccgc aagcagcttg gcctgaaaga cttctctccg aaaagtcagg acgctgtggc   900
attgcagcag attaaggagc gtggcgcttt acctatgatt gatcgtggtg atatccgtca   960
ggcaatcgac cgttgcagca atatctgggc ttcactgccg ggcgctggtt atggtcagtt  1020
cgagcataag gctgacagcc tgattgcaaa attcaaagaa gcgggcggaa cggtcagaga  1080
gattgatgta tgagcagagt caccgcgatt atctccgctc tggttatctg catcatcgtc  1140
tgcctgtcat gggctgttaa tcattaccgt gataacgcca ttacctacaa agcccagcgc  1200
gacaaaaatg ccagagaact gaagctggcg aacgcggcaa ttactgacat gcagatgcgt  1260
cagcgtgatg ttgctgcgct cgatgcaaaa tacacgaagg agttagctga tgctaaagct  1320
gaaaatgatg ctctgcgtga tgatgttgcc gctggtcgtc gtcggttgca catcaaagca  1380
gtctgtcagt cagtgcgtga agccaccacc gcctccggcg tggataatgc agcctccccc  1440
cgactggcag acaccgctga acgggattat ttcacccctca gagagaggct gatcactatg  1500
caaaaacaac tggaaggaac ccagaagtat attaatgagc agtgcagata gagttgccca  1560
tatcgatggg caactcatgc aattattgtg agcaatacac acgcgcttcc agcggagtat  1620
aaatgcctaa agtaataaaa ccgagcaatc catttacgaa tgtttgctgg gtttctgttt  1680
taacaacatt ttctgcgccg ccacaaattt tggctgcatc gacagttttc ttctgcccaa  1740
ttccagaaac gaagaaatga tgggtgatgg tttccttgg tgctactgct gccggtttgt    1800
tttgaacagt aaacgtctgt tgagcacatc ctgtaataag cagggccagc gcagtagcga  1860
gtagcatttt tttcatggtg ttattcccga tgcttttga agttcgcaga atcgtatgtg    1920
tagaaaatta aacaaaccct aaacaatgag ttgaaatttc atattgttaa tatttattaa  1980
tgtatgtcag gtgcgatgaa tcgtcattgt attcccggat taactatgtc cacagccctg  2040
acggggaact tctctgcggg agtgtccggg aataattaaa acgatgcaca cagggtttag  2100
cgcgtacacg tattgcatta tgccaacgcc ccggtgctga cacggaagaa accgacgtt    2160
atgatttagc gtggaaagat ttgtgtagtg ttctgaatgc tctcagtaaa tagtaatgaa  2220
ttatcaaagg tatagtaata tcttttatgt tcatggatat ttgtaaccca tcggaaaact  2280
cctgctttag caagattttc cctgtattgc tgaaatgtga tttctcttga tttcaaccta  2340
tcataggacg tttctataag atgcgtgttt cttgagaatt taacatttac aaccttttta  2400
```

| | |
|---|---|
| agtcctttta ttaacacggt gttatcgttt tctaacacga tgtgaatatt atctgtggct | 2460 |
| agatagtaaa tataatgtga gacgttgtga cgttttagtt cagaataaaa caattcacag | 2520 |
| tctaaatctt ttcgcacttg atcgaatatt tctttaaaaa tggcaacctg agccattggt | 2580 |
| aaaaccttcc atgtgatacg agggcgcgta gtttgcatta tcgtttttat cgtttcaatc | 2640 |
| tggtctgacc tccttgtgtt ttgttgatga tttatgtcaa atattaggaa tgttttcact | 2700 |
| taatagtatt ggttgcgtaa caaagtgcgg tcctgctggc attctggagg gaaatacaac | 2760 |
| cgacagatgt atgtaaggcc aacgtgctca aatcttcata cagaaagatt tgaagtaata | 2820 |
| ttttaaccgc tagatgaaga gcaagcgcat ggagcgacaa aatgaataaa gaacaatctg | 2880 |
| ctgatgatcc ctccgtggat ctgattcgtg taaaaaatat gcttaatagc accatttcta | 2940 |
| tgagttaccc tgatgttgta attgcatgta tagaacataa ggtgtctctg gaagcattca | 3000 |
| gagcaattga ggcagcgttg gtgaagcacg ataataatat gaaggattat tccctggtgg | 3060 |
| ttgactgatc accataactg ctaatcattc aaactattta gtctgtgaca gagccaacac | 3120 |
| gcagtctgtc actgtcagga aagtggtaaa actgcaactc aattactgca atgccctcgt | 3180 |
| aattaagtga atttacaata tcgtcctgtt cggagggaag aacgcgggat gttcattctt | 3240 |
| catcactttt aattgatgta tatgctctct tttctgacgt tagtctccga cggcaggctt | 3300 |
| caatgaccca ggctgagaaa ttcccggacc ctttttgctc aagagcgatg ttaatttgtt | 3360 |
| caatcatttg gttaggaaag cggatgttgc gggttgttgt tctgcgggtt ctgttcttcg | 3420 |
| ttgacatgag gttgccccgt attcagtgtc gctgatttgt attgtctgaa gttgttttta | 3480 |
| cgttaagttg atgcagatca attaatacga tacctgcgtc ataattgatt atttgacgtg | 3540 |
| gtttgatggc ctccacgcac gttgtgatat gtagatgata atcattatca ctttacgggt | 3600 |
| cctttccggt gaaaaaaaag gtaccaaaaa aaacatcgtc gtgagtagtg aaccgtaagc | 3660 |
| ac | 3662 |

<210> SEQ ID NO 29
<211> LENGTH: 3589
<212> TYPE: DNA
<213> ORGANISM: Artificial Sequence
<220> FEATURE:
<223> OTHER INFORMATION: DNA sequence 2 corrected

<400> SEQUENCE: 29

| | |
|---|---|
| gtgcttacgg ttcactactc acgacgatgt ttttttggt accttttttt tcaccggaaa | 60 |
| ggacccgtaa agtgataatg attatcatct acatatcaca acgtgcgtgg aggccatcaa | 120 |
| accacgtcaa ataatcaatt atgacgcagg tatcgtatta attgatctgc atcaacttaa | 180 |
| cgtaaaaaca acttcagaca atacaaatca gcgacactga atacggggca acctcatgtc | 240 |
| aacgaagaac agaacccgca gaacaacaac ccgcaacatc cgctttccta accaaatgat | 300 |
| tgaacaaatt aacatcgctc ttgagcaaaa agggtccggg aatttctcag cctgggtcat | 360 |
| tgaagcctgc cgtcggagac taacgtcaga aaagagagca tatacatcaa ttaaaagtga | 420 |
| tgaagaatga acatcccgcg ttcttccctc cgaacaggac gatattgtaa attcacttaa | 480 |
| ttacgagggc attgcagtaa ttgagttgca gttttaccac tttcctgaca gtgacagact | 540 |
| gcgtgttggc tctgtcacag actaaatagt tgaatgatt agcagttatg gtgatcagtc | 600 |
| aaccaccagg gaataatcct tcatattatt atcgtgcttc accaacgctg cctcaattgc | 660 |
| tctgaatgct tccagagaca ccttatgttc tatacatgca attacaacat cagggtaact | 720 |

```
catagaaatg gtgctattaa gcatattttt tacacgaatc agatccacgg agggatcatc        780
agcagattgt tctttattca ttttgtcgct ccatgcgctt gctcttcatc tagcggttaa        840
aatattactt caaatctttc tgtatgaaga tttgagcacg ttggccttac atacatctgt        900
cggttgtatt tccctccaga atgccagcag gaccgcactt tgttacgcaa ccaatactat        960
taagtgaaaa cattcctaat atttgacata aatcatcaac aaaacacaag gaggtcagac       1020
cagattgaaa cgataaaaac gataatgcaa actacgcgcc ctcgtatcac atggaaggtt       1080
ttaccaatgg ctcaggttgc catttttaaa gaaatattcg atcaagtgcg aaaagattta       1140
gactgtgaat tgttttattc tgaactaaaa cgtcacaacg tctcacatta tatttactat       1200
ctagccacag ataatattca catcgtgtta gaaaacgata acaccgtgtt aataaaagga       1260
cttaaaaagg ttgtaaatgt taaattctca agaaacacgc atcttataga aacgtcctat       1320
gataggttga aatcaagaga aatcacattt cagcaataca gggaaaatct tgctaaagca       1380
ggagttttcc gatgggttac aaatatccat gaacataaaa gatattacta tacctttgat       1440
aattcattac tatttactga gagcattcag aacactacac aaatctttcc acgctaaatc       1500
ataacgtccg gtttcttccg tgtcagcacc ggggcgttgg cataatgcaa tacgtgtacg       1560
cgctaaaccc tgtgtgcatc gttttaatta ttcccggaca ctcccgcaga gaagttcccc       1620
gtcagggctg tggacatagt taatccggga atacaatgac gattcatcgc acctgacata       1680
cattaataaa tattaacaat atgaaatttc aactcattgt ttagggtttg tttaattttc       1740
tacacatacg attctgcgaa cttcaaaaag catcgggaat aacaccatga aaaaaatgct       1800
actcgctact gcgctggccc tgcttattac aggatgtgct caacagacgt ttactgttca       1860
aaacaaaccg gcagcagtag caccaaagga aaccatcacc catcatttct tcgtttctgg       1920
aattgggcag aagaaaactg tcgatgcagc caaaatttgt ggcggcgcag aaaatgttgt       1980
taaaacagaa acccagcaaa cattcgtaaa tggattgctc ggttttatta ctttaggcat       2040
ttatactccg ctggaagcgc gtgtgtattg ctcacaataa ttgcatgagt tgcccatcga       2100
tatgggcaac tctatctgca ctgctcatta atatacttct gggttccttc cagttgtttt       2160
tgcatagtga tcagcctctc tctgagggtg aaataatccc gttcagcggt gtctgccagt       2220
cgggggggagg ctgcattatc cacgccggag gcggtggtgg cttcacgcac tgactgacag       2280
actgctttga tgtgcaaccg acgacgacca gcggcaacat catcacgcag agcatcattt       2340
tcagctttag catcagctaa ctccttcgtg tattttgcat cgagcgcagc aacatcacgc       2400
tgacgcatct gcatgtcagt aattgccgcg ttcgccagct tcagttctct ggcattttg       2460
tcgcgctggg ctttgtaggt aatggcgtta tcacggtaat gattaacagc ccatgacagg       2520
cagacgatga tgcagataac cagagcggag ataatcgcgg tgactctgct catacatcaa       2580
tctctctgac cgttccgccc gcttctttga attttgcaat caggctgtca gccttatgct       2640
cgaactgacc ataaccagcg cccggcagtg aagcccagat attgctgcaa cggtcgattg       2700
cctgacggat atcaccacga tcaatcatag gtaaagcgcc acgctcctta atctgctgca       2760
atgccacagc gtcctgactt ttcggagaga agtctttcag gccaagctgc ttgcggtagg       2820
catcccacca acgggaaaga agctggtagc gtccggcgcc tgttgatttg agttttgggt       2880
ttagcgtgac aagtttgcga gggtgatcgg agtaatcagt aaatagctct ccgcctacaa       2940
tgacgtcata accatgattt ctggtttttct gacgtccgtt atcagttccc tccgaccacg       3000
ccagcatatc gaggaacgcc ttacgttgat tattgatttc taccatcttc tactccggct       3060
tttttagcag cgaagcgttt gataagcgaa ccaatcgagt cagtaccgat gtagccgata       3120
```

```
aacacgctcg ttatataagc gagattgcta cttagtccgg cgaagtcgag aaggtcacga    3180
atgaactagg cgataatggc gcacatcgtt gcgtcgatta ctgttttgt aaacgcaccg    3240 ccattatatc tgccgcgaag gtacgccatt gcaaacgcaa ggattgcccc gatgccttgt    3300
tcctttgccg cgagaatggc ggccaacagg tcatgttttt ctggcatctt catgtcttac    3360
ccccaataag gggatttgct ctatttaatt aggaataagg tcgattactg atagaacaaa    3420
tccaggctac tgtgtttagt aatcagattt gttcgtgacc gatatgcacg ggcaaaacgg    3480
caggaggttg ttagcgcaaa aaaaaaattc caaaaaaaaa attccaaaaa aaaaaagcga    3540
ctaacaaaca caatctgatg gcagcgacta acaaacacaa tctgatggc             3589
```

<210> SEQ ID NO 30
<211> LENGTH: 3572
<212> TYPE: DNA
<213> ORGANISM: Artificial Sequence
<220> FEATURE:
<223> OTHER INFORMATION: DNA sequence 1 as in priority document
<220> FEATURE:
<221> NAME/KEY: misc_feature
<222> LOCATION: (46)..(47)
<223> OTHER INFORMATION: Modified by 4 iSpC3; C3 phosphoramidite spacer
<220> FEATURE:
<221> NAME/KEY: misc_feature
<222> LOCATION: (73)..(74)
<223> OTHER INFORMATION: Modified by 4 i5NitInd; 5-Nitroindole,
    universal base

<400> SEQUENCE: 30

```
tttttttttt tttttttttt tttttttttt tttttttttt tttttggtt gtttctgttg      60 gtgctgatat tgcgccatca gattgtgttt gttagtcgct tttttttttt ggaattttt     120 ttttggaatt ttttttttgc gctaacaacc tcctgccgtt ttgcccgtgc atatcggtca    180
cgaacaaatc tgattactaa acacagtagc ctggatttgt tctatcagta atcgaccta     240 ttcctaatta aatagagcaa atccccttat tgggggtaag acatgaagat gccagaaaaa    300
catgacctgt tggccgccat tctcgcggca aaggaacaag gcatcggggc aatccttgcg    360
tttgcaatgg cgtaccttcg cggcagatat aatggcggtg cgtttacaaa aacagtaatc    420
gacgcaacga tgtgcgccat tatcgcctag ttcattcgtg accttctcga cttcgccgga    480
ctaagtagca atctcgctta taacgagc gtgtttatcg gctacatcgg tactgactcg    540
attggttcgc ttatcaaacg cttcgctgct aaaaaagccg gagtagaaga tggtagaaat    600
caataatcaa cgtaaggcgt tcctcgatat gctggcgtgg tcggagggaa ctgataacgg    660
acgtcagaaa accagaaatc atggttatga cgtcattgta ggcggagagc tatttactga    720
ttactccgat caccctcgca aacttgtcac gctaaaccca aaactcaaat caacaggcgc    780
cggacgctac cagcttcttt cccgttggtg ggatgcctac cgcaagcagc ttggcctgaa    840
agacttctct ccgaaaagtc aggacgctgt ggcattgcag cagattaagg agcgtggcgc    900
tttacctatg attgatcgtg gtgatatccg tcaggcaatc gaccgttgca gcaatatctg    960
ggcttcactg ccgggcgctg gttatggtca gttcgagcat aaggctgaca gcctgattgc   1020
aaaattcaaa gaagcgggcg gaacggtcag agagattgat gtatgagcag agtcaccgcg   1080
attatctccg ctctggttat ctgcatcatc gtctgcctgt catgggctgt taatcattac   1140
cgtgataacg ccattaccta caaagcccag cgcgacaaaa atgccagaga actgaagctg   1200
gcgaacgcgg caattactga catgcagatg cgtcagcgtg atgttgctgc gctcgatgca   1260
aaatacacga aggagttagc tgatgctaaa gctgaaaatg atgctctgcg tgatgatgtt   1320
```

-continued

```
gccgctggtc gtcgtcggtt gcacatcaaa gcagtctgtc agtcagtgcg tgaagccacc      1380
accgcctccg gcgtggataa tgcagcctcc ccccgactgg cagacaccgc tgaacgggat      1440
tatttcaccc tcagagagag gctgatcact atgcaaaaac aactggaagg aacccagaag      1500
tatattaatg agcagtgcag atagagttgc ccatatcgat gggcaactca tgcaattatt      1560
gtgagcaata cacacgcgct tccagcggag tataaatgcc taaagtaata aaaccgagca      1620
atccatttac gaatgtttgc tgggtttctg ttttaacaac attttctgcg ccgccacaaa      1680
ttttggctgc atcgacagtt ttcttctgcc caattccaga aacgaagaaa tgatgggtga      1740
tggtttcctt tggtgctact gctgccggtt tgttttgaac agtaaacgtc tgttgagcac      1800
atcctgtaat aagcagggcc agcgcagtag cgagtagcat ttttttcatg gtgttattcc      1860
cgatgctttt tgaagttcgc agaatcgtat gtgtagaaaa ttaaacaaac cctaaacaat      1920
gagttgaaat ttcatattgt taatatttat taatgtatgt caggtgcgat gaatcgtcat      1980
tgtattcccg gattaactat gtccacagcc ctgacgggga acttctctgc gggagtgtcc      2040
gggaataatt aaaacgatgc acacagggtt tagcgcgtac acgtattgca ttatgccaac      2100
gccccggtgc tgacacggaa gaaaccggac gttatgattt agcgtggaaa gatttgtgta      2160
gtgttctgaa tgctctcagt aaatagtaat gaattatcaa aggtatagta atatctttta      2220
tgttcatgga tatttgtaac ccatcggaaa actcctgctt tagcaagatt ttccctgtat      2280
tgctgaaatg tgatttctct tgatttcaac ctatcatagg acgtttctat aagatgcgtg      2340
tttcttgaga atttaacatt tacaaccttt ttaagtcctt ttattaacac ggtgttatcg      2400
ttttctaaca cgatgtgaat attatctgtg gctagatagt aaatataatg tgagacgttg      2460
tgacgtttta gttcagaata aaacaattca cagtctaaat cttttcgcac ttgatcgaat      2520
atttctttaa aaatggcaac ctgagccatt ggtaaaacct tccatgtgat acgagggcgc      2580
gtagtttgca ttatcgtttt tatcgtttca atctggtctg acctccttgt gttttgttga      2640
tgatttatgt caaatattag gaatgttttc acttaatagt attggttgcg taacaaagtg      2700
cggtcctgct ggcattctgg agggaaatac aaccgacaga tgtatgtaag gccaacgtgc      2760
tcaaatcttc atacagaaag atttgaagta atatttaac cgctagatga agagcaagcg      2820
catggagcga caaatgaat aaagaacaat ctgctgatga tccctccgtg gatctgattc      2880
gtgtaaaaaa tatgcttaat agcaccattt ctatgagtta ccctgatgtt gtaattgcat      2940
gtatagaaca taaggtgtct ctggaagcat tcagagcaat tgaggcagcg ttggtgaagc      3000
acgataataa tatgaaggat tattccctgg tggttgactg atcaccataa ctgctaatca      3060
ttcaaactat ttagtctgtg acagagccaa cacgcagtct gtcactgtca ggaaagtggt      3120
aaaactgcaa ctcaattact gcaatgccct cgtaattaag tgaatttaca atatcgtcct      3180
gttcggaggg aagaacgcgg gatgttcatt cttcatcact tttaattgat gtatatgctc      3240
tcttttctga cgttagtctc cgacggcagg cttcaatgac ccaggctgag aaattcccgg      3300
acccttttg ctcaagagcg atgttaattt gttcaatcat ttggttagga aagcggatgt      3360
tgcgggttgt tgttctgcgg gttctgttct tcgttgacat gaggttgccc cgtattcagt      3420
gtcgctgatt tgtattgtct gaagttgttt ttacgttaag ttgatgcaga tcaattaata      3480
cgatacctgc gtcataattg attatttgac gtggtttgat ggcctccacg cacgttgtga      3540
tatgtagatg ataatcatta tcactttacg gg                                   3572
```

<210> SEQ ID NO 31

<211> LENGTH: 3525
<212> TYPE: DNA
<213> ORGANISM: Artificial Sequence
<220> FEATURE:
<223> OTHER INFORMATION: DNA sequence 2 as in priority document

<400> SEQUENCE: 31

| | | | | | |
|---|---|---|---|---|---|
| ggtaccttt | ttttcaccgg | aaaggacccg | taaagtgata | atgattatca | tctacatatc | 60 |
| acaacgtgcg | tggaggccat | caaaccacgt | caaataatca | attatgacgc | aggtatcgta | 120 |
| ttaattgatc | tgcatcaact | taacgtaaaa | acaacttcag | acaatacaaa | tcagcgacac | 180 |
| tgaatacggg | gcaacctcat | gtcaacgaag | aacagaaccc | gcagaacaac | aacccgcaac | 240 |
| atccgctttc | ctaaccaaat | gattgaacaa | attaacatcg | ctcttgagca | aaaagggtcc | 300 |
| gggaatttct | cagcctgggt | cattgaagcc | tgccgtcgga | gactaacgtc | agaaaagaga | 360 |
| gcatatacat | caattaaaag | tgatgaagaa | tgaacatccc | gcgttcttcc | ctccgaacag | 420 |
| gacgatattg | taaattcact | taattacgag | ggcattgcag | taattgagtt | gcagttttac | 480 |
| cactttcctg | acagtgacag | actgcgtgtt | ggctctgtca | cagactaaat | agtttgaatg | 540 |
| attagcagtt | atggtgatca | gtcaaccacc | agggaataat | ccttcatatt | attatcgtgc | 600 |
| ttcaccaacg | ctgcctcaat | tgctctgaat | gcttccagag | acaccttatg | ttctatacat | 660 |
| gcaattacaa | catcagggta | actcatagaa | atggtgctat | taagcatatt | ttttacacga | 720 |
| atcagatcca | cggagggatc | atcagcagat | tgttctttat | tcattttgtc | gctccatgcg | 780 |
| cttgctcttc | atctagcggt | taaaatatta | cttcaaatct | ttctgtatga | agatttgagc | 840 |
| acgttggcct | tacatacatc | tgtcggttgt | atttccctcc | agaatgccag | caggaccgca | 900 |
| ctttgttacg | caaccaatac | tattaagtga | aaacattcct | aatatttgac | ataaatcatc | 960 |
| aacaaaacac | aaggaggtca | gaccagattg | aaacgataaa | aacgataatg | caaactacgc | 1020 |
| gccctcgtat | cacatggaag | gttttaccaa | tggctcaggt | tgccattttt | aaagaaatat | 1080 |
| tcgatcaagt | gcgaaaagat | ttagactgtg | aattgtttta | ttctgaacta | aaacgtcaca | 1140 |
| acgtctcaca | ttatatttac | tatctagcca | cagataatat | tcacatcgtg | ttagaaaacg | 1200 |
| ataacaccgt | gttaataaaa | ggacttaaaa | aggttgtaaa | tgttaaattc | tcaagaaaca | 1260 |
| cgcatcttat | agaaacgtcc | tatgataggt | tgaaatcaag | agaaatcaca | tttcagcaat | 1320 |
| acagggaaaa | tcttgctaaa | gcaggagttt | tccgatgggt | tacaaatatc | catgaacata | 1380 |
| aaagatatta | ctatacctt | gataattcat | tactatttac | tgagagcatt | cagaacacta | 1440 |
| cacaaatctt | tccacgctaa | atcataacgt | ccggtttctt | ccgtgtcagc | accggggcgt | 1500 |
| tggcataatg | caatacgtgt | acgcgctaaa | ccctgtgtgc | atcgttttaa | ttattcccgg | 1560 |
| acactcccgc | agagaagttc | cccgtcaggg | ctgtggacat | agttaatccg | ggaatacaat | 1620 |
| gacgattcat | cgcacctgac | atacattaat | aaatattaac | aatatgaaat | ttcaactcat | 1680 |
| tgtttagggt | ttgtttaatt | ttctacacat | acgattctgc | gaacttcaaa | aagcatcggg | 1740 |
| aataacacca | tgaaaaaaat | gctactcgct | actgcgctgg | ccctgcttat | tacaggatgt | 1800 |
| gctcaacaga | cgtttactgt | tcaaaacaaa | ccggcagcag | tagcaccaaa | ggaaaccatc | 1860 |
| acccatcatt | tcttcgtttc | tggaattggg | cagaagaaaa | ctgtcgatgc | agccaaaatt | 1920 |
| tgtggcggcg | cagaaaatgt | tgttaaaaca | gaaacccagc | aaacattcgt | aaatggattg | 1980 |
| ctcggttta | ttactttagg | catttatact | ccgctggaag | cgcgtgtgta | ttgctcacaa | 2040 |
| taattgcatg | agttgcccat | cgatatgggc | aactctatct | gcactgctca | ttaatatact | 2100 |
| tctgggttcc | ttccagttgt | ttttgcatag | tgatcagcct | ctctctgagg | gtgaaataat | 2160 |

```
cccgttcagc ggtgtctgcc agtcggggg aggctgcatt atccacgccg gaggcggtgg    2220
tggcttcacg cactgactga cagactgctt tgatgtgcaa ccgacgacga ccagcggcaa    2280
catcatcacg cagagcatca ttttcagctt tagcatcagc taactccttc gtgtattttg    2340
catcgagcgc agcaacatca cgctgacgca tctgcatgtc agtaattgcc gcgttcgcca    2400
gcttcagttc tctggcattt ttgtcgcgct gggctttgta ggtaatggcg ttatcacggt    2460
aatgattaac agcccatgac aggcagacga tgatgcagat aaccagagcg agataatcg    2520 cggtgactct gctcatacat caatctctct gaccgttccg cccgcttctt tgaattttgc    2580
aatcaggctg tcagccttat gctcgaactg accataacca gcgcccggca gtgaagccca    2640
gatattgctg caacggtcga ttgcctgacg gatatcacca cgatcaatca taggtaaagc    2700
gccacgctcc ttaatctgct gcaatgccac agcgtcctga cttttcggag agaagtcttt    2760
caggccaagc tgcttgcggt aggcatccca ccaacgggaa agaagctggt agcgtccggc    2820
gcctgttgat ttgagttttg ggtttagcgt gacaagtttg cgagggtgat cggagtaatc    2880
agtaaatagc tctccgccta caatgacgtc ataaccatga tttctggttt tctgacgtcc    2940
gttatcagtt ccctccgacc acgccagcat atcgaggaac gccttacgtt gattattgat    3000
ttctaccatc ttctactccg gcttttttag cagcgaagcg tttgataagc gaaccaatcg    3060
agtcagtacc gatgtagccg ataaacacgc tcgttatata agcgagattg ctacttagtc    3120
cggcgaagtc gagaaggtca cgaatgaact aggcgataat ggcgcacatc gttgcgtcga    3180
ttactgtttt tgtaaacgca ccgccattat atctgccgcg aaggtacgcc attgcaaacg    3240
caaggattgc cccgatgcct tgttcctttg ccgcgagaat ggcggccaac aggtcatgtt    3300
tttctggcat cttcatgtct tacccccaat aaggggattt gctctattta attaggaata    3360
aggtcgatta ctgatagaac aaatccaggc tactgtgttt agtaatcaga tttgttcgtg    3420
accgatatgc acgggcaaaa cggcaggagg ttgttagcgc aaaaaaaaaa ttccaaaaaa    3480
aaaattccaa aaaaaaaag cgactaacaa acacaatctg atggc                    3525
```

<210> SEQ ID NO 32  
<211> LENGTH: 30  
<212> TYPE: DNA  
<213> ORGANISM: Artificial Sequence  
<220> FEATURE:  
<223> OTHER INFORMATION: DNA sequence 3  
<220> FEATURE:  
<221> NAME/KEY: misc_feature  
<222> LOCATION: (28)..(29)  
<223> OTHER INFORMATION: Modified by 6 iSp18; 18-atom hexa-ethyleneglycol spacer  
<220> FEATURE:  
<221> NAME/KEY: misc_feature  
<222> LOCATION: (30)..(30)  
<223> OTHER INFORMATION: conjugated to 3CholTEG; 3' Cholesteryl-TEG

<400> SEQUENCE: 32
gcaatatcag caccaacaga aacaaccttt                                         30

<210> SEQ ID NO 33  
<211> LENGTH: 84  
<212> TYPE: DNA  
<213> ORGANISM: Artificial Sequence  
<220> FEATURE:  
<223> OTHER INFORMATION: DNA sequence 4  
<220> FEATURE:  
<221> NAME/KEY: misc_feature  
<222> LOCATION: (49)..(50)  
<223> OTHER INFORMATION: Modified by 4 iSpC3; C3 phosphoramidite spacer

<400> SEQUENCE: 33
cgttctgttt atgtttcttg tttgttagcc ttttttttt ttttttttt ttttggctaa    60 caaacaagaa acataaacag aacg    84

<210> SEQ ID NO 34
<211> LENGTH: 10
<212> TYPE: DNA
<213> ORGANISM: Artificial Sequence
<220> FEATURE:
<223> OTHER INFORMATION: AE202
<220> FEATURE:
<221> NAME/KEY: misc_feature
<222> LOCATION: (1)..(1)
<223> OTHER INFORMATION: conjugated to 5CholTEG; 5' Cholesteryl-TEG
<220> FEATURE:
<221> NAME/KEY: misc_feature
<222> LOCATION: (1)..(10)
<223> OTHER INFORMATION: n is inosine (i)

<400> SEQUENCE: 34 nnnnnnnnnn    10

<210> SEQ ID NO 35
<211> LENGTH: 115
<212> TYPE: DNA
<213> ORGANISM: Artificial Sequence
<220> FEATURE:
<223> OTHER INFORMATION: AE186

<400> SEQUENCE: 35
caaataagaa cattatgatc agtagggcta acaaacaaga aacataaaca gaacgtgctt    60
acggttcact actcacgacg atgttttttt tggtaccttt tttttcaccg gaaag    115

<210> SEQ ID NO 36
<211> LENGTH: 28
<212> TYPE: DNA
<213> ORGANISM: Artificial Sequence
<220> FEATURE:
<223> OTHER INFORMATION: TE60 corrected
<220> FEATURE:
<221> NAME/KEY: misc_feature
<222> LOCATION: (26)..(27)
<223> OTHER INFORMATION: Modified by 6 iSp18; 18-atom
       hexa-ethyleneglycol spacer
<220> FEATURE:
<221> NAME/KEY: misc_feature
<222> LOCATION: (28)..(28)
<223> OTHER INFORMATION: conjugated to 3CholTEG; 3' Cholesteryl-TEG

<400> SEQUENCE: 36
ctactgatca taatgttctt atttgttt    28

<210> SEQ ID NO 37
<211> LENGTH: 17
<212> TYPE: DNA
<213> ORGANISM: Artificial Sequence
<220> FEATURE:
<223> OTHER INFORMATION: TE60 as in priority document
<220> FEATURE:
<221> NAME/KEY: misc_feature
<222> LOCATION: (15)..(16)
<223> OTHER INFORMATION: Modified by 6 iSp18; 18-atom
       hexa-ethyleneglycol spacer
<220> FEATURE:
<221> NAME/KEY: misc_feature
<222> LOCATION: (17)..(17)
<223> OTHER INFORMATION: conjugated to 3CholTEG; 3' Cholesteryl-TEG

```
<400> SEQUENCE: 37
gcaatatcag caccttt                                                   17

<210> SEQ ID NO 38
<211> LENGTH: 20
<212> TYPE: DNA
<213> ORGANISM: Artificial Sequence
<220> FEATURE:
<223> OTHER INFORMATION: AE203
<220> FEATURE:
<221> NAME/KEY: misc_feature
<222> LOCATION: (1)..(1)
<223> OTHER INFORMATION: conjugated to 5CholTEG; 5' Cholesteryl-TEG
<220> FEATURE:
<221> NAME/KEY: misc_feature
<222> LOCATION: (1)..(20)
<223> OTHER INFORMATION: n is inosine (i)

<400> SEQUENCE: 38
nnnnnnnnnn nnnnnnnnnn                                                20

<210> SEQ ID NO 39
<211> LENGTH: 30
<212> TYPE: DNA
<213> ORGANISM: Artificial Sequence
<220> FEATURE:
<223> OTHER INFORMATION: AE210
<220> FEATURE:
<221> NAME/KEY: misc_feature
<222> LOCATION: (1)..(1)
<223> OTHER INFORMATION: conjugated to 5' Biotin dT
<220> FEATURE:
<221> NAME/KEY: misc_feature
<222> LOCATION: (1)..(30)
<223> OTHER INFORMATION: n is inosine (i)
<220> FEATURE:
<221> NAME/KEY: misc_feature
<222> LOCATION: (30)..(30)
<223> OTHER INFORMATION: conjugated to 5CholTEG; 5' Cholesteryl-TEG

<400> SEQUENCE: 39
nnnnnnnnnn nnnnnnnnnn nnnnnnnnnn                                     30

<210> SEQ ID NO 40
<211> LENGTH: 10
<212> TYPE: DNA
<213> ORGANISM: Artificial Sequence
<220> FEATURE:
<223> OTHER INFORMATION: AE191
<220> FEATURE:
<221> NAME/KEY: misc_feature
<222> LOCATION: (1)..(1)
<223> OTHER INFORMATION: conjugated to 5' Biotin dT
<220> FEATURE:
<221> NAME/KEY: misc_feature
<222> LOCATION: (1)..(10)
<223> OTHER INFORMATION: n is inosine (i)

<400> SEQUENCE: 40 nnnnnnnnnn                                                           10

<210> SEQ ID NO 41
<211> LENGTH: 20
<212> TYPE: DNA
<213> ORGANISM: Artificial Sequence
<220> FEATURE:
<223> OTHER INFORMATION: AE192
<220> FEATURE:
<221> NAME/KEY: misc_feature
<222> LOCATION: (1)..(1)
<223> OTHER INFORMATION: is conjugated to 5' Biotin dT
```

```
<220> FEATURE:
<221> NAME/KEY: misc_feature
<222> LOCATION: (1)..(20)
<223> OTHER INFORMATION: n is inosine (i)

<400> SEQUENCE: 41
nnnnnnnnnn nnnnnnnnnn                                              20

<210> SEQ ID NO 42
<211> LENGTH: 30
<212> TYPE: DNA
<213> ORGANISM: Artificial Sequence
<220> FEATURE:
<223> OTHER INFORMATION: AE193
<220> FEATURE:
<221> NAME/KEY: misc_feature
<222> LOCATION: (1)..(1)
<223> OTHER INFORMATION: is conjugated to 5' Biotin dT
<220> FEATURE:
<221> NAME/KEY: misc_feature
<222> LOCATION: (1)..(30)
<223> OTHER INFORMATION: n is inosine (i)

<400> SEQUENCE: 42
nnnnnnnnnn nnnnnnnnnn nnnnnnnnnn                                   30

<210> SEQ ID NO 43
<211> LENGTH: 40
<212> TYPE: DNA
<213> ORGANISM: Artificial Sequence
<220> FEATURE:
<223> OTHER INFORMATION: AE263

<400> SEQUENCE: 43
gggtccggga atttctcagc ctgggtcatt gaagcctgcc                         40

<210> SEQ ID NO 44
<211> LENGTH: 40
<212> TYPE: DNA
<213> ORGANISM: Artificial Sequence
<220> FEATURE:
<223> OTHER INFORMATION: AE264

<400> SEQUENCE: 44
ccaaatgatt gaacaaatta acatcgctct tgagcaaaaa                         40

<210> SEQ ID NO 45
<211> LENGTH: 40
<212> TYPE: DNA
<213> ORGANISM: Artificial Sequence
<220> FEATURE:
<223> OTHER INFORMATION: AE265

<400> SEQUENCE: 45
gaacccgcag aacaacaacc cgcaacatcc gctttcctaa                         40

<210> SEQ ID NO 46
<211> LENGTH: 40
<212> TYPE: DNA
<213> ORGANISM: Artificial Sequence
<220> FEATURE:
<223> OTHER INFORMATION: AE266

<400> SEQUENCE: 46
cgacactgaa tacggggcaa cctcatgtca acgaagaaca                         40

<210> SEQ ID NO 47
```

```
<211> LENGTH: 40
<212> TYPE: DNA
<213> ORGANISM: Artificial Sequence
<220> FEATURE:
<223> OTHER INFORMATION: AE267

<400> SEQUENCE: 47
tcaacttaac gtaaaaacaa cttcagacaa tacaaatcag                              40

<210> SEQ ID NO 48
<211> LENGTH: 40
<212> TYPE: DNA
<213> ORGANISM: Artificial Sequence
<220> FEATURE:
<223> OTHER INFORMATION: AE268

<400> SEQUENCE: 48
taatcaatta tgacgcaggt atcgtattaa ttgatctgca                              40

<210> SEQ ID NO 49
<211> LENGTH: 40
<212> TYPE: DNA
<213> ORGANISM: Artificial Sequence
<220> FEATURE:
<223> OTHER INFORMATION: AE269

<400> SEQUENCE: 49
catatcacaa cgtgcgtgga ggccatcaaa ccacgtcaaa                              40

<210> SEQ ID NO 50
<211> LENGTH: 40
<212> TYPE: DNA
<213> ORGANISM: Artificial Sequence
<220> FEATURE:
<223> OTHER INFORMATION: AE270

<400> SEQUENCE: 50
caccggaaag gacccgtaaa gtgataatga ttatcatcta                              40

<210> SEQ ID NO 51
<211> LENGTH: 40
<212> TYPE: DNA
<213> ORGANISM: Artificial Sequence
<220> FEATURE:
<223> OTHER INFORMATION: AE271

<400> SEQUENCE: 51
tcactactca cgacgatgtt ttttttggta cctttttttt                              40

<210> SEQ ID NO 52
<211> LENGTH: 40
<212> TYPE: DNA
<213> ORGANISM: Artificial Sequence
<220> FEATURE:
<223> OTHER INFORMATION: AE272

<400> SEQUENCE: 52
ggctaacaaa caagaaacat aaacagaacg tgcttacggt                              40

<210> SEQ ID NO 53
<211> LENGTH: 20
<212> TYPE: DNA
<213> ORGANISM: Artificial Sequence
<220> FEATURE:
<223> OTHER INFORMATION: AE273

<400> SEQUENCE: 53
```

```
ctgggtcatt gaagcctgcc                                            20

<210> SEQ ID NO 54
<211> LENGTH: 20
<212> TYPE: DNA
<213> ORGANISM: Artificial Sequence
<220> FEATURE:
<223> OTHER INFORMATION: AE274

<400> SEQUENCE: 54
gggtccggga atttctcagc                                            20

<210> SEQ ID NO 55
<211> LENGTH: 20
<212> TYPE: DNA
<213> ORGANISM: Artificial Sequence
<220> FEATURE:
<223> OTHER INFORMATION: AE275

<400> SEQUENCE: 55
acatcgctct tgagcaaaaa                                            20

<210> SEQ ID NO 56
<211> LENGTH: 20
<212> TYPE: DNA
<213> ORGANISM: Artificial Sequence
<220> FEATURE:
<223> OTHER INFORMATION: AE276

<400> SEQUENCE: 56
ccaaatgatt gaacaaatta                                            20

<210> SEQ ID NO 57
<211> LENGTH: 20
<212> TYPE: DNA
<213> ORGANISM: Artificial Sequence
<220> FEATURE:
<223> OTHER INFORMATION: AE277

<400> SEQUENCE: 57
cgcaacatcc gctttcctaa                                            20

<210> SEQ ID NO 58
<211> LENGTH: 20
<212> TYPE: DNA
<213> ORGANISM: Artificial Sequence
<220> FEATURE:
<223> OTHER INFORMATION: AE278

<400> SEQUENCE: 58
gaacccgcag aacaacaacc                                            20

<210> SEQ ID NO 59
<211> LENGTH: 20
<212> TYPE: DNA
<213> ORGANISM: Artificial Sequence
<220> FEATURE:
<223> OTHER INFORMATION: AE279

<400> SEQUENCE: 59
cctcatgtca acgaagaaca                                            20

<210> SEQ ID NO 60
<211> LENGTH: 20
<212> TYPE: DNA
```

```
<213> ORGANISM: Artificial Sequence
<220> FEATURE:
<223> OTHER INFORMATION: AE280

<400> SEQUENCE: 60
cgacactgaa tacggggcaa                                                     20

<210> SEQ ID NO 61
<211> LENGTH: 20
<212> TYPE: DNA
<213> ORGANISM: Artificial Sequence
<220> FEATURE:
<223> OTHER INFORMATION: AE281

<400> SEQUENCE: 61
cttcagacaa tacaaatcag                                                     20

<210> SEQ ID NO 62
<211> LENGTH: 20
<212> TYPE: DNA
<213> ORGANISM: Artificial Sequence
<220> FEATURE:
<223> OTHER INFORMATION: AE282

<400> SEQUENCE: 62
tcaacttaac gtaaaaacaa                                                     20

<210> SEQ ID NO 63
<211> LENGTH: 20
<212> TYPE: DNA
<213> ORGANISM: Artificial Sequence
<220> FEATURE:
<223> OTHER INFORMATION: AE283

<400> SEQUENCE: 63
atcgtattaa ttgatctgca                                                     20

<210> SEQ ID NO 64
<211> LENGTH: 20
<212> TYPE: DNA
<213> ORGANISM: Artificial Sequence
<220> FEATURE:
<223> OTHER INFORMATION: AE284

<400> SEQUENCE: 64
taatcaatta tgacgcaggt                                                     20

<210> SEQ ID NO 65
<211> LENGTH: 20
<212> TYPE: DNA
<213> ORGANISM: Artificial Sequence
<220> FEATURE:
<223> OTHER INFORMATION: AE285

<400> SEQUENCE: 65
ggccatcaaa ccacgtcaaa                                                     20

<210> SEQ ID NO 66
<211> LENGTH: 20
<212> TYPE: DNA
<213> ORGANISM: Artificial Sequence
<220> FEATURE:
<223> OTHER INFORMATION: AE286

<400> SEQUENCE: 66
catatcacaa cgtgcgtgga                                                     20
```

```
<210> SEQ ID NO 67
<211> LENGTH: 20
<212> TYPE: DNA
<213> ORGANISM: Artificial Sequence
<220> FEATURE:
<223> OTHER INFORMATION: AE287

<400> SEQUENCE: 67
gtgataatga ttatcatcta                                              20

<210> SEQ ID NO 68
<211> LENGTH: 20
<212> TYPE: DNA
<213> ORGANISM: Artificial Sequence
<220> FEATURE:
<223> OTHER INFORMATION: AE288

<400> SEQUENCE: 68
caccggaaag gacccgtaaa                                              20

<210> SEQ ID NO 69
<211> LENGTH: 20
<212> TYPE: DNA
<213> ORGANISM: Artificial Sequence
<220> FEATURE:
<223> OTHER INFORMATION: AE289

<400> SEQUENCE: 69 tttttggta cctttttttt                                               20

<210> SEQ ID NO 70
<211> LENGTH: 20
<212> TYPE: DNA
<213> ORGANISM: Artificial Sequence
<220> FEATURE:
<223> OTHER INFORMATION: AE290

<400> SEQUENCE: 70
tcactactca cgacgatgtt                                              20

<210> SEQ ID NO 71
<211> LENGTH: 20
<212> TYPE: DNA
<213> ORGANISM: Artificial Sequence
<220> FEATURE:
<223> OTHER INFORMATION: AE291

<400> SEQUENCE: 71
aaacagaacg tgcttacggt                                              20

<210> SEQ ID NO 72
<211> LENGTH: 20
<212> TYPE: DNA
<213> ORGANISM: Artificial Sequence
<220> FEATURE:
<223> OTHER INFORMATION: AE292

<400> SEQUENCE: 72
ggctaacaaa caagaaacat                                              20

<210> SEQ ID NO 73
<211> LENGTH: 80
<212> TYPE: DNA
<213> ORGANISM: Artificial Sequence
<220> FEATURE:
```

<223> OTHER INFORMATION: AE258

<400> SEQUENCE: 73
ccaaatgatt gaacaaatta acatcgctct tgagcaaaaa gggtccggga atttctcagc    60
ctgggtcatt gaagcctgcc    80

<210> SEQ ID NO 74
<211> LENGTH: 80
<212> TYPE: DNA
<213> ORGANISM: Artificial Sequence
<220> FEATURE:
<223> OTHER INFORMATION: AE259

<400> SEQUENCE: 74
cgacactgaa tacggggcaa cctcatgtca acgaagaaca gaacccgcag aacaacaacc    60
cgcaacatcc gctttcctaa    80

<210> SEQ ID NO 75
<211> LENGTH: 90
<212> TYPE: DNA
<213> ORGANISM: Artificial Sequence
<220> FEATURE:
<223> OTHER INFORMATION: AE182

<400> SEQUENCE: 75
atctgcactg ctcattaata tacttctggg ttccttccag ttgttttgc atagtgatca    60 gcctctctct gagggtgaaa taatcccgtt    90

<210> SEQ ID NO 76
<211> LENGTH: 95
<212> TYPE: DNA
<213> ORGANISM: Artificial Sequence
<220> FEATURE:
<223> OTHER INFORMATION: TH14
<220> FEATURE:
<221> NAME/KEY: misc_feature
<222> LOCATION: (1)..(1)
<223> OTHER INFORMATION: is 5' phosphorylated
<220> FEATURE:
<221> NAME/KEY: misc_feature
<222> LOCATION: (48)..(49)
<223> OTHER INFORMATION: Modified by 4 iSp18; 18-atom
     hexa-ethyleneglycol spacer

<400> SEQUENCE: 76
cgtggttggt gtggttggcg gacactgatt gacacggttt agtagagctt ttttttttt    60 ttttttttt tcgccaacca caccaaccac gtcct    95

<210> SEQ ID NO 77
<211> LENGTH: 95
<212> TYPE: DNA
<213> ORGANISM: Artificial Sequence
<220> FEATURE:
<223> OTHER INFORMATION: TH15
<220> FEATURE:
<221> NAME/KEY: misc_feature
<222> LOCATION: (1)..(1)
<223> OTHER INFORMATION: is 5' phosphorylated
<220> FEATURE:
<221> NAME/KEY: misc_feature
<222> LOCATION: (48)..(49)
<223> OTHER INFORMATION: Modified by 4 iSp18; 18-atom
     hexa-ethyleneglycol spacer

<400> SEQUENCE: 77
cgtccaacca caccaacccg gacactgatt gacacggttt agtagagctt ttttttttt    60 tttttttttt tcgggttggt gtggttggac gtcct                          95

<210> SEQ ID NO 78
<211> LENGTH: 122
<212> TYPE: DNA
<213> ORGANISM: Artificial Sequence
<220> FEATURE:
<223> OTHER INFORMATION: TH16
<220> FEATURE:
<221> NAME/KEY: misc_feature
<222> LOCATION: (1)..(1)
<223> OTHER INFORMATION: is 5' phosphorylated
<220> FEATURE:
<221> NAME/KEY: misc_feature
<222> LOCATION: (61)..(62)
<223> OTHER INFORMATION: Modified by 4 iSp18; 18-atom
      hexa-ethyleneglycol spacer

<400> SEQUENCE: 78
cgtagtccgt ggtagggcag gttggggtga ccggacactg attgacacgg tttagtagag    60
cttttttttt tttttttttt tttcgagtc accccaacct gccctaccac ggactacgtc   120
ct                                                                 122

<210> SEQ ID NO 79
<211> LENGTH: 123
<212> TYPE: DNA
<213> ORGANISM: Artificial Sequence
<220> FEATURE:
<223> OTHER INFORMATION: TH17
<220> FEATURE:
<221> NAME/KEY: misc_feature
<222> LOCATION: (1)..(1)
<223> OTHER INFORMATION: is 5' phosphorylated
<220> FEATURE:
<221> NAME/KEY: misc_feature
<222> LOCATION: (62)..(63)
<223> OTHER INFORMATION: Modified by 4 iSp18; 18-atom
      hexa-ethyleneglycol spacer

<400> SEQUENCE: 79
cgtagtcacc ccaacctgcc ctaccacgga ctcggacact gattgacacg gtttagtaga    60 gcttttttttt tttttttttt ttttttcgagt ccgtggtagg gcaggttggg gtgactacgt   120
cct                                                                 123

<210> SEQ ID NO 80
<211> LENGTH: 100
<212> TYPE: DNA
<213> ORGANISM: Artificial Sequence
<220> FEATURE:
<223> OTHER INFORMATION: Control hairpin sequence
<220> FEATURE:
<221> NAME/KEY: misc_feature
<222> LOCATION: (1)..(1)
<223> OTHER INFORMATION: is 5' phosphorylated
<220> FEATURE:
<221> NAME/KEY: misc_feature
<222> LOCATION: (48)..(49)
<223> OTHER INFORMATION: Modified by 4 iSpC3; C3 phosphoramidite spacer

<400> SEQUENCE: 80
cgtcctgtcg ctgtgtctcg gacactgatt gacacggttt agtagagctt tttttttttt    60
tttttttttt tttttcgag acacagcgac aggacgtcct                          100

<210> SEQ ID NO 81
<211> LENGTH: 63
<212> TYPE: DNA

```
<213> ORGANISM: Artificial Sequence
<220> FEATURE:
<223> OTHER INFORMATION: Y adapter sequence 1
<220> FEATURE:
<221> NAME/KEY: misc_feature
<222> LOCATION: (1)..(1)
<223> OTHER INFORMATION: Modified by 30 iSpC3; C3 phosphoramidite spacer
<220> FEATURE:
<221> NAME/KEY: misc_feature
<222> LOCATION: (35)..(36)
<223> OTHER INFORMATION: Modified by 4 iSp18; 18-atom
      hexa-ethyleneglycol spacer

<400> SEQUENCE: 81
ggcgtctgct tgggtgttta acctttttt tttttggttg tttctgttgg tgctgatatt    60
gct                                                                 63

<210> SEQ ID NO 82
<211> LENGTH: 45
<212> TYPE: DNA
<213> ORGANISM: Artificial Sequence
<220> FEATURE:
<223> OTHER INFORMATION: Y adapter sequence 2
<220> FEATURE:
<221> NAME/KEY: misc_feature
<222> LOCATION: (1)..(1)
<223> OTHER INFORMATION: is 5' phosphorylated
<220> FEATURE:
<221> NAME/KEY: misc_feature
<222> LOCATION: (23)..(23)
<223> OTHER INFORMATION: is iBNA-MeC, where BNA is Bridged Nucleic Acid,
      where MeC is methyl cytosine
<220> FEATURE:
<221> NAME/KEY: misc_feature
<222> LOCATION: (24)..(24)
<223> OTHER INFORMATION: is iBNA-A, where BNA is Bridged Nucleic Acid
<220> FEATURE:
<221> NAME/KEY: misc_feature
<222> LOCATION: (25)..(25)
<223> OTHER INFORMATION: is iBNA-A, where BNA is Bridged Nucleic Acid
<220> FEATURE:
<221> NAME/KEY: misc_feature
<222> LOCATION: (26)..(26)
<223> OTHER INFORMATION: is iBNA-MeC, where BNA is Bridged Nucleic Acid,
      where MeC is metylcytosine
<220> FEATURE:
<221> NAME/KEY: misc_feature
<222> LOCATION: (27)..(27)
<223> OTHER INFORMATION: is iBNA-MeC, where BNA is Bridged Nucleic Acid,
      where MeC is metylcytosine

<400> SEQUENCE: 82
gcaatatcag caccaacaga aacaaccttt gaggcgagcg gtcaa                   45

<210> SEQ ID NO 83
<211> LENGTH: 25
<212> TYPE: DNA
<213> ORGANISM: Artificial Sequence
<220> FEATURE:
<223> OTHER INFORMATION: Y adapter sequence 3
<220> FEATURE:
<221> NAME/KEY: misc_feature
<222> LOCATION: (1)..(1)
<223> OTHER INFORMATION: is iBNA-G, where BNA is Bridged Nucleic Acid
<220> FEATURE:
<221> NAME/KEY: misc_feature
<222> LOCATION: (2)..(2)
<223> OTHER INFORMATION: is iBNA-G, where BNA is Bridged Nucleic Acid
<220> FEATURE:
<221> NAME/KEY: misc_feature
<222> LOCATION: (3)..(3)
<223> OTHER INFORMATION: is iBNA-T, where BNA is Bridged Nucleic Acid
<220> FEATURE:
<221> NAME/KEY: misc_feature
```

```
<222> LOCATION: (4)..(4)
<223> OTHER INFORMATION: is iBNA-T, where BNA is Bridged Nucleic Acid
<220> FEATURE:
<221> NAME/KEY: misc_feature
<222> LOCATION: (5)..(5)
<223> OTHER INFORMATION: is iBNA-A, where BNA is Bridged Nucleic Acid

<400> SEQUENCE: 83
ggttaaacac ccaagcagac gcctt                                              25
```